(12) United States Patent
DeLucca

(10) Patent No.: US 7,514,430 B2
(45) Date of Patent: Apr. 7, 2009

(54) PIPERIZINONES AS MODULATORS OF CHEMOKINE RECEPTOR ACTIVITY

(75) Inventor: George V. DeLucca, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 537 days.

(21) Appl. No.: 11/191,447

(22) Filed: Jul. 28, 2005

(65) Prior Publication Data

US 2005/0261311 A1    Nov. 24, 2005

Related U.S. Application Data

(62) Division of application No. 10/246,585, filed on Sep. 18, 2002, now Pat. No. 6,974,869.

(60) Provisional application No. 60/323,166, filed on Sep. 18, 2001.

(51) Int. Cl.
*A61K 31/535* (2006.01)
*C07D 265/30* (2006.01)

(52) U.S. Cl. ............. 514/231; 514/222.52; 514/259.02; 544/106; 544/383; 544/5; 544/8

(58) Field of Classification Search ............. 514/231.2, 514/222.5, 259.02; 544/106, 5, 8, 383
See application file for complete search history.

(56) References Cited

U.S. PATENT DOCUMENTS

| | | | |
|---|---|---|---|
| 4,112,090 | A | 9/1978 | Saikawa et al. |
| 4,587,047 | A | 5/1986 | Breuer et al. |
| 4,598,079 | A | 7/1986 | Beyerle et al. |
| 5,143,916 | A | 9/1992 | Lavielle et al. |
| 5,358,946 | A | 10/1994 | Wilde |
| 5,618,812 | A | 4/1997 | Pineiro et al. |
| 5,635,503 | A | 6/1997 | Poindexter et al. |
| 5,668,151 | A | 9/1997 | Poindexter et al. |
| 5,670,505 | A | 9/1997 | Matsuo et al. |
| 5,756,528 | A | 5/1998 | Anthony et al. |
| 6,127,357 | A | 10/2000 | Cliffe et al. |
| 6,492,370 | B1 | 12/2002 | Mita et al. |

FOREIGN PATENT DOCUMENTS

| | | |
|---|---|---|
| EP | 0903349 | 3/1999 |
| GB | 1518029 | 7/1979 |
| WO | WO9306108 | 4/1993 |
| WO | WO9422846 | 10/1994 |
| WO | WO9513069 | 6/1995 |
| WO | WO9727752 | 8/1997 |
| WO | WO9736605 | 10/1997 |
| WO | WO9736900 | 10/1997 |
| WO | WO9825604 | 6/1998 |
| WO | WO9825617 | 6/1998 |
| WO | WO9904794 | 2/1999 |
| WO | WO9950238 | 10/1999 |
| WO | WO0035452 | 6/2000 |
| WO | WO0198269 | 12/2001 |

*Primary Examiner*—James O. Wilson
*Assistant Examiner*—Paul V. Ward
(74) *Attorney, Agent, or Firm*—Mary K. VanAtten

(57) ABSTRACT

The present application describes modulators of CCR3 of formula (I):

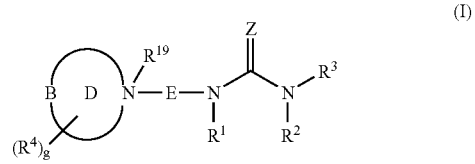

or pharmaceutically acceptable salt forms thereof, useful for the prevention of asthma and other allergic diseases.

19 Claims, No Drawings

PIPERIZINONES AS MODULATORS OF CHEMOKINE RECEPTOR ACTIVITY

This application is a divisional application of U.S. application Ser. No. 10/246,585, filed Sep. 18, 2002 now U.S. Pat No. 6,974,869, which claims priority from Ser. No. 60/323, 166 filed Sep. 18, 2001, both of which are incorporated herein by reference in their entirety.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J. Med., 338, 436-445 (1998) and Rollins, Blood, 90, 909-928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1α, RANTES, MCP-1] (Power et al., J. Biol. Chem., 270, 19495-19500 (1995), Luster, New Eng. J. Med., 338, 436-445 (1998)); CCR-5 (or "CKR-5" OR "CC-CKR-5") [MIP-1α, RANTES, MIP-1β] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [I-309, TARC, MIP-1β] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines, piperizinones and pyrrolidines. These compounds have implicated in the treatment of a variety of disorders.

WO 98/25604 describes spiro-substituted azacycles which are useful as modulators of chemokine receptors:

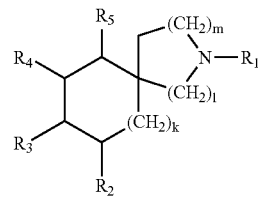

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

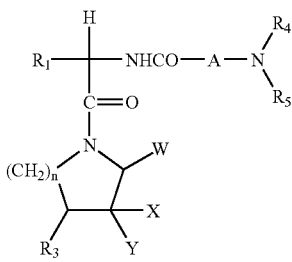

wherein A may be substituted alkyl or Z-substituted alkyl, with Z=NR$_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

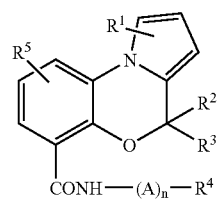

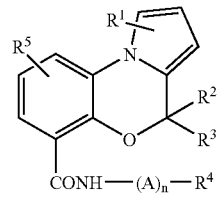

wherein A is lower alkylene and R$^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

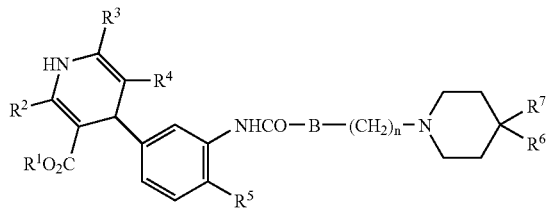

wherein B may be NH, NR$^1$, O, or a bond, and R$^7$ may be substituted phenyl, benzyl, phenethyl and the like.

Patent publication EP 0 903 349 A2 discloses CCR-3 receptor antagonists comprising cyclic amines of the following structure:

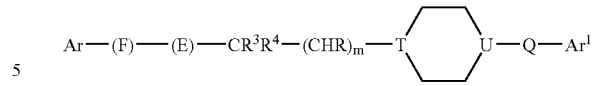

wherein T and U may be both nitrogen or one of T and U is nitrogen and the other is carbon and E may be —NR$^6$CONR$^5$— and others.

WO 97/27752 discloses compounds of the general formula:

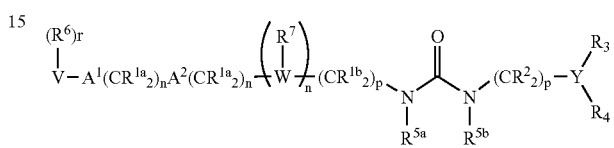

wherein W may be a pyrazole ring. These compounds are claimed to treat cancer as inhibitors of farnesyl-protein transferase.

WO 99/04794 is directed towards modulators of chemokine activity having the general formula:

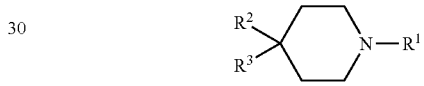

wherein the claimed compounds are exclusively para-substituted piperidines.

WO 94/22846 discloses compounds having the general formula:

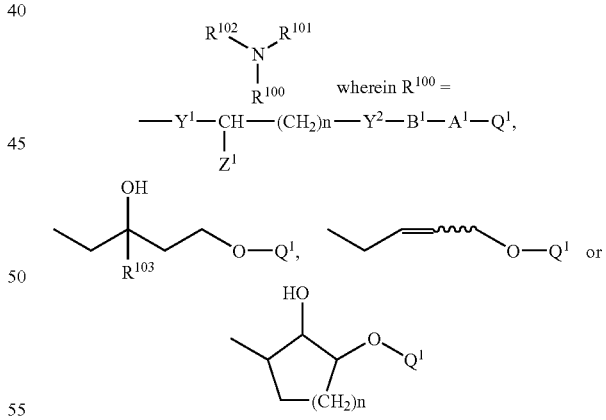

and optionally having the R$^{101}$ and R$^{102}$ connected to form a heterocycle ring. These compounds are disclosed as agents for sensitizing tumor cells or as anti cancer agents.

These reference compounds are readily distinguished structurally by either the nature of the urea functionality, the attachment chain, or the possible substitution of the present invention. The prior art does not disclose nor suggest the unique combination of structural fragments which embody these novel piperizinones as having activity toward the chemokine receptors.

SUMMARY OF THE INVENTION

Accordingly, one aspect of the present invention is to provide novel agonists or antagonists of CCR-3, or pharmaceutically acceptable salts or prodrugs thereof.

The present invention also provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating inflammatory diseases and allergic disorders comprising administering to a host in need of such treatment a therapeutically effective amount of at least one of the compounds of the present invention or a pharmaceutically acceptable salt or prodrug form thereof.

The present invention provides novel piperizinones for use in therapy.

The present invention provides the use of novel piperizinones for the manufacture of a medicament for the treatment of allergic disorders.

These and other features, which will become apparent during the following detailed description, have been achieved by the inventors' discovery that compounds of formula (I):

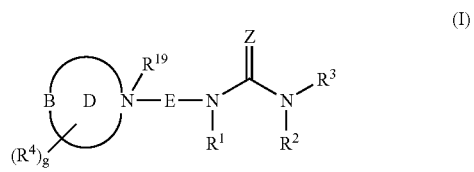

or stereoisomers or pharmaceutically acceptable salts thereof, wherein B, D, E, Z, $R^1$, $R^2$, $R^3$, $R^4$, and $R^{19}$ are defined below, are effective modulators of chemokine activity.

DETAILED DESCRIPTION OF PREFERRED EMBODIMENTS

[1] Thus, in a first embodiment, the present invention provides novel compounds of formula (I):

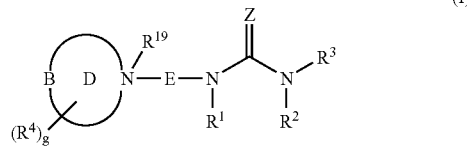

or stereoisomers or pharmaceutically acceptable salts thereof, wherein:

Ring D is a 6-membered ring heterocycle wherein B is O, S, or $NR^{17}$ with the heterocycle further containing at least one carbonyl or sulfonyl therein;

$R^4$ is selected from H, $R^5$ and $R^{13}$;

$R^{17}$ is selected from H, $R^5$ and $R^{18}$;

with the proviso that Ring D contains at least one $R^5$;

Z is selected from O, S, $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

E is $-(CR^7CR^8)-(CR^9R^{10})_v-(CR^{11}R^{12})$ $-(C=O))-(CR^9R^{10})_v-(CR^{11}R^{12})-$, $-(SO_2)-(CR^9R^{10})_v-(CR^{11}R^{12})-$,

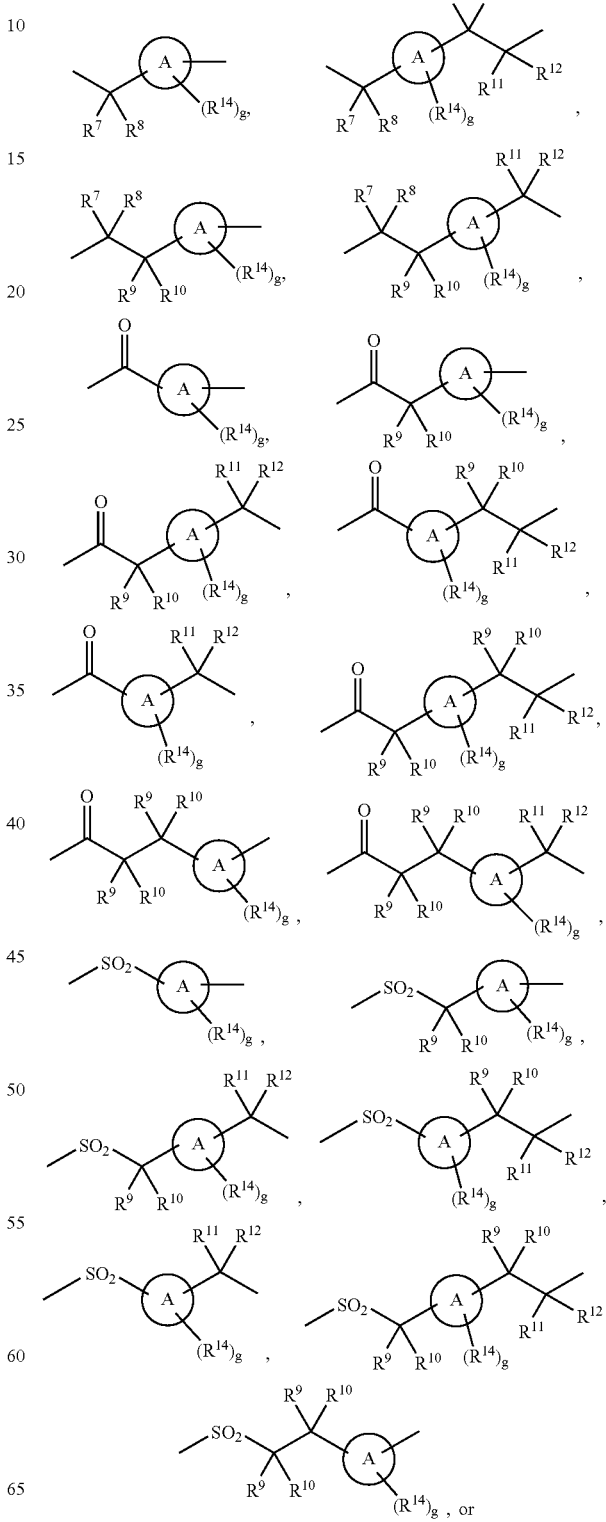

-continued

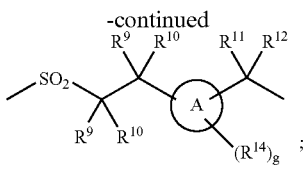

Ring A is a $C_{3-8}$ carbocyclic residue;

$R^1$ and $R^2$ are independently selected from H, $C_{1-8}$ alkyl, $C_{3-8}$ alkenyl, $C_{3-8}$ alkynyl, and a $(CH_2)_r$—$C_{3-10}$ carbocyclic residue substituted with 0-5 $R^a$;

$R^a$, at each occurrence, is independently selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_r$ OH, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is independently selected from H, $C_{1-6}$ alkyl, $C_{3-6}$ cycloalkyl, and phenyl;

$R^c$, at each occurrence, is independently selected from $C_{1-6}$ alkyl, $C_{3-6}$ cycloalkyl, and phenyl;

$R^3$ is selected from a $(CR^{3a}R^{3b})_r$—$C_{3-8}$ carbocyclic residue substituted with 0-5 $R^{15}$; and a $(CR^{3a}R^{3b})_r$-5-10 membered heterocyclic system containing 1-4 heteroatoms selected from N, O, and S, substituted with 0-3 $R^{15}$;

$R^{3a}$ and $R^{3b}$, at each occurrence, are independently selected from H, $C_{1-6}$alkyl, $(CH_2)_rC_{3-6}$ cycloalkyl, and phenyl;

$R^5$ is selected from a $(CR^{5a}R^{5b})_t$—$C_{3-10}$ carbocyclic residue substituted with 0-5 $R^{16}$ and a $(CR^{5a}R^{5b})_r$-5-10 membered heterocyclic system containing 1-4 heteroatoms selected from N, O, and S, substituted with 0-3 $R^{16}$;

$R^{5a}$ and $R^{5b}$, at each occurrence, are selected from H, $C_{1-6}$ alkyl, $(CH_2)_rC_{3-6}$ cycloalkyl, and phenyl;

$R^7$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_qSR^{7d}$, $(CH_2)_qNR^{7a}R^{7a}$, $(CH_2)_qC(O)OH$, $(CH_2)_qC(O)R^{7b}$, $(CH_2)_qC(O)NR^{7a}R^{7a}$, $(CH_2)_qNR^{7a}C(O)R^{7a}$, $(CH_2)_qNR^{7a}C(O)H$, $(CH_2)_qC(O)OR^{7b}$, $(CH_2)_qOC(O)R^{7b}$, $(CH_2)_qS(O)_pR^{7b}$, $(CH_2)_qS(O)_2NR^{7a}R^{7a}$, $(CH_2)_qNR^{7a}S(O)_2R^{7b}$, $C_{1-6}$ haloalkyl, a $(CH_2)_r$—$C_{3-10}$ carbocyclic residue substituted with 0-3 $R^{7c}$, and a $(CH_2)_r$-5-10 membered heterocyclic system containing 1-4 heteroatoms selected from N, O, and S, substituted with 0-2 $R^{7c}$;

$R^{7a}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is independently selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_r$ OH, $(CH_2)_rOC_{1-4}$ alkyl, $(CH_2)_rSC_{1-4}$ alkyl, $(CH_2)_rC(O)$ OH, $(CH_2)_rC(O)R^{7b}$, $(CH_2)_rC(O)NR^{7f}R^{7f}$, $(CH_2)_rNR^{7f}C(O)R^{7a}$, $(CH_2)_rOC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2 R^{7b}$, and $(CH_2)_r$phenyl substituted with 0-3 $R^{7e}$;

$R^{7d}$, at each occurrence, is independently selected from methyl, $CF_3$, $C_{2-6}$ alkyl substituted with 0-3 $R^{7e}$, alkenyl, alkynyl, and a $C_{3-10}$ carbocyclic residue substituted with 0-3 $R^{7c}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$ phenyl substituted with 0-3 $R^{8a}$;

$R^{8a}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{8f}R^{8f}$, and $(CH_2)_r$phenyl;

alternatively, $R^7$ and $R^8$ join to form $C_{3-7}$ cycloalkyl, or $=NR^{8b}$;

$R^{8b}$ is selected from H, $C_{1-6}$ alkyl, $C_{3-6}$ cycloalkyl, OH, CN, and $(CH_2)_r$-phenyl;

$R^{8f}$, at each occurrence, is independently selected from H, $C_{1-6}$ alkyl, and $C_{3-6}$ cycloalkyl;

$R^9$, is selected from H, $C_{1-6}$ alkyl, $C_{2-8}$ alkenyl, $C_{2-8}$ alkynyl, F, Cl, Br, I, $NO_2$, CN, (CHR')$_s$OH, (CHR')$_s$OR$^{9d}$, (CHR')$_r$ SR$^{9d}$, (CHR')$_s$NR$^{9a}$R$^{9a}$, (CHR')$_s$C(O)OH, (CHR')$_s$C(O) R$^{9b}$, (CHR')$_s$C(O)NR$^{9a}$R$^{9a}$, (CHR')$_s$NR$^{9a}$C(O)R$^{9b}$, (CHR')$_s$NR$^{9a}$C(O)H, (CHR')$_s$C(O)OR$^{9b}$, (CHR')$_s$OC(O) R$^{9b}$, (CHR')$_s$OC(O)NR$^{9a}$R$^{9a}$, (CHR')$_s$NR$^{9a}$C(O)OR$^{9b}$, (CHR')$_s$S(O)$_p$R$^{9b}$, (CHR')$_s$S(O)$_2$NR$^{9a}$R$^{9a}$, (CHR')$_s$NR$^{9a}$S (O)$_2$R$^{9b}$, $C_{1-6}$ haloalkyl, a (CHR')$_r$—$C_{3-10}$ carbocyclic residue substituted with 0-5 R$^{9c}$, and a (CHR')$_r$-5-10 membered heterocyclic system containing 1-4 heteroatoms selected from N, O, and S, substituted with 0-3 R$^{9c}$;

$R^{9a}$ at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 R$^{9e}$, and a $(CH_2)_r$-4-10 membered heterocyclic system containing 1-4 heteroatoms selected from N, O, and S, substituted with 0-3 R$^{9e}$;

alternatively, two $R^{9a}$s, along with the N to which they are attached, join to form a 5-6 membered heterocyclic system containing 1-2 heteroatoms selected from NR$^{9g}$, O, and S and optionally fused with a benzene ring or a 6-membered aromatic heterocycle;

$R^{9b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-2 R$^{9e}$, and a $(CH_2)_r$-4-6 membered heterocyclic system containing 1-4 heteroatoms selected from N, O, and S, substituted with 0-3 R$^{9e}$;

$R^{9c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_r$ OH, $(CH_2)_rOR^{9b}$, $(CH_2)_rSR^{9b}$, $(CH_2)_rC(O)OH$, $(CH_2)_rC(O)R^{9b}$, $(CH_2)_rC(O)NR^{9f}R^{9f}$, $(CH_2)_rNR^{9f}C(O)R^{9b}$, $(CH_2)_r C(O)OR^{9b}$, $(CH_2)_rOC(O)R^{9b}$, $(CH_2)_rC(=NR^{9f})NR^{9f}R^{9f}$, $(CH_2)_rS(O)_pR^{9b}$, $(CH_2)_rNHC(=NR^{9f})NR^{9f}R^{9f}$, $(CH_2)_rS(O)_2NR^{9f}R^{9f}$, $(CH_2)_rNR^{9f}S(O)_2R^{9b}$, and $(CH_2)_r$ phenyl substituted with 0-3 R$^{9e}$;

$R^{9d}$, at each occurrence, is independently selected from methyl, $CF_3$, $C_{2-6}$ alkyl residue substituted with 0-3 R$^{9e}$, $C_{3-6}$ alkenyl, $C_{3-6}$ alkynyl, a $C_{3-10}$ carbocyclic residue substituted with 0-3 R$^{9c}$, and a 5-6 membered heterocyclic system containing 1-4 heteroatoms selected from the group consisting of N, O, and S substituted with 0-3 R$^{9c}$;

$R^{9e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{9f}R^{9f}$;

$R^{9f}$, at each occurrence, is independently selected from H, $C_{1-6}$ alkyl, and $C_{3-6}$ cycloalkyl;

$R^{9g}$ is selected from H, $C_{1-6}$ alkyl, $C_{3-6}$ cycloalkyl, $(CH_2)_r$ phenyl, $C(O)R^{9f}$, $C(O)OR^{9h}$, and $SO_2R^{9h}$;

$R^{9h}$, at each occurrence, is independently selected from $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{10d}$, $(CH_2)_r$ $SR^{10d}$, $(CH_2)_rNR^{10a}R^{10a}$, $(CH_2)_rC(O)OH$, $(CH_2)_rC(O)$ $R^{10b}$, $(CH_2)_rC(O)NR^{10a}R^{10a}$, $(CH_2)_rNR^{10a}C(O)R^{10a}$, $(CH_2)_rNR^{10a}C(O)H$, $(CH_2)_rC(O)OR^{10b}$, $(CH_2)_rOC(O)$ $R^{10b}$, $(CH_2)_rOC(O)NR^{10a}R^{10a}$, $(CH_2)_rNR^{10a}C(O)OR^{10b}$, $(CH_2)_rS(O)_pR^{10b}$, $(CH_2)_rS(O)_2NR^{10a}R^{10a}$, $(CH_2)_r$ $NR^{10a}S(O)_2R^{10b}$, $C_{1-6}$ haloalkyl, a $(CH_2)_r$—$C_{3-10}$ carbocyclic residue substituted with 0-5 $R^{10c}$, and a $(CH_2)_r$-5-10 membered heterocyclic system containing 1-4 heteroatoms selected from N, O, and S, substituted with 0-3 $R^{10c}$;

$R^{10a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{10e}$, and a $(CH_2)_r$-4-10 membered heterocyclic system containing 1-4 heteroatoms selected from N, O, and S, substituted with 0-3 $R^{10e}$;

alternatively, two $R^{10a}$s, along with the N to which they are attached, join to form a 5-6 membered heterocyclic system containing 1-2 heteroatoms selected from $NR^{10g}$, O, and S and optionally fused with a benzene ring or a 6-membered aromatic heterocycle;

$R^{10b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{10e}$, and a $(CH_2)_r$-4-6 membered heterocyclic system containing 1-4 heteroatoms selected from N, O, and S, substituted with 0-3 $R^{10e}$;

$R^{10c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{10f}R^{10f}$, $(CH_2)_r$ OH, $(CH_2)_rOR^{10b}$, $(CH_2)_rSR^{10b}$, $(CH_2)_rC(O)OH$, $(CH_2)_r$ $C(O)R^{10b}$, $(CH_2)_rC(O)NR^{10f}R^{10f}$, $(CH_2)_rNR^{10f}C(O)R^{10a}$, $(CH_2)_rC(O)OR^{10b}$, $(CH_2)_rOC(O)R^{10b}$, $(CH_2)_rC(=NR^{10f})$ $NR^{10f}R^{10f}$, $(CH_2)_rS(O)_pR^{10b}$, $(CH_2)_rNHC(=NR^{10f})$ $NR^{10f}R^{10f}$, $(CH_2)_rS(O)_2NR^{10f}R^{10f}$, $(CH_2)_r$ $NR^{10f}S(O)_2$ $R^{10b}$, and $(CH_2)_r$phenyl substituted with 0-3 $R^{10e}$;

$R^{10d}$, at each occurrence, is independently selected from methyl, $CF_3$, $C_{2-6}$ alkyl substituted with 0-3 $R^{10e}$, $C_{3-6}$ alkenyl, $C_{3-6}$ alkynyl, and a $C_{3-10}$ carbocyclic residue substituted with 0-3 $R^{10c}$;

$R^{10e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, and $(CH_2)_r$phenyl;

$R^{10f}$, at each occurrence, is independently selected from H, $C_{1-6}$ alkyl, and $C_{3-6}$ cycloalkyl;

$R^{10g}$ is selected from H, $C_{1-6}$ alkyl, $C_{3-6}$ cycloalkyl, $(CH_2)_r$ phenyl, $C(O)R^{10f}$, $SO_2R^{10h}$, and $C(O)O R^{10h}$;

$R^{10h}$, at each occurrence, is independently selected from H, $C_{1-6}$ alkyl, $C_{3-6}$ cycloalkyl;

alternatively, $R^9$ and $R^{10}$ join to form =O, a $C_{3-10}$ cycloalkyl, a 5-6-membered lactone or lactam, or a 4-6-membered saturated heterocycle containing 1-2 heteroatoms selected from O, S, and $NR^{10g}$ and optionally fused with a benzene ring or a 6-membered aromatic heterocycle;

$R^{11}$, is selected from H, $C_{1-6}$ alkyl, $C_{2-8}$ alkenyl, $C_{2-8}$ alkynyl, $(CR'R')_qOH$, $(CH_2)_qSH$, $(CR'R')_qOR^{11d}$, $(CHR')_qSR^{11d}$, $(CR'R')_qNR^{11a}R^{11a}$, $(CHR')_rC(O)OH$, $(CHR')_rC(O)R^{11b}$, $(CHR')_rC(O)NR^{11a}R^{11a}$, $(CHR')_qNR^{11a}C(O)R^{11a}$, $(CHR')_qOC(O)NR^{11a}R^{11a}$, $(CHR')_qNR^{11a}C(O)OR^{11b}$, $(CHR')_qNR^{11a}C(O)NHR^{11a}$, $(CHR')_rC(O)OR^{11b}$, $(CHR')_q$ $OC(O)R^{11b}$, $(CHR')_rS(O)_pR^{11b}$, $(CHR')_rS(O)_2$ $NR^{11a}R^{11a}$, $(CHR')_qNR^{11a}S(O)_2R^{11b}$, $C_{1-6}$ haloalkyl, a $(CHR')_r$—$C_{3-10}$ carbocyclic residue substituted with 0-5 $R^{11c}$, and a $(R'R^{17})_r$-5-10 membered heterocyclic system containing 1-4 heteroatoms selected from N, O, and S, substituted with 0-3 $R^{11c}$;

$R^{11a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{11e}$, and a $(CH_2)_r$-5-10 membered heterocyclic system containing 1-4 heteroatoms selected from N, O, and S, substituted with 0-3 $R^{11e}$;

alternatively, two $R^{11a}$s, along with the N to which they are attached, join to form a 5-6 membered heterocyclic system containing 1-2 heteroatoms selected from $NR^{11g}$, O, and S and optionally fused with a benzene ring or a 6-membered aromatic heterocycle;

$R^{11b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{11e}$, and a $(CH_2)_r$-4-6 membered heterocyclic system containing 1-4 heteroatoms selected from N, O, and S, substituted with 0-3 $R^{11e}$;

$R^{11c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_r$ OH, $(CH_2)_rOC_{1-4}$ alkyl, $(CH_2)_rSC_{1-4}$ alkyl, $(CH_2)_rC(O)$ OH, $(CH_2)_rC(O)R^{11b}$, $(CH_2)_rC(O)NR^{11f}R^{11f}$, $(CH_2)_r$ $NR^{11f}C(O)R^{11a}$, $(CH_2)_rC(O)OC_{1-4}$ alkyl, $(CH_2)_rOC(O)$ $R^{11b}$, $(CH_2)_rC(=NR^{11f})NR^{11f}R^{11f}$, $(CH_2)_rNHC$ $(=NR^{11f})NR^{11f}R^{11f}$, $(CH_2)_rS(O)_pR^{11b}$, $(CH_2)_rS(O)_2$ $NR^{11f}R^{11f}$, $(CH_2)_rNR^{11f}S(O)_2R^{11b}$, and $(CH_2)_r$phenyl substituted with 0-3 $R^{11e}$;

$R^{11d}$, at each occurrence, is independently selected from methyl, $CF_3$, $C_{2-6}$ alkyl substituted with 0-3 $R^{11e}$, $C_{3-6}$ alkenyl, $C_{3-6}$ alkynyl, and a $C_{3-10}$ carbocyclic residue substituted with 0-3 $R^{11c}$;

$R^{11e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{11f}R^{11f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{11f}R^{11f}$;

$R^{11f}$, at each occurrence, is independently selected from H, $C_{1-6}$ alkyl, and $C_{3-6}$ cycloalkyl;

$R^{11g}$ is selected from H, $C_{1-6}$ alkyl, $C_{3-6}$ cycloalkyl, $(CH_2)_r$ phenyl, $C(O)R^{11f}$, $C(O)OR^{11h}$, and $SO_2R^{11h}$;

$R^{11h}$, at each occurrence, is independently selected from $C_{1-6}$ alkyl, and $C_{3-6}$ cycloalkyl;

$R^{12}$, is selected from H, $C_{1-6}$ alkyl, $C_{2-8}$ alkenyl, $C_{2-8}$ alkynyl, $(CHR')_qOH$, $(CH_2)_qSH$, $(CHR')_qOR^{12d}$, $(CH_2)_qSR^{12d}$, $(CHR')_qNR^{12a}R^{12a}$, $(CH_2)_rC(O)OH$, $(CH_2)_rC(O)R^{12b}$, $(CH_2)_rC(O)NR^{12a}R^{12a}$, $(CH_2)_qNR^{12a}C(O)R^{12a}$, $(CH_2)_r$ $OC(O)NR^{12a}R^{12a}$, $(CH_2)_rNR^{12a}C(O)OR^{12b}$, $(CH_2)_q$ $NR^{12a}C(O)NHR^{12a}$, $(CH_2)_rC(O)OR^{12b}$, $(CH_2)_qOC(O)$ $R^{12b}$, $(CH_2)_qS(O)_pR^{12b}$, $(CH_2)_qS(O)_2NR^{12a}R^{12a}$, $(CH_2)_q$ $NR^{12a}S(O)_2R^{12b}$, $C_{1-6}$ haloalkyl, a $(CH_2)_r$—$C_{3-10}$ carbocyclic residue substituted with 0-5 $R^{12c}$, and a $(CR'R^{17})_r$-5-10 membered heterocyclic system containing 1-4 heteroatoms selected from N, O, and S, substituted with 0-3 $R^{12c}$;

$R^{12a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{12e}$, and a $(CH_2)_r$-4-10 membered heterocyclic system containing 1-4 heteroatoms selected from N, O, and S, substituted with 0-3 $R^{12e}$;

alternatively, two $R^{12a}$s, along with the N to which they are attached, join to form a 5-6 membered heterocyclic system containing 1-2 heteroatoms selected from $NR^{12g}$, O, and S and optionally fused with a benzene ring or a 6-membered aromatic heterocycle;

$R^{12b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{12e}$, and a $(CH_2)_r$-4-6 membered heterocyclic system containing 1-4 heteroatoms selected from N, O, and S, substituted with 0-3 $R^{12e}$;

$R^{12c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{12f}R^{12f}$, $(CH_2)_r$OH, $(CH_2)_rOC_{1-4}$ alkyl, $(CH_2)_rSC_{1-4}$ alkyl, $(CH_2)_rC(O)$OH, $(CH_2)_rC(O)R^{12b}$, $(CH_2)_rC(O)NR^{12f}R^{12f}$, $(CH_2)_rNR^{12f}C(O)R^{12a}$, $(CH_2)_rC(O)OC_{1-4}$ alkyl, $(CH_2)_rOC(O)R^{12b}$, $(CH_2)_rC(=NR^{12f})NR^{12f}R^{12f}$, $(CH_2)_rNHC(=NR^{12f})NR^{12f}R^{12f}$, $(CH_2)_rS(O)_pR^{12b}$, $(CH_2)_rS(O)_2NR^{12f}R^{12f}$, $(CH_2)_rNR^{12f}S(O)_2R^{12b}$, and $(CH_2)_r$phenyl substituted with 0-3 $R^{12e}$;

$R^{12d}$, at each occurrence, is independently selected from methyl, $CF_3$, $C_{2-6}$ alkyl substituted with 0-3 $R^{12e}$, $C_{3-6}$ alkenyl, $C_{3-6}$ alkynyl, and a $C_{3-10}$ carbocyclic residue substituted with 0-3 $R^{12c}$;

$R^{12e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{12f}R^{12f}$, and $(CH_2)_r$phenyl;

$R^{12f}$, at each occurrence, is independently selected from H, $C_{1-6}$ alkyl, and $C_{3-6}$ cycloalkyl;

$R^{12g}$ is selected from H, $C_{1-6}$ alkyl, $C_{3-6}$ cycloalkyl, $(CH_2)_r$phenyl, $C(O)R^{12f}$, $C(O)OR^{12h}$, and $SO_2R^{12h}$;

$R^{12h}$, at each occurrence, is independently selected from $C_{1-6}$ alkyl, and $C_{3-6}$ cycloalkyl;

alternatively, $R^{11}$ and $R^{12}$ join to form a $C_{3-10}$ cycloalkyl, a 5-6-membered lactone or lactam, or a 4-6-membered saturated heterocycle containing 1-2 heteroatoms selected from O, S, and $NR^{11g}$ and optionally fused with a benzene ring or a 6-membered aromatic heterocycle;

$R^{13}$, at each occurrence, is independently selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_qNR^{13a}R^{13a}$, $(CHR')_qOH$, $(CH_2)_qOR^{13b}$, $(CH_2)_q$ SH, $(CH_2)_qSR^{13b}$, $(CH_2)_wC(O)OH$, $(CH_2)_wC(O)R^{13b}$, $(CH_2)_wC(O)NR^{13a}R^{13a}$, $(CH_2)_wNR^{13d}C(O)R^{13a}$, $(CH_2)_w$ $C(O)OR^{13b}$, $(CH_2)_qOC(O)R^{13b}$, $(CH_2)_wS(O)_pR^{13b}$, $(CH_2)_wS(O)_2NR^{13a}R^{13a}$, $(CH_2)_qNR^{13d}S(O)_2R^{13b}$, and $(CH_2)_w$-phenyl substituted with 0-3 $R^{13c}$;

$R^{13a}$, at each occurrence, is independently selected from H, $C_{1-6}$ alkyl, $C_{3-6}$ cycloalkyl, and phenyl substituted with 0-3 $R^{13c}$;

$R^{13b}$, at each occurrence, is independently selected from $C_{1-6}$ alkyl, $C_{3-6}$ cycloalkyl, and phenyl substituted with 0-3 $R^{13c}$;

$R^{13c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is independently selected from H, $C_{1-6}$ alkyl, and $C_{3-6}$ cycloalkyl;

$R^{14}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a}$, $(CHR')_rOH$, $(CHR')_rO(CHR')_rR^{14d}$, $(CHR')_rSH$, $(CHR')_rC(O)H$, $(CHR')_rS(CHR')_rR^{14d}$, $(CHR')_rC(O)OH$, $(CHR')_rC(O)$ $(CHR')_rR^{14b}$, $(CHR')_rC(O)NR^{14a}R^{14a}$, $(CHR')_rNR^{14f}C(O)$ $(CHR')_rR^{14b}$, $(CHR')_rOC(O)NR^{14a}R^{14a}$, $(CHR')_rNR^{14f}C(O)O(CHR')_rR^{14b}$, $(CHR')_rC(O)O(CHR')_rR^{14d}$, $(CHR')_rOC(O)$ $(CHR')_rR^{14b}$, $(CHR')_rC(=NR^{14f})NR^{14a}R^{14a}$, $(CHR')_rNHC(=NR^{14f})NR^{14f}R^{14f}$, $(CHR')_rS(O)_p(CHR')_rR^{14b}$, $(CHR')_rS(O)_2NR^{14a}R^{14a}$, $(CHR')_rNR^{14f}S(O)_2(CHR')_rR^{14b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{14e}$, and a $(CH_2)_r$ -4-10 membered heterocyclic system containing 1-4 heteroatoms selected from N, O, and S, substituted with 0-2 $R^{15e}$, or two $R^{14}$ substituents on adjacent atoms on ring A form to join a 5-6 membered heterocyclic system containing 1-3 heteroatoms selected from N, O, and S substituted with 0-2 $R^{15e}$;

$R^{14a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{14e}$, and a $(CH_2)_r$-4-10 membered heterocyclic system containing 1-4 heteroatoms selected from N, O, and S, substituted with 0-2 $R^{14e}$;

$R^{14b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{14e}$, and $(CH_2)_r$-4-6 membered heterocyclic system containing 1-4 heteroatoms selected from N, O, and S, substituted with 0-2 $R^{14e}$;

$R^{14d}$, at each occurrence, is independently selected from $C_{3-8}$ alkenyl, $C_{3-8}$ alkynyl, methyl, $CF_3$, $C_{2-6}$ alkyl substituted with 0-3 $R^{14e}$, a $(CH_2)_r$—$C_{3-10}$ carbocyclic residue substituted with 0-3 $R^{14e}$, and a $(CH_2)_r$4-6 membered heterocyclic system containing 1-4 heteroatoms selected from N, O, and S, substituted with 0-3 $R^{14e}$;

$R^{14e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{14f}R^{14f}$, and $(CH_2)_r$phenyl;

$R^{14f}$, at each occurrence, is independently selected from H, $C_{1-6}$ alkyl, $C_{3-6}$ cycloalkyl, and phenyl;

$R^{15}$, at each occurrence, is independently selected from $C_{1-8}$ alkyl, $(CH_2)_rC_{3-6}$ cycloalkyl, Cl, Br, I, F, $NO_2$, CN, $(CR'R')_rNR^{15a}R^{15a}$, $(CR'R')_rOH$, $(CR'R')_rO(CHR')_rR^{15d}$, $(CR'R')_r$ SH, $(CR'R')_rC(O)H$, $(CR'R')_rS(CHR')_rR^{15d}$, $(CR'R')_rC(O)OH$, $(CR'R')_rC(O)$ $(CHR')_rR^{15b}$, $(CR'R')_rC(O)NR^{15a}R^{15a}$, $(CR'R')_rNR^{15f}C(O)$ $(CHR')_rR^{15b}$, $(CR'R')_rOC(O)NR^{15a}R^{15a}$, $(CR'R')_rNR^{15f}C(O)O(CHR')_rR^{15b}$, $(CR'R')_rNR^{15f}C(O)NR^{15f}R^{15f}$, $(CR'R')_rC(O)O(CHR')_rR^{15d}$, $(CR'R')_rOC(O)$ $(CHR')_rR^{15b}$, $(CR'R')_rC(=NR^{15f})NR^{15a}R^{15a}$, $(CR'R')_rNHC(=NR^{15f})NR^{15f}R^{15f}$, $(CR'R')_rS(O)_p(CHR')_rR^{15b}$, $(CR'R')_rS(O)_2NR^{15a}R^{15a}$, $(CR'R')_rNR^{15f}S(O)_2(CHR')_rR^{15b}$, $C_{1-6}$ haloalkyl, $C_{2-8}$ alkenyl substituted with 0-3 R', $C_{2-8}$ alkynyl substituted with 0-3 R', $(CR'R')_r$phenyl substituted with 0-3 $R^{15e}$, and a $(CH_2)_r$ -5-10 membered heterocyclic system containing 1-4 heteroatoms selected from N, O, and S, substituted with 0-2 $R^{15e}$;

$R^{15a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

alternatively, two $R^{15a}$s, along with the N to which they are attached, join to form a 5-6 membered heterocyclic system containing 1-2 heteroatoms selected from $NR^{15h}$, O, and S and optionally fused with a benzene ring or a 6-membered aromatic heterocycle;

$R^{15b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{15e}$, and $(CH_2)_r$-5-6 membered heterocyclic system containing 1-4 heteroatoms selected from N, O, and S, substituted with 0-2 $R^{15e}$;

$R^{15d}$, at each occurrence, is independently selected from $C_{3-8}$ alkenyl, $C_{3-8}$ alkynyl, methyl, $CF_3$, $C_{2-6}$ alkyl substituted with 0-3 $R^{15e}$, a $(CH_2)_r$—$C_{3-10}$ carbocyclic residue substituted with 0-3 $R^{15e}$, and a $(CH_2)_r$-5-6 membered heterocyclic system containing 1-4 heteroatoms selected from N, O, and S, substituted with 0-3 $R^{15e}$;

$R^{15e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, $(CH_2)_r$phenyl, and a heterocycle substituted with 0-1 $R^{15g}$, wherein the heterocycle is selected from imidazole, thiazole, oxazole, pyrazole, 1,2,4-triazole, 1,2,3-triazole, isoxazole, and tetrazole;

$R^{15f}$, at each occurrence, is independently selected from H, $C_{1-6}$ alkyl, $C_{3-6}$ cycloalkyl, and phenyl;

$R^{15g}$ is selected from methyl, ethyl, acetyl, and $CF_3$;

$R^{15h}$ is selected from H, $C_{1-6}$ alkyl, $C_{3-6}$ cycloalkyl, $(CH_2)_r$phenyl, $C(O)R^{15f}$, $C(O)OR^{15i}$, and $SO_2R^{15i}$;

$R^{15i}$, at each occurrence, is independently selected from $C_{1-6}$ alkyl, $C_{3-6}$ cycloalkyl;

$R^{16}$, at each occurrence, is independently selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a}$, $(CHR')_rNR^{16f}S(O)_2(CHR')_rR^{16b}$, $C_{1-6}$ haloalkyl, $C_{2-8}$ alkenyl substituted with 0-3 R', $C_{2-8}$ alkynyl substituted with 0-3 R', and $(CHR')_r$phenyl substituted with 0-3 $R^{16e}$;

$R^{16a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a $(CH_2)_r$-5-10 membered heterocyclic system containing 1-4 heteroatoms selected from N, O, and S, substituted with 0-2 $R^{16e}$; $R^{16b}$, at each occurrence, is independently selected from $C_{1-6}$ alkyl, $C_{3-8}$ alkenyl, $C_{3-8}$ alkynyl, a $(CH_2)_rC_{3-6}$ carbocyclic residue substituted with 0-3 $R^{16e}$, and a $(CH_2)_r$-5-6 membered heterocyclic system containing 1-4 heteroatoms selected from N, O, and S, substituted with 0-2 $R^{16e}$;

$R^{16d}$, at each occurrence, is independently selected from $C_{3-8}$ alkenyl, $C_{3-8}$ alkynyl, methyl, $CF_3$, $C_{2-6}$ alkyl substituted with 0-3 $R^{16e}$, a $(CH_2)_r$—$C_{3-10}$ carbocyclic residue substituted with 0-3 $R^{16e}$, and a $(CH_2)_r$-5-6 membered heterocyclic system containing 1-4 heteroatoms selected from N, O, and S, substituted with 0-3 $R^{16e}$;

$R^{16e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is independently selected from H, $C_{1-5}$ alkyl, and $C_{3-6}$ cycloalkyl, and phenyl;

R', at each occurrence, is independently selected from H, $C_{1-6}$ alkyl, $C_{2-8}$ alkenyl, $C_{2-8}$ alkynyl, $(CH_2)_rC_{3-6}$ cycloalkyl, and $(CH_2$ substituted with $R^e$;

$R^e$ is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^fR^f$, and $(CH_2)_r$phenyl;

$R^f$ is selected from H, $C_{1-5}$ alkyl, and $C_{3-6}$ cycloalkyl, and phenyl;

$R^{18}$, at each occurrence, is independently selected from H, $C_{1-6}$ alkyl, $C_{3-6}$ alkenyl, $C_{3-6}$ alkynyl, $C(O)$—$C_{3-6}$ alkyl, $C(O)$—$C_{3-6}$ alkenyl, $C(O)$—$C_{3-6}$ alkynyl, $(CH_2)_rC_{3-6}$ cycloalkyl, and $(CH_2)_r$phenyl substituted with $R^e$;

$R^{19}$ is absent, taken with the nitrogen to which it is attached to form an N-oxide, or selected from $C_{1-8}$ alkyl, $C_{2-8}$ alkenyl, $C_{2-8}$ alkynyl, $(CH_2)_qC_{3-6}$ cycloalkyl, $(CH_2)_qC(O)R^{19b}$, $(CH_2)_qC(O)NR^{19a}R^{19a}$, $(CH_2)_qC(O)OR^{19b}$, and a $(CH_2)_r$—$C_{3-10}$ carbocyclic residue substituted with 0-3 $R^{19c}$;

$R^{19a}$, at each occurrence, is selected from H, $C_{1-6}$ alkyl, $(CH_2)_r$ $C_{3-6}$ cycloalkyl, and phenyl;

$R^{19b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R^{19c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{19a}R^{19a}$, and $(CH_2)_r$phenyl;

alternatively, $R^{19}$ joins with $R^7$, $R^9$, or $R^{11}$ to form a 5, 6 or 7 membered piperidinium spirocycle or pyrrolidinium spirocycle substituted with 0-3 $R^a$;

g is selected from 0, 1, 2, and 3;
v is selected from 0, 1, and 2;
t is selected from 1 and 2;
w is selected from 0 and 1;
r is selected from 0, 1, 2, 3, 4, and 5;
q is selected from 1, 2, 3, 4, and 5; and
p is selected from 0, 1, and 2.

In another embodiment, the present invention provides compounds of formula (I), wherein
ring D is selected from

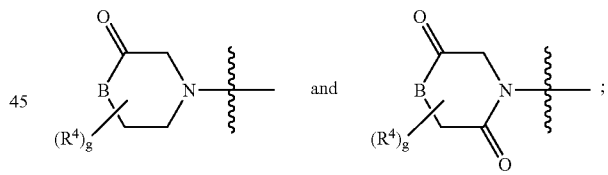

Z is selected from O, S, N(CN), and $N(CONH_2)$;
$R^1$ and $R^2$ are independently selected from H and $C_{1-4}$ alkyl;
$R^{19}$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0-3 $R^{19c}$;
$R^{19c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{19a}R^9$, and $(CH_2)_r$phenyl;
alternatively, $R^{19}$ joins with $R^7$, $R^9$, or $R^{11}$ to form a 5, 6 or 7 membered piperidinium spirocycle or pyrrolidinium spirocycle substituted with 0-3 $R^a$;
$R^{13}$, at each occurrence, is independently selected from $C_{1-4}$ alkyl, $C_{3-6}$ cycloalkyl, $(CH_2)NR^{13a}R^{13a}$, $(CHR')OH$, $(CH_2)OR^{13b}$, $(CH_2)_wC(O)R^{13b}$, $(CH_2)_wC(O)NR^{13a}R^{13a}$, $(CH_2)NR^{13d}C(O)R^{13a}$, $(CH_2)_wS(O)_2NR^{13a}R^{13a}$, $(CH_2)NR^{13d}S(O)_2R^{13b}$, and $(CH_2)_w$-phenyl substituted with 0-3 $R^{13c}$;

$R^{13a}$, at each occurrence, is independently selected from H, $C_{1-6}$ alkyl, $C_{3-6}$ cycloalkyl, and phenyl substituted with 0-3 $R^{13c}$;

$R^{13b}$, at each occurrence, is independently selected from $C_{1-6}$ alkyl, $C_{3-6}$ cycloalkyl, and phenyl substituted with 0-3 $R^{13c}$;

$R^{13c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, and $(CH_2)_rNR^{13d}R^{13d}$;

$R^{13d}$, at each occurrence, is independently selected from H, $C_{1-6}$ alkyl, and $C_{3-6}$ cycloalkyl;

q is selected from 1, 2, and 3; and r is selected from 0, 1, 2, and 3.

In another embodiment, the present invention provides compounds of formula (I), wherein E is —(C=O)—$(CR^9R^{10})_v$—$(CR^{11}R^{12})$—, —$(CR^7R^8)$—$(CR^9R^{10})_v$—$(CR^{11}R^{12})$,

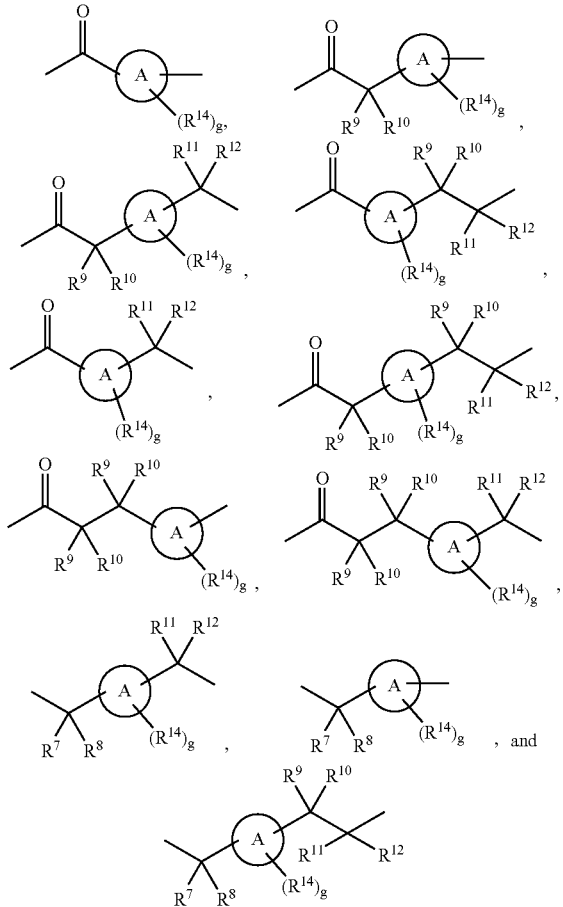

$R^3$ is selected from a $(CR^{3a}H)_r$—$C_{3-8}$ carbocyclic residue substituted with 0-5 $R^{15}$, wherein the carbocyclic residue is selected from phenyl, $C_{3-6}$ cycloalkyl, naphthyl, and adamantyl; and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^{5a}H)_r$-phenyl substituted with 0-5 $R^{16}$; and a $(CR^{5a}H)_r$-heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides compounds of formula (I), wherein B is selected from O and $NR^{17}$.

E is —$(CR^7R^8)$—$(CR^9R^{10})_v$—$(CR^{11}R^{12})$

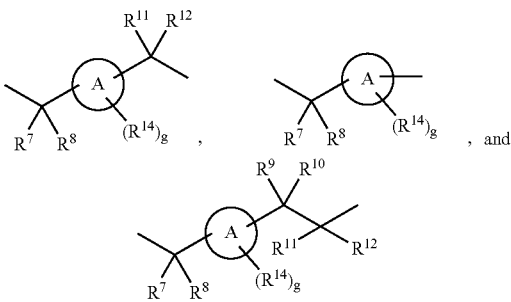

$R^1$ and $R^2$ are H;

$R^{16}$, at each occurrence, is independently selected from $C_{1-8}$ alkyl, $(CH_2)_rC_{3-6}$ cycloalkyl, $CF_3$, Cl, Br, I, F, $(CH_2)_r$ $NR^{16a}R^{16a}$, $NO_2$, CN, OH, $(CH_2)_rOR^{16d}$, $(CH_2)_rC(O)R^{16b}$, $(CH_2)_rC(O)NR^{16a}R^{16a}$, $(CH_2)_rNR^{16f}C(O)R^{16b}$, $(CH_2)_rS(O)_pR^{16b}$, $(CH_2)_rS(O)_2NR^{16a}R^{16a}$, $(CH_2)_rNR^{16f}S(O)_2R^{16b}$, and $(CH_2)_r$phenyl substituted with 0-3 $R^{16e}$;

$R^{16a}$, at each occurrence, is independently selected from H, $C_{1-6}$ alkyl, $C_{3-6}$ cycloalkyl, and $(CH_2)_r$phenyl substituted with 0-3 $R^{16e}$;

$R^{16b}$, at each occurrence, is independently selected from $C_{1-6}$ alkyl, $C_{3-6}$ cycloalkyl, and $(CH_2)_r$phenyl substituted with 0-3 $R^{16e}$;

$R^{16d}$, at each occurrence, is independently selected from $C_{1-6}$ alkyl and phenyl;

$R^{16e}$, at each occurrence, is independently selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is independently selected from H, and $C_{1-5}$ alkyl.

In another embodiment, the present invention provides compounds of formula (I), wherein E is —$(CR^7R^8)$—$(CR^9R^{10})_n$—$(CR^{11}R^{12})$ B is selected from $NR^{17}$ or O;

$R^5$ is $CH_2$phenyl substituted with 0-3 $R^{16}$; and r is selected from 0, 1, and 2.

In another embodiment, the present invention provides compounds of formula (I), wherein Z is selected from O, N(CN) and $NC(O)NH_2$; and $R^4$ is selected from H and $R^5$.

In another embodiment, the present invention provides compounds of formula (I), wherein $R^3$ is a $C_{3-10}$ carbocyclic residue substituted with 0-3 $R^{15}$, wherein the carbocyclic residue is selected from cyclopropyl, cyclopentyl, cyclohexyl, phenyl, naphthyl and adamantyl, and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is independently selected from $C_{1-8}$ alkyl, $(CH_2)_rC_{3-6}$ cycloalkyl, $CF_3$, Cl, Br, I, F, $(CH_2)_r NR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_r$, $S(O)_pR^{15b}$, $(CH_2)_rS(O)_2NR^{15a}R^{15a}$, $(CH_2)_r NR^{15f}S(O)_2 R^{15b}$, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, is independently selected from H, $C_{1-6}$ alkyl, $C_{3-6}$ cycloalkyl, and $(CH_2)_r$phenyl substituted with 0-3 $R^{15e}$;

alternatively, two $R^{15a}$s, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is independently selected from H, $C_{1-6}$ alkyl, $C_{3-6}$ cycloalkyl, and $(CH_2)_r$phenyl substituted with 0-3 $R^{15e}$;

$R^{15d}$, at each occurrence, is independently selected from $C_{1-6}$ alkyl and phenyl;

$R^{15e}$, at each occurrence, is independently selected from $C_{1-6}$ alkyl, Cl, F, Br, I, CN, $NO_2$, $(CF_2)_rCF_3$, OH, and $(CH_2)_r OC_{1-5}$ alkyl; and $R^{15f}$, at each occurrence, is independently selected from H, and $C_{1-5}$ alkyl.

In another embodiment, the present invention provides compounds of formula (I), wherein
Z is O, N(CN), and $NC(O)NH_2$;
E is

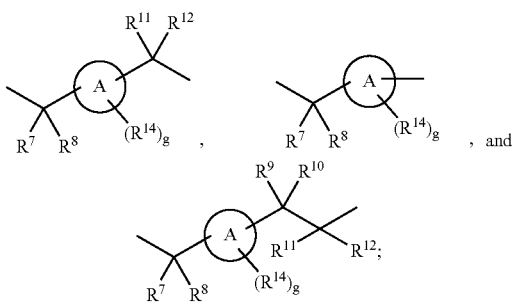

B is $NR^{17}$ or 0;
$R^5$ is $CH_2$phenyl substituted with 0-3 $R^{16}$; and
r is selected from 0, 1, and 2.

In another embodiment, the present invention provides compounds of formula (I), wherein
Z is selected from O, N(CN) and $NC(O)NH_2$;
$R^3$ is a $C_{3-10}$ carbocyclic residue substituted with 0-3 $R^{15}$, wherein the carbocyclic residue is selected from cyclopropyl, cyclobutyl, cyclopentyl, cyclohexyl, phenyl, naphthyl and adamantyl, and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, iso-quinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{15}$, at each occurrence, is independently selected from $C_{1-8}$ alkyl, $(CH_2)_rC_{3-6}$ cycloalkyl, $CF_3$, Cl, Br, I, F, $(CH_2)_r NR^{15a}R^{15a}$, $NO_2$, CN, OH, $(CH_2)_rOR^{15d}$, $(CH_2)_rC(O) R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_r$, $S(O)_pR^{15b}$, $(CH_2)_rS(O)_2NR^{15a}R^{15a}$, $(CH_2)_r NR^{15f}S(O)_2 R^{15b}$, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, is independently selected from H, $C_{1-6}$ alkyl, $C_{3-6}$ cycloalkyl, and $(CH_2)_r$phenyl substituted with 0-3 $R^{15e}$;

alternatively, two $R^{15a}$s, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is independently selected from H, $C_{1-6}$ alkyl, $C_{3-6}$ cycloalkyl, and $(CH_2)_r$phenyl substituted with 0-3 $R^{15e}$;

$R^{15d}$, at each occurrence, is independently selected from $C_{1-6}$ alkyl and phenyl;

$R^{15e}$, at each occurrence, is independently selected from $C_{1-6}$ alkyl, Cl, F, Br, I, CN, $NO_2$, $(CF_2)_rCF_3$, OH, and $(CH_2)_r OC_{1-5}$ alkyl; and $R^{15f}$, at each occurrence, is independently selected from H, and $C_{1-5}$ alkyl.

In another embodiment, the present invention provides compounds of formula (I), wherein
E is

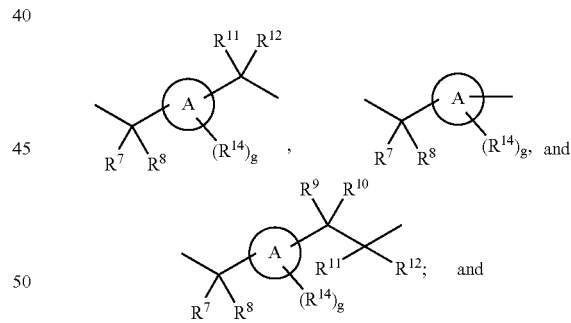

A is selected from cyclopropyl, cyclobutyl, cyclopentyl, cyclohexyl, and phenyl.

In another embodiment, the present invention provides compounds of formula (I), wherein
E is selected from (C=O)—$(CR^9R^{10})_v$—$(CR^{11}R^{12})$—,

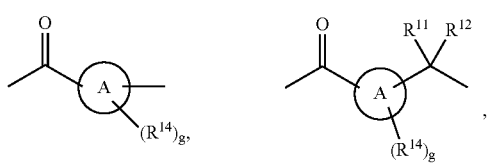

-continued

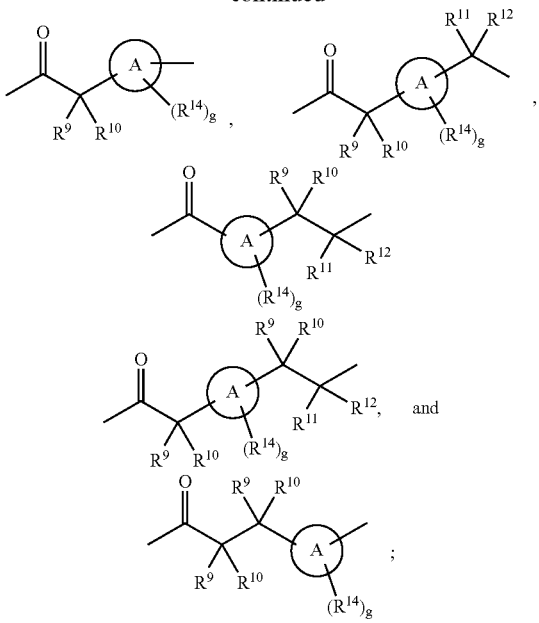

R³ is a C_{3-10} carbocyclic residue substituted with 0-3 R¹⁵, wherein the carbocyclic residue is selected from cyclopropyl, cyclobutyl, cyclopentyl, cyclohexyl, phenyl, naphthyl and adamantyl, and a (CR³ᵃH)_r-heterocyclic system substituted with 0-3 R¹⁵, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides compounds of formula (I), wherein
E is (C=O)—(CR⁹R¹⁰)_v—(CR¹¹R¹²)—.

In another embodiment, the present invention provides compounds of formula (I), wherein
E is

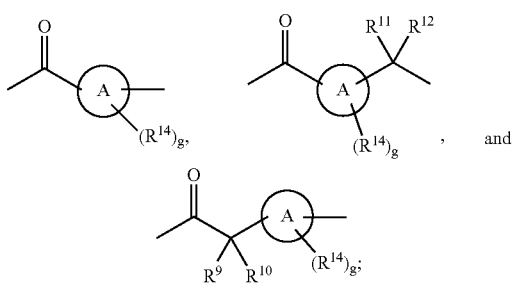

A is selected from cyclopropyl, cyclobutyl, cyclopentyl cyclohexyl, and phenyl.

In another embodiment, the present invention provides compounds of formula (I), wherein
R⁹, is selected from H, C_{1-6} alkyl, C_{2-8} alkenyl, C_{2-8} alkynyl, F, Cl, Br, I, NO_2, CN, (CHR')_rOH, (CH_2)_rOR⁹ᵈ, (CH_2)_rSR⁹ᵈ, (CH_2)_rNR⁹ᵃR⁹ᵃ, (CH_2)_rC(O)OH, (CH_2)_rC(O)R⁹ᵇ, (CH_2)_rC(O)NR⁹ᵃR⁹ᵃ, (CH_2)_rNR⁹ᵃC(O)R⁹ᵇ, (CH_2)_r NR⁹ᵃC(O)H, C_{1-6} haloalkyl, a (CH_2)_r—C_{3-10} carbocyclic residue substituted with 0-5 R⁹ᶜ, and a (CH_2)_r-5-10 membered heterocyclic system containing 1-4 heteroatoms selected from N, O, and S, substituted with 0-3 R⁹ᶜ;

R⁹ᵃ, at each occurrence, is independently selected from H, C_{1-6} alkyl, C_{3-8} alkenyl, C_{3-8} alkynyl, a (CH_2)_r—C_{3-10} carbocyclic residue substituted with 0-5 R⁹ᵉ, and a (CH_2)_r-4-10 membered heterocyclic system containing 1-4 heteroatoms selected from N, O, and S, substituted with 0-3 R⁹ᵉ;

alternatively, two R⁹ᵃs, along with the N to which they are attached, join to form a 5-6 membered heterocyclic system containing 1-2 heteroatoms selected from NR⁹ᵍ, O, and S and optionally fused with a benzene ring or a 6-membered aromatic heterocycle;

R¹⁰, is selected from H, C_{1-6} alkyl, C_{2-8} alkenyl, C_{2-8} alkynyl, F, Cl, Br, I, NO_2, CN, (CHR')_rOH, (CH_2)_rOR¹⁰ᵈ, (CH_2)_rSR¹⁰ᵈ, (CH_2)_rNR¹⁰ᵃR¹⁰ᵃ;

alternatively, R⁹ and R¹⁰ join to form =O, a C_{3-10} cycloalkyl, a 5-6-membered lactone or lactam, or a 4-6-membered saturated heterocycle containing 1-2 heteroatoms selected from O, S, and NR¹⁰ᵍ and optionally fused with a benzene ring or a 6-membered aromatic heterocycle;

R¹¹, is selected from H, C_{1-6} alkyl, C_{2-8} alkenyl, C_{2-8} alkynyl, (CR'R¹⁷)_qOH, (CH_2)_qSH, (CR'R¹⁷)_qOR¹¹ᵈ, (CH_2)_qSR¹¹ᵈ;

R¹², is selected from H, C_{1-6} alkyl, C_{2-8} alkenyl, C_{2-8} alkynyl, (CHR')_qOH, (CH_2)_qSH, (CHR')_qOR¹²ᵈ, (CH_2)_qSR¹²ᵈ, (CHR')_qNR¹²ᵃR¹²ᵃ; and R¹⁴, at each occurrence, is independently selected from H, C_{1-6} alkyl, C_{2-8} alkenyl, C_{2-8} alkynyl, (CH_2)_rC_{3-6} cycloalkyl, Cl, Br, I, F, NO_2, CN, (CHR')_rNR¹⁴ᵃR¹⁴ᵃ, (CHR')_rOH, (CHR')_rO(CHR')_rR¹⁴ᵈ, (CHR')_rSH, (CHR')_rC(O)H, (CHR')_rS(CHR')_rR¹⁴ᵈ.

In another embodiment, the present invention provides compounds of formula (I), wherein ring D is selected from

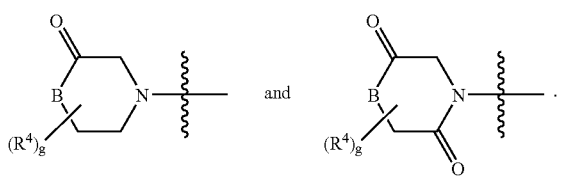

In another embodiment, the present invention provides compounds of formula (I), wherein Z is selected from O, S, N(CN), and N(CONH_2).

In another embodiment, the present invention provides compounds of formula (I), wherein Z is selected from O, N(CN) and NC(O)NH_2.

In another embodiment, the present invention provides compounds of formula (I), wherein Z is O.

In another embodiment, the present invention provides compounds of formula (I), wherein R¹ and R² are independently selected from H and C_{1-4} alkyl.

In another embodiment, the present invention provides compounds of formula (I), wherein R¹ and R² are H.

In another embodiment, the present invention provides compounds of formula (I), wherein R¹⁹ is absent, taken with the nitrogen to which it is attached to form an N-oxide, or selected from C_{1-8} alkyl, (CH_2)_rC_{3-6} cycloalkyl, and (CH_2)_r-phenyl substituted with 0-3 R¹⁹ᶜ; R¹⁹ᶜ, at each occurrence, is selected from C_{1-6} alkyl, C_{2-8} alkenyl, C_{2-8} alkynyl, C_{3-6} cycloalkyl, Cl, F, Br, I, CN, NO_2, (CF_2)_rCF_3, (CH_2)_rOC_{1-5} alkyl, (CH_2)_rOH, (CH_2)_rSC_{1-5} alkyl, (CH_2)_rNR¹⁹ᵃR⁹, and (CH_2)_r phenyl; alternatively, R¹⁹ joins with R⁷, R⁹, or R¹¹ to form a 5, 6 or 7 membered piperidinium spirocycle or pyrrolidinium spirocycle substituted with 0-3 $R^a$.

In another embodiment, the present invention provides compounds of formula (I), wherein $R^{19}$ is absent.

In another embodiment, the present invention provides compounds of formula (I), wherein $R^{13}$, at each occurrence, is independently selected from $C_{1-4}$ alkyl, $C_{3-6}$ cycloalkyl, $(CH_2)NR^{13a}R^{13a}$, $(CHR')OH$, $(CH_2)OR^{13b}$, $(CH_2)_wC(O)R^{13b}$, $(CH_2)_wC(O)NR^{13a}R^{13a}$, $(CH_2)NR^{13d}C(O)R^{13a}$, $(CH_2)_w S(O)_2NR^{13a}R^{13a}$, $(CH_2)NR^{13d}S(O)_2R^{13b}$, and $(CH_2)_w$-phenyl substituted with 0-3 $R^{13c}$; $R^{13a}$, at each occurrence, is independently selected from H, $C_{1-6}$ alkyl, $C_{3-6}$ cycloalkyl, and phenyl substituted with 0-3 $R^{13c}$; $R^{13b}$, at each occurrence, is independently selected from $C_{1-6}$ alkyl, $C_{3-6}$ cycloalkyl, and phenyl substituted with 0-3 $R^{13c}$; $R^{13c}$, at each occurrence, is independently selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rOH$, and $(CH_2)_rNR^{13d}R^{13d}$; $R^{13d}$, at each occurrence, is independently selected from H, $C_{1-6}$ alkyl, and $C_{3-6}$ cycloalkyl.

In another embodiment, the present invention provides compounds of formula (I), wherein E is —(C=O)—$(CR^9R^{10})_v$—$(CR^{11}R^{12})$—, —$(CR^7R^8)$—$(CR^9R^{10})_v$—$(CR^{11}R^{12})$,

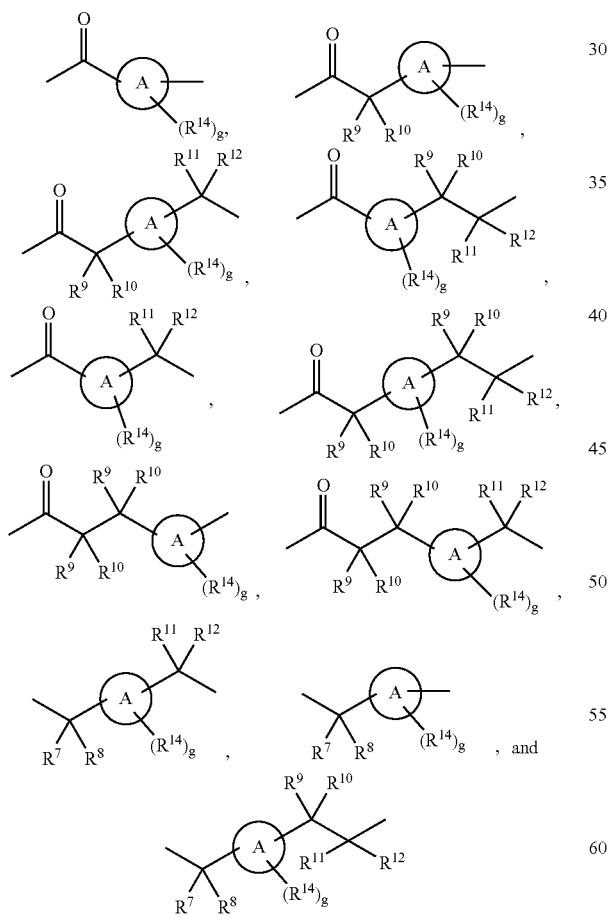

In another embodiment, the present invention provides compounds of formula (I), wherein E is —$(CR^7R^8)$—$(CR^9R^{10})_n$—$(CR^{11}R^{12})$.

In another embodiment, the present invention provides compounds of formula (I), wherein E is

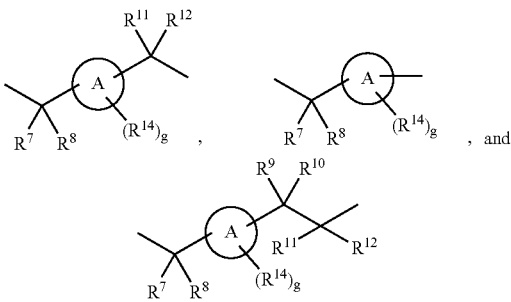

In another embodiment, the present invention provides compounds of formula (I), wherein E is (C=O)—$(CR^9R^{10})_v$—$(CR^{11}R^{12})$—.

In another embodiment, the present invention provides compounds of formula (I), wherein E is

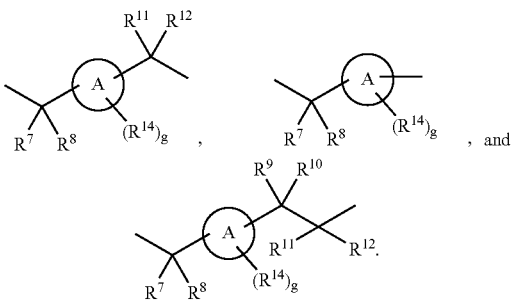

In another embodiment, the present invention provides compounds of formula (I), wherein E is

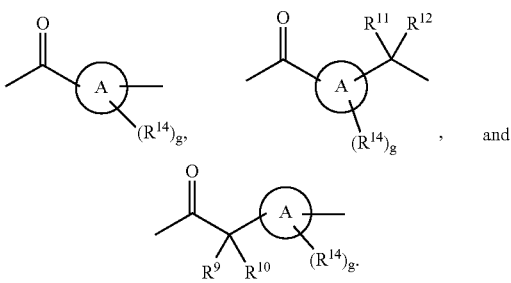

In another embodiment, the present invention provides compounds of formula (I), wherein E is

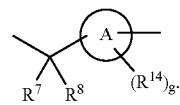

In another embodiment, the present invention provides compounds of formula (I), wherein $R^3$ is selected from a $(CR^{3a}H)_r$—$C_{3-8}$ carbocyclic residue substituted with 0-5 $R^{15}$, wherein the carbocyclic residue is selected from phenyl, $C_{3-6}$ cycloalkyl, naphthyl, and adamantyl; and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, indazolyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides compounds of formula (I), wherein $R^3$ is selected from a $(CR^{3a}H)_r$—$C_{3-8}$ carbocyclic residue substituted with 0-5 $R^{15}$, wherein the carbocyclic residue is phenyl; and a $(CR^{3a}H)_r$-heterocyclic system substituted with 0-3 $R^{15}$, wherein the heterocyclic system is selected from indazolyl, indolinyl, indazolyl, isoindolyl, isothiadiazolyl, isoxazolyl, and thiazolyl.

In another embodiment, the present invention provides compounds of formula (I), wherein $R^3$ is selected from a $C_{3-8}$ carbocyclic residue substituted with 0-5 $R^{15}$, wherein the carbocyclic residue is phenyl; and a heterocyclic system substituted with 0-3 $R^{15}$, wherein the heterocyclic system is selected from indazolyl, indolinyl, indazolyl, isoindolyl, isothiadiazolyl, isoxazolyl, and thiazolyl.

In another embodiment, the present invention provides compounds of formula (I), wherein $R^5$ is selected from $(CR^{5a}H)_r$-phenyl substituted with 0-5 $R^{16}$; and a $(CR^{5a}H)_r$-heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, the present invention provides compounds of formula (I), wherein $R^5$ is $CH_2$phenyl substituted with 0-3 $R^{16}$.

In another embodiment, the present invention provides compound of formula (I), wherein B is selected from O and $NR^{17}$.

In another embodiment, the present invention provides compounds of formula (I), wherein $R^{16}$, at each occurrence, is independently selected from $C_{1-8}$ alkyl, $(CH_2)_rC_{3-6}$ cycloalkyl, $CF_3$, Cl, Br, I, F, $(CH_2)_rNR^{16a}R^{16a}$, $NO_2$, CN, OH, $(CH_2)_rOR^{16d}$, $(CH_2)_rC(O)R^{16b}$, $(CH_2)_rC(O)NR^{16a}R^{16a}$, $(CH_2)_rNR^{16f}C(O)R^{16b}$, $(CH_2)_rS(O)_pR^{16b}$, $(CH_2)_rS(O)_2NR^{16a}R^{16a}$, $(CH_2)_rNR^{16f}S(O)_2R^{16b}$, and $(CH_2)_r$-phenyl substituted with 0-3 $R^{16e}$; $R^{16a}$, at each occurrence, is independently selected from H, $C_{1-6}$ alkyl, $C_{3-6}$ cycloalkyl, and $(CH_2)_r$phenyl substituted with 0-3 $R^{16e}$; $R^{16b}$, at each occurrence, is independently selected from $C_{1-6}$ alkyl, $C_{3-6}$ cycloalkyl, and ($CH_2$substituted with 0-3 $R^{16e}$; $R^{16d}$, at each occurrence, is independently selected from $C_{1-6}$ alkyl and phenyl; $R^{16e}$, at each occurrence, is independently selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is independently selected from H, and $C_{1-5}$ alkyl.

In another embodiment, the present invention provides compounds of formula (I), wherein $R^{16}$, at each occurrence, is independently selected from Cl, Br, I, F, and CN.

In another embodiment, the present invention provides compounds of formula (I), wherein $R^4$ is selected from H and $R^5$.

In another embodiment, the present invention provides compounds of formula (I), wherein $R^{15}$, at each occurrence, is independently selected from $C_{1-8}$ alkyl, $(CH_2)_rC_{3-6}$ cycloalkyl, $CF_3$, Cl, Br, I, F, $(CH_2)_rNR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{15f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $(CH_2)_rNR^{15f}S(O)_2R^{15b}$, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$; $R^{15a}$, at each occurrence, is independently selected from H, $C_{1-6}$ alkyl, $C_{3-6}$ cycloalkyl, and $(CH_2)_r$phenyl substituted with 0-3 $R^{15e}$; alternatively, two $R^{15a}$s, along with the N to which they are attached, join to form a 5-6 membered heterocyclic system containing 1-2 heteroatoms selected from $NR^{15g}$, O, and S and optionally fused with a benzene ring or a 6-membered aromatic heterocycle; $R^{15b}$, at each occurrence, is independently selected from H, $C_{1-6}$ alkyl, $C_{3-6}$ cycloalkyl, and ($CH_2$substituted with 0-3 $R^{15e}$; $R^{15d}$, at each occurrence, is independently selected from $C_{1-6}$ alkyl and phenyl; $R^{15e}$, at each occurrence, is independently selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is independently selected from H, and $C_{1-5}$ alkyl.

In another embodiment, the present invention provides compounds of formula (I), wherein $R^{15}$, at each occurrence, is independently selected from $C_{1-8}$ alkyl, $(CH_2)_rC_{3-6}$ cycloalkyl, $CF_3$, Cl, Br, I, F, $NR^{15a}R^{15a}$, $NO_2$, CN, OH, $OR^{15d}$, $(CH_2)_rC(O)R^{15b}$, $C(O)NR^{15a}R^{15a}$, $NR^{15f}C(O)R^{15b}$, $_rOC(O)NR^{15a}R^{15a}$, $NR^{15f}C(O)OR^{15b}$, $S(O)_pR^{15b}$, $S(O)_2NR^{15a}R^{15a}$, $NR^{15f}S(O)_2R^{15b}$, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$, wherein the heterocyclic system is selected from tetrazolyl; $R^{15a}$, at each occurrence, is independently selected from H, methyl, ethyl, propyl, isopropy, benzyl and phenyl; $R^{15b}$, at each occurrence, is independently selected from H, methyl, ethyl, propyl, isopropy, benzyl and phenyl; $R^{15d}$, at each occurrence, is independently selected from methyl, ethyl, propyl, isopropy, and phenyl; $R^{15e}$, at each occurrence, is independently selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is independently selected from H, and methyl, ethyl, propyl and isopropyl.

In another embodiment, the present invention provides compounds of formula (I), wherein A is selected from cyclopropyl, cyclobutyl, cyclopentyl, cyclohexyl, and phenyl.

In another embodiment, the present invention provides compounds of formula (I), wherein A is selected from cyclohexyl, and phenyl.

In another embodiment, the present invention provides compounds of formula (I), wherein A is cyclohexyl.

In another embodiment, the present invention provides compounds of formula (I), wherein $R^9$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{9d}$, $(CH_2)_rSR^{9d}$, $(CH_2)_rNR^{9a}R^{9a}$, $(CH_2)_rC(O)OH$, $(CH_2)_rC(O)R^{9b}$, $(CH_2)_rC(O)NR^{9a}R^{9a}$, $(CH_2)_rNR^{9a}C(O)R^{9b}$, $(CH_2)_rNR^{9a}C(O)H$, $C_{1-6}$ haloalkyl, a $(CH_2)_r$—$C_{3-10}$ carbocyclic residue substituted with 0-5 $R^{9c}$, and a $(CH_2)_r$-5-10 membered heterocyclic system containing 1-4 heteroatoms selected from N, O, and S, substituted with 0-3 $R^{9c}$; $R^{9a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{9e}$, and a $(CH_2)_r$-4-10 membered heterocyclic system containing 1-4 heteroatoms selected from N, O, and S, substituted with 0-3 $R^{9e}$; alternatively, two $R^{9a}$s, along with the N to which they are attached, join to form a 5-6 membered heterocyclic system containing 1-2 heteroatoms selected from $NR^{9g}$, O, and S and optionally fused with a benzene ring or a 6-membered aromatic heterocycle.

In another embodiment, the present invention provides compounds of formula (I), wherein $R^9$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{9d}$, $(CH_2)_qSR^{9d}$, $(CH_2)_qNR^{9a}R^{9a}$.

In another embodiment, the present invention provides compounds of formula (I), wherein $R^{10}$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{10d}$, $(CH_2)_rSR^{10d}$, $(CH_2)_rNR^{10a}R^{10a}$; alternatively, $R^9$ and $R^{10}$ join to form =O, a $C_{3-10}$ cycloalkyl, a 5-6-membered lactone or lactam, or a 4-6-membered saturated heterocycle containing 1-2 heteroatoms selected from O, S, and $NR^{10g}$ and optionally fused with a benzene ring or a 6-membered aromatic heterocycle.

In another embodiment, the present invention provides compounds of formula (I), wherein $R^{10}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{10d}$, $(CH_2)_qSR^{10d}$, $(CH_2)_qNR^{10a}R^{10a}$.

In another embodiment, the present invention provides compounds of formula (I), wherein $R^{11}$ is selected from H, $C_{1-6}$ alkyl, $C_{2-8}$ alkenyl, $C_{2-8}$ alkynyl, $(CR'R^{17})_qOH$, $(CH_2)_qSH$, $(CR'R^{17})_qOR^{11d}$, $(CH_2)_qSR^{11d}$.

In another embodiment, the present invention provides compounds of formula (I), wherein $R^{12}$, is selected from H, $C_{1-6}$ alkyl, $C_{2-8}$ alkenyl, $C_{2-8}$ alkynyl, $(CHR')_qOH$, $(CH_2)_qSH$, $(CHR')_qOR^{12d}$, $(CH_2)_qSR^{12d}$, $(CHR')_qNR^{12a}R^{12a}$.

In another embodiment, the present invention provides compounds of formula (I), wherein $R^7$ is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_qSR^{7d}$, $(CH_2)_qNR^{7a}R^{7a}$.

In another embodiment, the present invention provides compounds of formula (I), wherein $R^7$, $R^8$, $R^9$, $R^{10}$, $R^{11}$, and $R^{12}$ are H.

In another embodiment, the present invention provides compounds of formula (I), wherein q is selected from 1, 2, and 3; and r is selected from 0, 1, 2, and 3.

In another embodiment, the present invention provides compounds of formula (I), wherein r is selected from 0, 1, and 2.

In another embodiment, the present invention provides compounds of formula (I), wherein $R^{14}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_r$, $NR^{14a}R^{14a}$, $(CHR')_rOH$, $(CHR')_rO(CHR')_rR^{14d}$, $(CHR')_rSH$, $(CHR')_rC(O)H$, $(CHR')_rS(CHR')_rR^{14d}$.

In another embodiment, the present invention provides compounds of formula (I), wherein $R^{17}$ is selected from H and methyl.

[15] In another embodiment, the present invention provides compounds of formula (I), wherein the compound is selected from:

N-(3-Acetyl-phenyl)-N'-{-3-[(2S)-3-benzyl]-5-oxo-piperazin-1-yl-propyl}-urea.

N-(5-Acetyl-4-methyl-thiazol-2-yl)-N'-{(1R,2S)-2-[(5S)-5-(4-fluoro-benzyl)-3-oxo-piperazin-1-yl-methyl]-cyclohexyl}-urea.

N-(5-Acetyl-4-methyl-thiazol-2-yl)-N'-{(1R,2S)-2-[(5S)-5-(4-fluoro-benzyl)-3,6-dioxo-piperazin-1-yl-methyl]-cyclohexyl}-urea.

N-(5-Acetyl-4-methyl-thiazol-2-yl)-N'-{(1R,2S)-2-[(5S)-5-(4-fluoro-benzyl)-(2S)-2-hydroxymethyl-3-oxo-piperazin-1-yl-methyl]-cyclohexyl}-urea.

N-(5-Acetyl-4-methyl-thiazol-2-yl)-N'{(1R,2S)-2-[(5S)-5-(4-fluoro-benzyl-(2R)-2-hydroxymethyl-3-oxo-piperizine-2-yl-methyl)-cyclohexyl}-urea N-(5-Acetyl-4-methyl-thiazol-2-yl)-N'-{(1R,2S)-2-[(5S)-5-(4-fluoro-benzyl)-3-oxo-4-N-methyl-piperazin-1-yl-methyl]-cyclohexyl}-urea.

N-(5-Acetyl-4-methyl-thiazol-2-yl)-N'-{(1R,2S)-2-[(5S)-5-(3-fluoro-benzyl)-3-oxo-4-N-methyl-piperazin-1-yl-methyl]-cyclohexyl}-urea.

N-(5-Acetyl-4-methyl-thiazol-2-yl)-N'-{(1R,2S)-2-[(5S)-5-(2-fluoro-benzyl)-3-oxo-piperazin-1-yl-methyl]-cyclohexyl}-urea.

N-(5-Acetyl-4-methyl-thiazol-2-yl)-N'-{(1R,2S)-2-[(5S)-5-benzyl-3,6-di-oxo-piperazin-1-yl-methyl]-cyclohexyl}-urea.

N-(5-Acetyl-4-methyl-thiazol-2-yl)-N'-{(1R,2S)-2-[(5S)-5-benzyl-3-oxo-piperazin-1-yl-methyl]-cyclohexyl}-urea.

N-(5-Acetyl-4-methyl-thiazol-2-yl)-N'-{(1R,2S)-2-[(5R)-5-(4-fluoro-benzyl)-3-oxo-piperazin-1-yl-methyl]-cyclohexyl}-urea.

N-(5-Acetyl-4-methyl-thiazol-2-yl)-N'-{(1R,2S)-2-[(5S)-5-(4-chloro-benzyl)-3-oxo-piperazin-1-yl-methyl]-cyclohexyl}-urea.

N-(5-Acetyl-4-methyl-thiazol-2-yl)-N'-{(1R,2S)-2-[(5R)-5-(4-chloro-benzyl)-3-oxo-piperazin-1-yl-methyl]-cyclohexyl}-urea.

N-(5-Acetyl-4-methyl-thiazol-2-yl)-N'-{(1R,2S)-2-[(5S)-5-(1-phenyl-ethyl)-3-oxo-piperazin-1-yl-methyl]-cyclohexyl}-urea.

N-(5-Acetyl-4-methyl-thiazol-2-yl)-N'-{(1R,2S)-2-[3-oxo-4-N-(4-fluoro-benzyl)-piperazin-1-yl-methyl]-cyclohexyl}-urea.

N-phenyl-N'-{(1R,2S)-2-[(5S)-5-benzyl-3-oxo-piperazin-1-yl-methyl]-cyclohexyl}-urea.

N-phenyl-N'-{(1R,2S)-2-[(5R)-5-benzyl-3-oxo-piperazin-1-yl-methyl]-cyclohexyl}-urea.

N-phenyl-N'-{(1R,2S)-2-[(5S)-5-benzyl-3-oxo-piperazin-1-yl-methyl]-cyclohexyl}-cyanoguanidine.

N-phenyl-N'-{(1R,2S)-2-[3-oxo-4-N-(4-fluoro-benzyl)-piperazin-1-yl-methyl]-cyclohexyl}-urea.

N-phenyl-N'-{(1R,2S)-2-[(2S)-2-benzyl-6-oxo-morpholin-4-yl-methyl]-cyclohexyl}-urea.

N-(3-cyanophenyl)-N'-{(1R,2S)-2-[(5S)-5-benzyl-3-oxo-piperazin-1-yl-methyl]-cyclohexyl}-urea.

N-(3-cyanophenyl)-N'-{(1R,2S)-2-[(5S)-5-benzyl-3-oxo-piperazin-1-yl-methyl]-cyclohexyl}-cyanoguanidine.

N-(3-Acetyl-4-fluorophenyl)-N'-{(1R,2S)-2-[(5S)-5-(4-fluoro-benzyl)-3-oxo-piperazin-1-yl-methyl]-cyclohexyl}-urea.

N-(3-acetylphenyl)-N'-{(1R,2S)-2-[(5S)-5-benzyl-3-oxo-piperazin-1-yl-methyl]-cyclohexyl}-cyanoguanidine.

N-(3-acetylphenyl)-N'-{(1R,2S)-2-[(5S)-5-benzyl-3-oxo-piperazin-1-yl-methyl]-cyclohexyl}-urea.

N-(3-acetylphenyl)-N'-{(1R,2S)-2-[(5S)-5-(4-fluoro-benzyl)-3-oxo-piperazin-1-yl-methyl]-cyclohexyl}-urea.

N-(3-acetylphenyl)-N'-{(1R,2S)-2-[(5S)-5-(3-fluoro-benzyl)-3-oxo-piperazin-1-yl-methyl]-cyclohexyl}-urea.

N-(3-acetylphenyl)-N'-{(1R,2S)-2-[(5S)-(2-fluoro-benzyl)-3-oxo-piperazin-1-yl-methyl]-cyclohexyl}-urea.

N-(3-acetylphenyl)-N'-{(1R,2S)-2-[(5S)-5-(4-fluoro-benzyl)-(2S)-2-hydroxymethyl-3-oxo-piperazin-1-yl-methyl]-cyclohexyl}-urea.

N-(3-acetylphenyl)-N'-{(1R,2S)-2-[(5S)-5-(4-fluoro-benzyl)-(2R)-2-hydroxymethyl-3-oxo-piperazin-1-yl-methyl]-cyclohexyl}-urea.

N-(3-Acetyl-phenyl)-N'-{(1R,2S)-2-[(5S)-5-(4-fluoro-benzyl)-3-oxo-4-N-methyl-piperazin-1-yl-methyl]-cyclohexyl}-urea.

N-(3-Acetyl-phenyl)-N'-{(1R,2S)-2-[(5S)-5-(4-fluoro-benzyl)-3-oxo-4-N-benzyl-piperazin-1-yl-methyl]-cyclohexyl}-urea.

N-(3-Acetyl-phenyl)-N'-{(1R,2S)-2-[(5S)-5-(4-fluoro-benzyl)-3,6-di-oxo-piperazin-1-yl-methyl]-cyclohexyl}-urea.

N-(3-Acetyl-phenyl)-N'-{(1R,2S)-2-[(5R)-5-(4-fluoro-benzyl)-3-oxo-piperazin-1-yl-methyl]-cyclohexyl}-urea.

N-(3-Acetyl-phenyl)-N'-{(1R,2S)-2-[(5S)-5-(4-chloro-benzyl)-3-oxo-piperazin-1-yl-methyl]-cyclohexyl}-urea.

N-(3-Acetyl-phenyl)-N'-{(1R,2S)-2-[(5S)-5-(3-cyano-benzyl)-3-oxo-piperazin-1-yl-methyl]-cyclohexyl}-urea.

N-(3-Acetyl-phenyl)-N'-{(1R,2S)-2-[(5R)-5-(3-cyano-benzyl)-3-oxo-piperazin-1-yl-methyl]-cyclohexyl}-urea.

N-(3-Acetyl-phenyl)-N'-{(1R,2S)-2-[(5S)-5-(1-phenyl-ethyl)-3-oxo-piperazin-1-yl-methyl]-cyclohexyl}-urea.

N-(3-Acetyl-phenyl)-N'-{(1R,2S)-2-[3-oxo-4-N-(4-fluoro-benzyl)-piperazin-1-yl-methyl]-cyclohexyl}-urea.

N-(3-Acetyl-phenyl)-N'-{(1R,2S)-2-[(2S)-2-(benzyl)-6-oxo-morpholin-4-yl-methyl]-cyclohexyl}-urea.

N-(3-Acetyl-phenyl)-N'-{(1R,2S)-2-[4-oxo-1,3,4,6,11,11a-hexahydro-pyrazino[1,2-b]-isoquinolin-2-yl-methyl]-cyclohexyl}-urea.

N-[3-(1-hydroxy-ethyl)-phenyl]-N'-{(1R,2S)-2-[(5S)-5-(4-fluoro-benzyl)-(2S)-(2-hydroxy-methyl)-3-oxo-piperazin-1-yl-methyl]-cyclohexyl}-urea.

N-(indazol-5-yl)-N'-{(1R,2S)-2-[(5S)-5-(4-fluoro-benzyl)-3,6-di-oxo-piperazin-1-yl-methyl]-cyclohexyl}-urea.

N-(indazol-5-yl)-N'-{(1R,2S)-2-[(5S)-5-benzyl-3,6-di-oxo-piperazin-1-yl-methyl]-cyclohexyl}-urea.

N-(indazol-5-yl)-N'-{(1R,2S)-2-[(5S)-5-benzyl-3-oxo-piperazin-1-yl-methyl]-cyclohexyl}-urea.

N-(indazol-5-yl)-N'-{(1R,2S)-2-[(5S)-5-(4-fluoro-benzyl)-3-oxo-piperazin-1-yl-methyl]-cyclohexyl}-urea.

N-(3,5-di-Acetyl-phenyl)-N'-{(1R,2S)-2-[(5S)-5-(4-fluoro-benzyl)-3-oxo-piperazin-1-yl-methyl]-cyclohexyl}-urea.

N-(3,5-di-Acetyl-phenyl)-N'-{(1R,2S)-2-[(5S)-5-(3-fluoro-benzyl)-3-oxo-piperazin-1-yl-methyl]-cyclohexyl}-urea.

N-(3,5-di-Acetyl-phenyl)-N'-{(1R,2S)-2-[(5S)-5-(2-fluoro-benzyl)-3-oxo-piperazin-1-yl-methyl]-cyclohexyl}-urea.

N-(3,5-di-Acetyl-phenyl)-N'-{(1R,2S)-2-[(5S)-5-(4-fluoro-benzyl)-3-oxo-4-N-methyl-piperazin-1-yl-methyl]-cyclohexyl}-urea.

N-(3,5-di-Acetyl-phenyl)-N'-{(1R,2S)-2-[(5S)-5-(4-fluoro-benzyl)-3,6-di-oxo-piperazin-1-yl-methyl]-cyclohexyl}-urea.

N-(3,5-di-Acetyl-phenyl)-N'-{(1R,2S)-2-[(5R)-5-(4-fluoro-benzyl)-3-oxo-piperazin-1-yl-methyl]-cyclohexyl}-urea.

N-(3,5-di-Acetyl-phenyl)-N'-{(1R,2S)-2-[(5S)-5-(1-phenyl-ethyl)-3-oxo-piperazin-1-yl-methyl]-cyclohexyl}-urea.

N-(3,5-di-Acetyl-phenyl)-N'-{(1R,2S)-2-[(2S)-2-(benzyl)-6-oxo-morpholin-4-yl-methyl]-cyclohexyl}-urea.

N-(3,5-di-Acetyl-phenyl)-N'-{(1R,2S)-2-[(5S)-5-(2-fluoro-benzyl)-3,6-di-oxo-piperazin-1-yl-methyl]-cyclohexyl}-urea.

N-(3,5-di-Acetyl-phenyl)-N'-{(1R,2S)-2-[(5S)-5-(4-fluoro-benzyl)-3-oxo-4-N-methyl-piperazin-1-yl-methyl]-cyclohexyl}-urea.

N-(3,5-di-Acetyl-phenyl)-N'-{(1R,2S)-2-[(5S)-5-(4-fluoro-benzyl)-3-oxo-4-N-benzyl-piperazin-1-yl-methyl]-cyclohexyl}-urea.

N-[3-(1-methyl-1H-tetrazol-5-yl)phenyl]-N'-{(1R,2S)-2-[(5S)-5-(4-fluoro-benzyl)-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(2-fluoro-benzyl)-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(4-fluoro-benzyl)-(2S)-2-hydroxymethyl-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(4-fluoro-benzyl)-(2R)-2-hydroxymethyl-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(4-fluoro-benzyl)-3-oxo-4-N-methyl-piperazin-1-yl-methyl]-cyclohexyl}-urea.

N-[3-(1-methyl-1H-tetrazol-5-yl)phenyl]-N'-{(1R,2S)-2-[(5S)-5-(4-fluoro-benzyl)-3-oxo-4-N-benzyl-piperazin-1-yl-methyl]-cyclohexyl}-urea.

N-[3-(1-methyl-1H-tetrazol-5-yl)phenyl]-N'-{(1R,2S)-2-[(5R)-5-(4-fluoro-benzyl)-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(4-chloro-benzyl)-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(3-cyano-benzyl)-3-oxo-piperazin-1-yl-methyl]-cyclohexyl}-urea.

N-[3-(1-methyl-1H-tetrazol-5-yl)phenyl]-N'-{(1R,2S)-2-[(5R)-5-(3-cyano-benzyl)-3-oxo-piperazin-1-yl-methyl]-cyclohexyl}-urea.

N-[3-(1-methyl-1H-tetrazol-5-yl)phenyl]-N'-{(1R,2S)-2-[(5S)-5-(1-phenyl-ethyl)-3-oxo-piperazin-1-yl-methyl]-cyclohexyl}-urea.

N-[3-(1-methyl-1H-tetrazol-5-yl)phenyl]-N'-{(1R,2S)-2-[3-oxo-4-N-(4-fluoro-benzyl)-piperazin-1-yl-methyl]-cyclohexyl}-urea.

N-[3-(1-methyl-1H-tetrazol-5-yl)phenyl]-N'-{(1R,2S)-2-[4-oxo-1,3,4,6,11,11a-hexahydro-pyrazino[1,2-b]-isoquinolin-2-yl-methyl]-cyclohexyl}-urea.

N-[indolin-5-yl)phenyl]-N'-{(1R,2S)-2-[(5S)-5-(4-fluoro-benzyl)-3-oxo-piperazin-1-yl-methyl]-cyclohexyl}-urea.

N-[indolin-5-yl)phenyl]-N'-{(1R,2S)-2-[(5S)-5-(4-fluoro-benzyl)-3-oxo-piperazin-1-yl-methyl]-cyclohexyl}-urea.

N-(4-methyl-thiazol-2-yl)-N'-{(1R,2S)-2-[(5S)-5-(3-fluoro-benzyl)-3-oxo-piperazin-1-yl-methyl]-cyclohexyl}-urea.

N-(thiadiazol-2-yl)-N'-{(1R,2S)-2-[(5S)-5-(4-fluoro-benzyl)-3-oxo-piperazin-1-yl-methyl]-cyclohexyl}-urea.

N-(1-methyl-pyrazol-3-yl)-N'-{(1R,2S)-2-[(5S)-5-(4-fluoro-benzyl)-3-oxo-piperazin-1-yl-methyl]-cyclohexyl}-urea.

N-(thiazol-2-yl)-N'-{(1R,2S)-2-[(5S)-5-(4-fluoro-benzyl)-3-oxo-piperazin-1-yl-methyl]-cyclohexyl}-urea.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides pharmaceutical composition comprising a pharmaceutically acceptable carrier and a therapeutically effective amount of a compound of the present invention or a pharmaceutically acceptable salt thereof.

In another embodiment, the present invention provides a method of of modulation of chemokine receptor activity which comprises contacting a CCR3 receptor with an effective inhibitory amount of the compound.

In another embodiment, the present invention provides a method for treating or preventing inflammatory disorders comprising administering to a patient in need thereof a therapeutically effective amount of a compound of the present invention, or a pharmaceutically acceptable salt thereof.

In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the present invention provides a method for treating or preventing disorders selected from asthma, allergic rhinitis, atopic dermatitis, and inflammatory bowel diseases.

In another embodiment, the present invention provides a method for treating or preventing asthma.

In another embodiment, the present invention provides novel compounds of formula (I) for use in therapy.

In another embodiment, the present invention provides the use of novel compounds of formula (I) for the manufacture of a medicament for the treatment of HIV infection.

It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments. For example, the first embodiment may be combined with the embodiment wherein $R^{19}$ is absent, taken with the nitrogen to which it is attached to form an N-oxide, or selected from $C_{1-8}$ alkyl, $(CH_2)_rC_{3-6}$ cycloalkyl, and $(CH_2)_r$-phenyl substituted with 0-3 $R^{19c}$; $R^{19c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{19a}R^9$, and $(CH_2)_r$phenyl; alternatively, $R^{19}$ joins with $R^7$, $R^9$, or $R^{11}$ to form a 5, 6 or 7 membered piperidinium spirocycle or pyrrolidinium spirocycle substituted with 0-3 $R^a$; and further combined with the embodiment wherein Z is O. As a further example, the embodiment wherein Z is selected from O, S, N(CN), and $N(CONH_2)$ may be combined with any other embodiment listed above.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue", is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are envisioned for this invention.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

Generally, the route described in Scheme 1 can be used to synthesize the compounds described in the scope of this patent application. The appropriately substituted piperazin-2-one (B=N—$R^{17}$) 1 or morpholin-2-one (B=O) 1 is alkylated by a N-protected alkylhalide (halide=Cl, Br, I), mesylate, tosylate or triflate) 2 to yield the 4-alkyl-piperazin-2-one or morpholin-2-one protected amine 3. (In the following schemes, substituents on ring D are designated as $R^5$, $R^6$, and $R^{13}$. This designation is for the purposes of the Schemes only and is not meant to limit the definitions for ring D substitution in the claims.) E represents a linkage described within the scope of this application in its fully elaborated form (or in a precursor form which can be later elaborated) with the appropriate protecting groups as understood by one skilled in the art. If the halide is not I, then KI can also be added to facilitate the displacement, provided the solvent is suitable, such as an alcohol, 2-butanone, DMF or DMSO, amongst others. The displacement can be performed at room temperature to the reflux temperature of the solvent. Alternatively, the appropriately substituted piperazin-2-one 1 or morpholin-2-one 1 is reductively alkylated with the aldehyde 2 (X=CHO), to give the protected amine 3. The protecting group is subsequently removed to yield amine 4. Suitable protected amino groups include: phthalimide (which can be removed by hydrazine); bis-BOC (which can be removed by either TFA or HCl dissolved in a suitable solvent); a nitro group (instead of an amine which can be reduced to yield an amine); 2,4-dimethylpyrrole (S. P. Breukelman, et al. J. Chem. Soc. Perkin Trans. I, 1984, 2801); N-1,1,4,4-Tetramethyl-disilylazacyclopentane (STABASE) (S. Djuric, J. Venit, and P. Magnus Tet. Lett 1981, 22, 1787); and other protecting groups know by one skilled in the art. Reaction with an isocyanate or isothiocyanate 5 (Z=O,S) yields urea or thiourea 6. Reaction with a chloroformate or chlorothioformate 7 (Z=O,S) such as o-, p-nitrophenyl-chloroformate or phenylchloroformate (or their thiocarbonyl equivalents), followed by displacement with an amine 9, also yields the corresponding urea or thiourea 6. Likewise, reaction of carbamate 8 (Y=H, or 2- or 4-NO2) with disubstituted amine 10 yields trisubstituted urea or thiourea 12. Reaction of the amine 4 with an N,N-disubstituted carbamoyl chloride 11 (or its thiocarbonyl equivalent) yields the corresponding N,N-disubstituted urea or thiourea 12. Amine 4 can also be reductively aminated to yield 13 by conditions familiar to one skilled in the art and by the following conditions: Abdel-Magid, A. F., et al. Tet. Lett. 1990, 31, (39) 5595-5598. This secondary amine can subsequently be reacted with isocyanates or isothiocyanates to yield trisubstituted ureas 14 or with carbamoyl chlorides to yield tetrasubstituted ureas 15.

Scheme 1

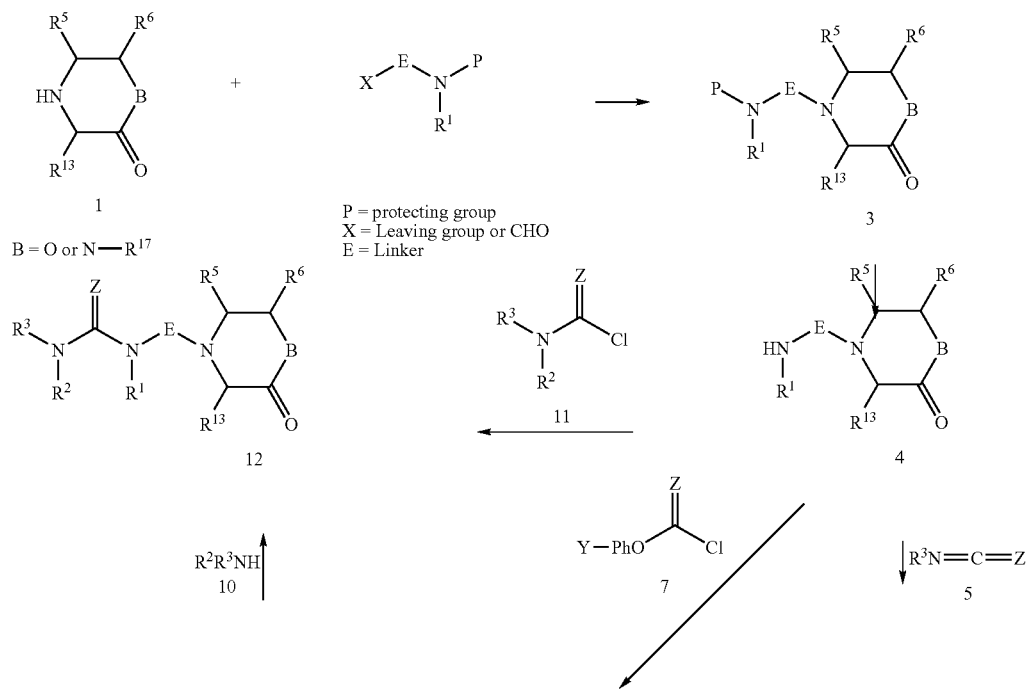

-continued

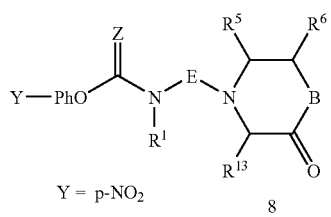

8

Y = p-NO$_2$

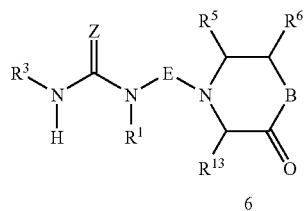

6

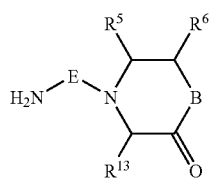

4 (R$^1$ = H)

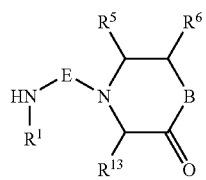

13

(R$^1$ = RCH$_2$)

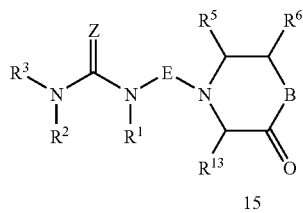

15

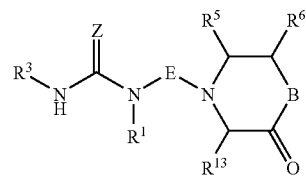

14

One can also convert amine 4 into an isocyanate, isothiocyanate, carbamoyl chloride or its thiocarbonyl equivalent (isocyanate: Nowakowski, J. J Prakt. Chem/Chem-Ztg 1996, 338 (7), 667-671; Knoelker, H.-J. et al., Angew. Chem. 1995, 107 (22), 2746-2749; Nowick, J. S. et al., J. Org. Chem. 1996, 61 (11), 3929-3934; Staab, H. A.; Benz, W.; Angew Chem 1961, 73; isothiocyanate: Strekowski L. et al., J. Heterocycl. Chem. 1996, 33 (6), 1685-1688; Kutschy, Pet al., Synlett. 1997, (3), 289-290) carbamoyl chloride: Hintze, F.; Hoppe, D.; Synthesis (1992) 12, 1216-1218; thiocarbamoyl chloride: Ried, W.; Hillenbrand, H.; Oertel, G.; Justus Liebigs Ann Chem 1954, 590) (these reactions are not shown in Scheme 1). These isocyanates, isothiocyantes, carbamoyl chlorides or thiocarbamoyl chlorides can then be reacted with R$^2$R$^3$NH to yield di- or trisubstituted ureas or thioureas 12. An additional urea forming reaction involves the reaction of carbonyldiimidazole (CDI) (Romine, J. L.; Martin, S. W.; Meanwell, N. A.; Epperson, J. R.; Synthesis 1994 (8), 846-850) with 4 followed by reaction of the intermediate imidazolide with 9 or in the reversed sequence (9+CDI, followed by 4). Activation of imidazolide intermediates also facilitates urea formation (Bailey, R. A., et al., Tet. Lett. 1998, 39, 6267-6270). One can also use 13 and 10 with CDI. The urea forming reactions are done in a non-hydroxylic inert solvent such as THF, toluene, DMF, etc., at room temperature to the reflux temperature of the solvent and can employ the use of an acid scavenger or base when necessary such as carbonate and bicarbonate salts, triethylamine, DBU, Hunigs base, DMAP, etc.

Substituted piperazin-2-ones 1 can either be obtained commercially or be prepared as shown in Scheme 2. Commercially available N-protected amino acids can be converted to the Weinreb amides 17, which are then reduced with LAH to the aldehydes 18 (R$^5$=H) or treated with Grignards to give the ketones 18. Reductive amination of 18 with benzyl amines or amino esters 20 gives the amines 19 or 21, respectively. Alkylation of 19 with ester 23 (X=halide, mesylate, triflate, etc.) gives the ester 22. Removal of the nitrogen protecting group of 21 or 22, followed by cyclization gives the piperazin-2-ones 25 or 24. The amide nitrogen of piperazin-2-ones 24 can be alkylated (NaH, R$^{17}$X) to give 27. Hydrogenolysis of 27 gives the desired piperazin-2-ones 28. Alternatively, the basic nitrogen of piperazin-2-ones 25 can be alkylated to give the isomeric piperazin-2-ones 26.

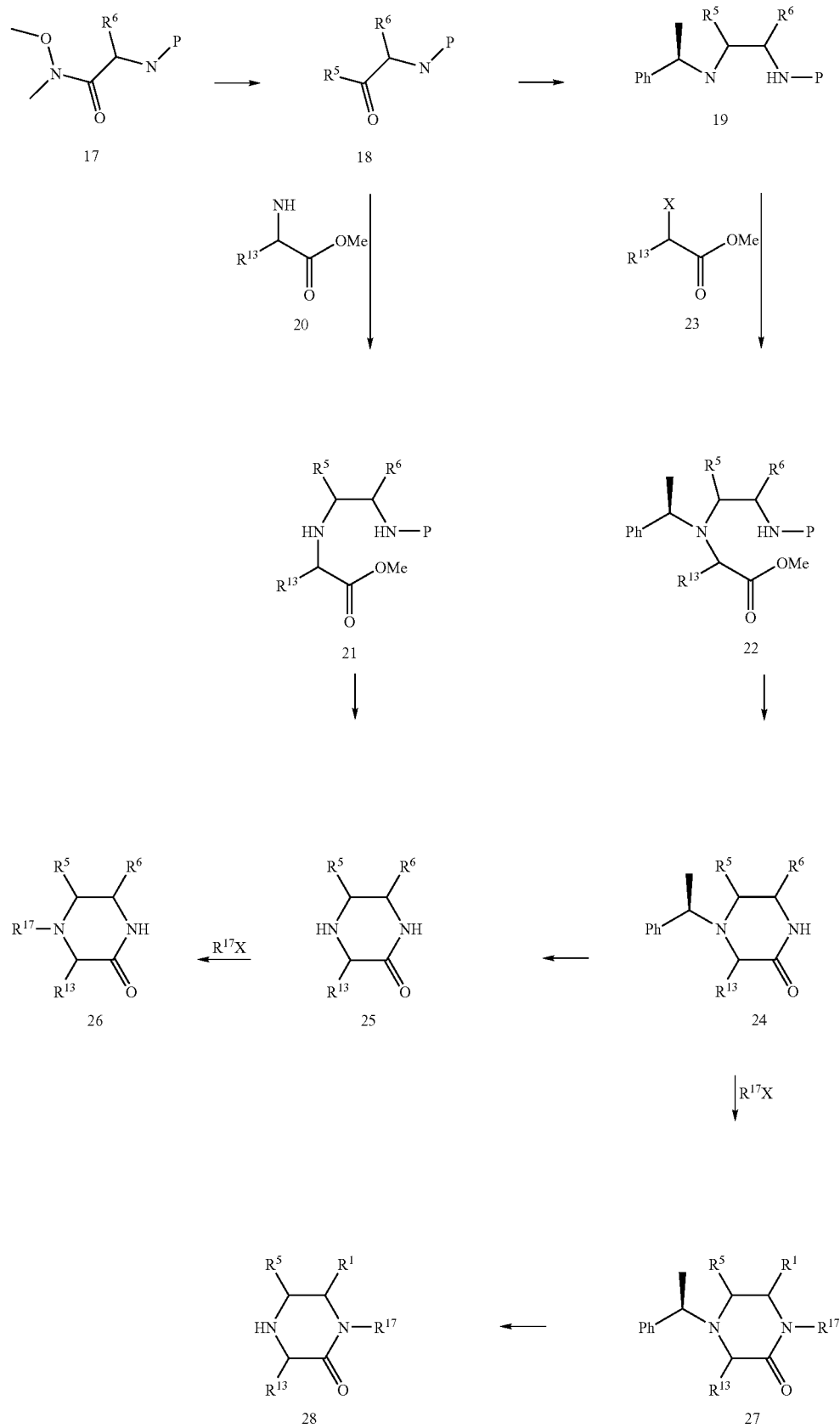

The corresponding substituted morpholin-2-one (B=O) 1 can prepared as shown in Scheme 3. Commercially available N-protected amino acids can be converted to the Weinreb amides 17, which are then reduced with LAH to the aldehydes 18 ($R^6$=H) or treated with Grignards to give the ketones 18. Reduction of 18 gives the amino alcohols 31 (B=O). Alternately, the α-hydroxy acid derivatives can be converted to the Weinreb amides 29, which can then reduced with LAH to the aldehydes 30 ($R^5$=H) or treated with Grignards to give the ketones 30. Reductive amination of 30 gives the amines 31 (B=O). Reductive amination of 30 with amino esters 20 or alkylation of 31 (B=O) with ester 23 (X=halide, mesylate, triflate, etc.) gives the ester 33. Removal of the oxygen protecting group of 33, followed by cyclization gives the morpholin-2-ones 34. The amino ketone 18 can be reduced to the alcohol 31 (B=O) or can under go a reductive amination to the diamine 31 (B=N—$R^{17}$). These can also be acylated with the α-hydroxy acid derivative 36 to give the amide 32. Removal of the protecting group of 32, followed by cyclization gives the isomeric morpholin-3-ones or piperazin-3-ones 35.

Compounds where Z=N—CN, $CHNO_2$, and $C(CN)_2$ can be synthesized by the methods shown in Scheme 4. Amine 10 (Scheme 1) reacts with malononitrile 37 neat or in an inert solvent at room temperature to the reflux temperature of the solvent, or at the melting point of the solid/solid mixture, to yield maloonitrile 38. Likewise, a similar reaction sequence may be used to make 40 and 42. These in turn can undergo reaction with amine 4 under similar conditions stated just above to yield the derivative 15. The malononitrile analog (Z=$C(CN)_2$) may be synthesized by the method of S. Sasho, et al. (J. Med. Chem. 1993, 36, 572-579, and P. Traxler, et al., J. Med. Chem. (1997), 40, 3601-3616. The cyanoguanidines (Z=N—CN) can be synthesized by the method of K. S. Atwal, et al. and references contained

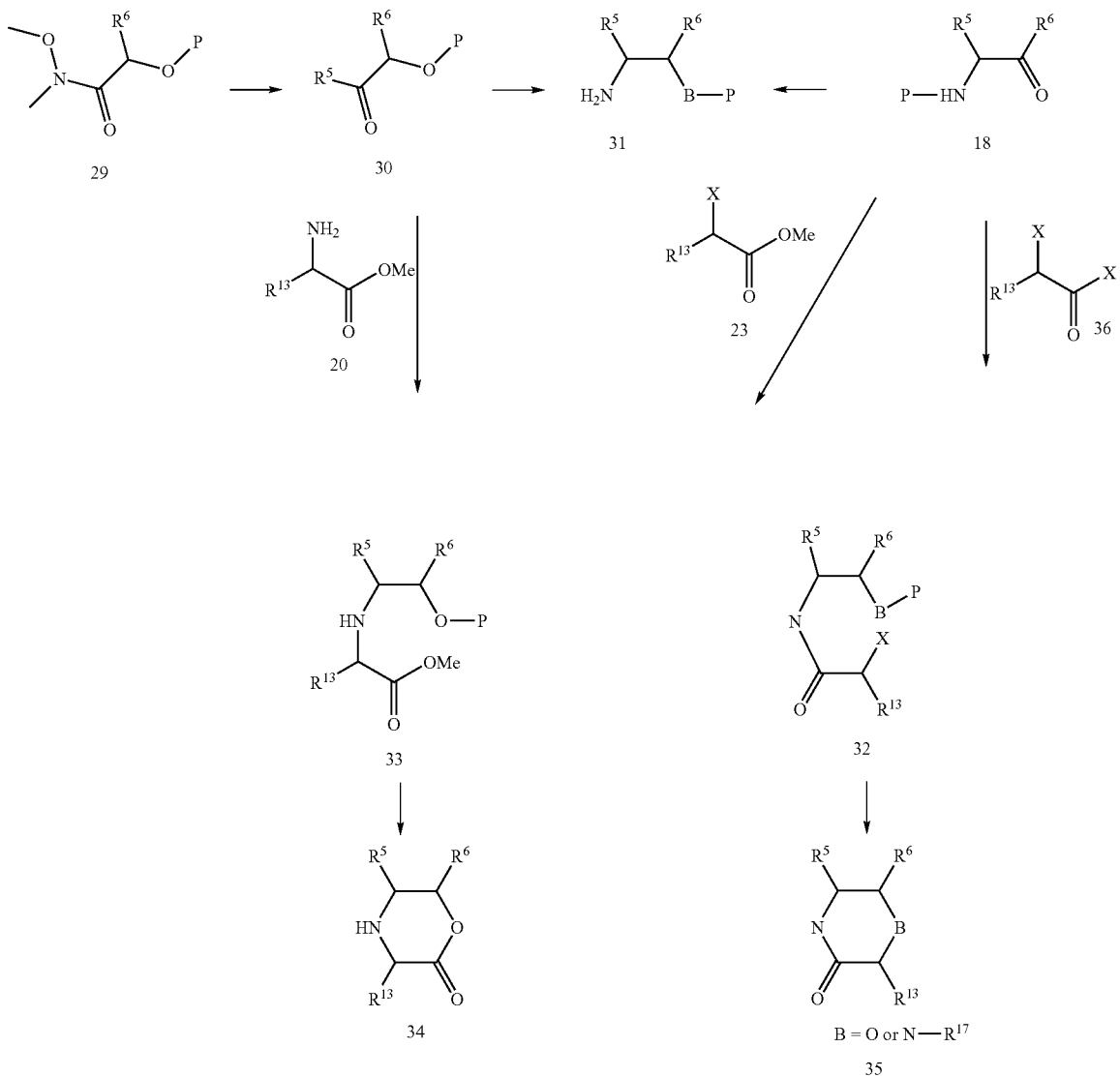

therein (J. Med. Chem. (1998) 41, 271-275). The nitroethylene analog (Z=C—NO$_2$) can be synthesized by the method of F. Moimas, et al. (Synthesis 1985, 509-510) and J. M. Hoffman, et al., (J. Med. Chem. (1983) 26, 140-144) and references contained therein.

Guanidines (Z=NR$^{1a}$) can be synthesized by the methods outlined in Scheme 5. Compound 43 where Z=S can be methylated to yield the methylisothiourea 44. Displacement of the SMe group with amines yields substituted guanidines 45 (see H. King and I. M. Tonkin J. Chem. Soc. 1946, 1063 and references therein). Alternatively, reaction of thiourea 43 with amines in the presence of triethanolamine and "lac sulfur" which facilitates the removal of H$_2$S yields substituted guanidines 45 (K. Ramadas, Tet. Lett. 1996, 37, 5161 and references therein).

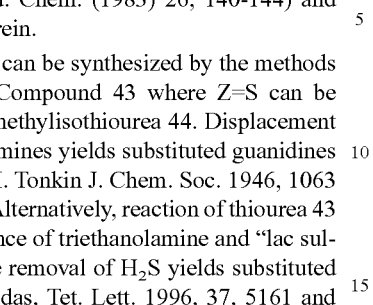

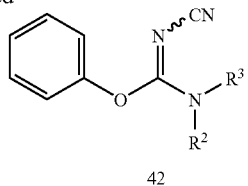

A method for introducing substituents in linkage E is that of A. Chesney et al. (Syn. Comm. 1990, 20 (20), 3167-3180) as shown in Scheme 6. Michael reaction of piperazin-2-one (B=N—R$^{17}$) 1 or morpholin-2-one (B=O) 1 with Michael acceptor 46 yields intermediate 47 which can undergo subsequent reactions in the same pot. For example, reduction yields alcohol 48 which can be elaborated to the amine 49 by standard procedures familiar to one skilled in the art. Some of these include mesylation or tosylation followed by displacement with NaN$_3$ followed by reduction to yield amine 49. Another route as depicted in Scheme 6 involves reaction with diphenylphosphoryl azide followed by reduction of the azide to yield amine 49.

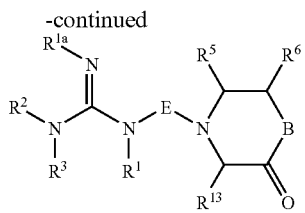

45

The mesylate or tosylate can also be displaced by other nucleophiles such as NH$_3$, BOC$_2$N$^-$, potassium phthalimide, etc., with subsequent deprotection where necessary to yield amines 49. Finally, 49 can be converted to urea or thiourea 50 by procedures discussed for Scheme 1 or to the compounds of this invention by procedures previously discussed. Similarly, aldehyde 47 may be reacted with a lithium or a Grignard reagent 51 to yield alcohol adduct 52. This in turn can be converted to urea or thiourea 54 in the same way as discussed for the conversion of 48 to 50.

Scheme 7 shows that intermediate 56 can be extended via a Wittig reaction (A. Chesney, et al. Syn. Comm. 1990, 20 (20), 3167-3180) to yield 57. This adduct can be reduced catalytically to yield 58 or by other procedures familiar to one skilled in the art. Alkylation yields 59, followed by saponification and Curtius rearrangement (T. L. Capson and C. D. Poulter, Tet. Lett., (1984) 25, 3515-3518) followed by reduction of the benzyl protecting group yields amine 60 which can be elaborated further as was described earlier in Scheme 1 and elsewhere in this application to make the compounds of this invention.

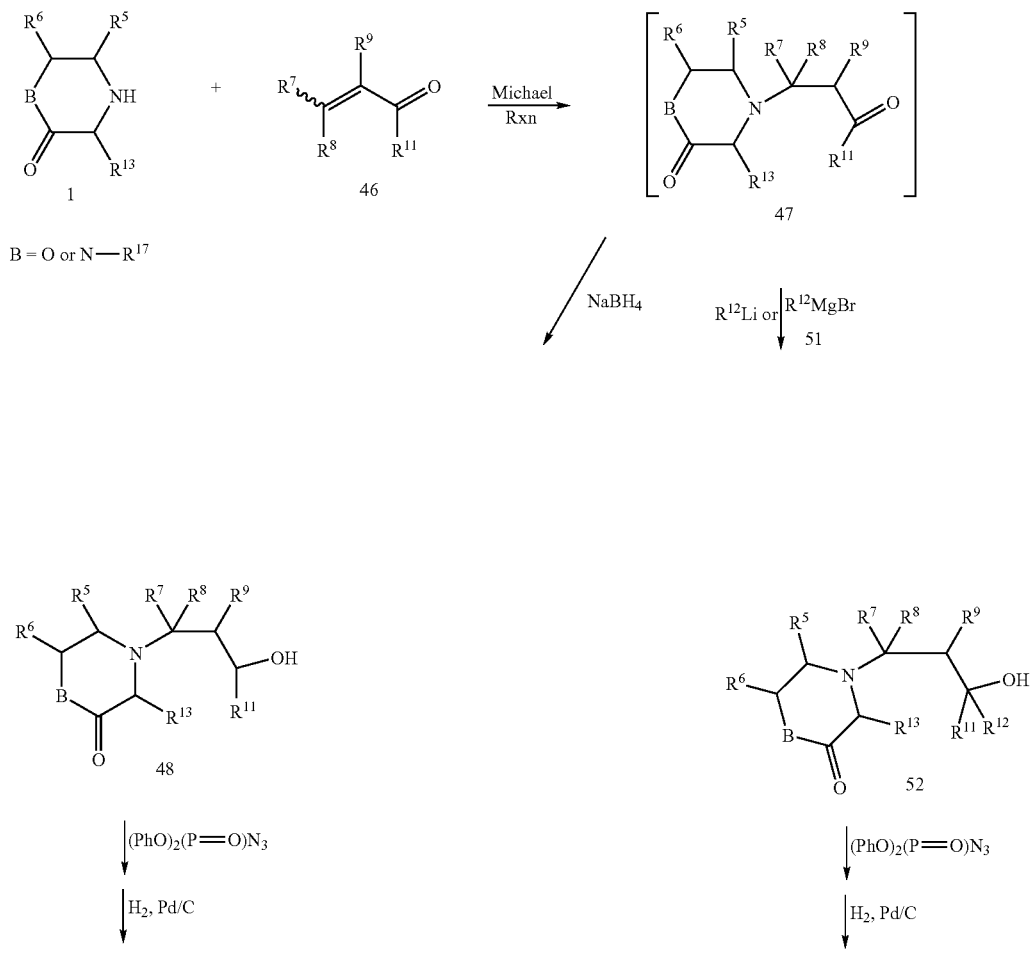

45
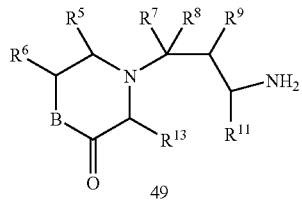
49
as described previously ↓
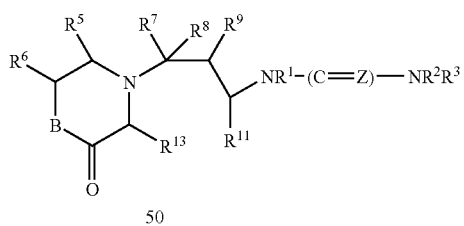
50
46
-continued
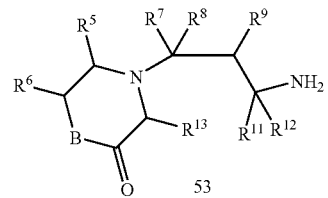
53
as described previously ↓
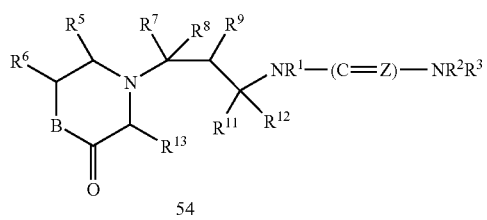
54
Scheme 7
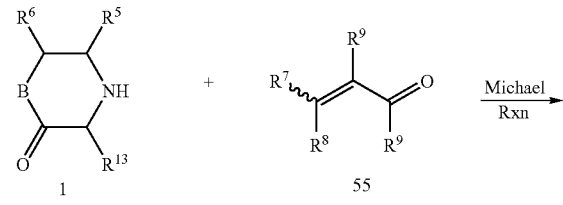
1
B = O or N—R$^{17}$
+ 55 → Michael Rxn →
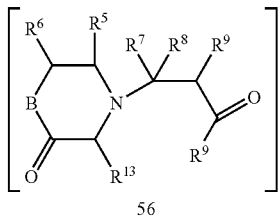
56
Wittig ↓ PPh$_3$ / R$^{11}$ / OMe / O
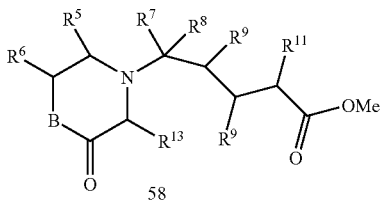
58
← H$_2$ Pd/C
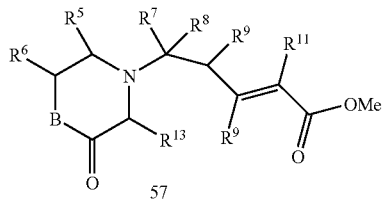
57
1. LDA
2. R$^{12}$X ↓
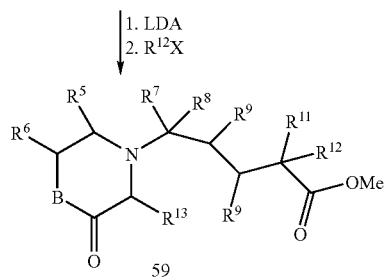
59
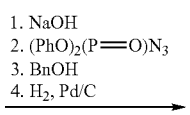
1. NaOH
2. (PhO)$_2$(P=O)N$_3$
3. BnOH
4. H$_2$, Pd/C
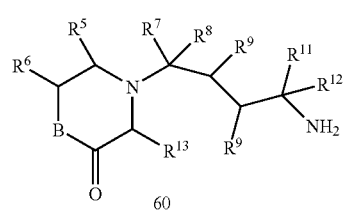
60

Scheme 8 shows that dialkyllithium cuprate, organocopper, or copper-catalyzed Grignard addition (for a review, see G. H. Posner, "An Introduction to Synthesis Using Organocopper Reagents", J. Wiley, New York, 1980; Organic Reactions, 19, 1 (1972)) to alpha, beta-unsaturated ester 57 yields 61 which can undergo subsequent transformations just discussed to yield amine 63, and then elaborated further to the compounds of this invention as was described earlier. The intermediate enolate ion obtained upon cuprate addition to 57 can also be trapped by an electrophile to yield 62 (for a review, see R. J. K. Taylor, Synthesis 1985, 364). Likewise, another 2-carbon homologation is reported by A. Chesney et al. (ibid.) on intermediate 56 which involves reacting 56 with an enolate anion to yield aldol condensation product 62 (where $R^{10}$=OH). The hydroxyl group can undergo synthetic transformations which are familiar to one skilled in the art and which will be discussed in much detail later on in the application. Chiral auxilliaries can also be used to introduce stereo- and enantioselectivity in these aldol condensations, procedures familiar to one skilled in the art. Examples of such methods are taught in D. A. Evans, et al., J. Am. Chem. Soc. 1981, 103, 2127; D. A. Evans, J. Am. Chem. Soc. 1982, 104, 1737; D. A. Evans, J. Am. Chem. Soc. 1986, 108, 2476; D. A. Evans. et al., J. Am. Chem. Soc. 1986, 108, 6757; D. A. Evans, J. Am. Chem. Soc. 1986, 108, 6395; D. A. Evans, J. Am. Chem. Soc. 1985, 107, 4346; A. G. Myers, et al., J. Am. Chem. Soc. 1997, 119, 6496. One can also perform an enantioselective alkylation on esters 58 or 61 with $R^{12}X$ where X is a leaving group as described in Scheme 1, provided the ester is first attached to a chiral auxiliary (see above references of Evans, Myers and Mauricio de L. Vanderlei, J. et al., Synth. Commun. 1998, 28, 3047).

One can also react alpha,beta-unsaturated ester 57 (Scheme 9) with Corey's dimethyloxosulfonium methylide (E. J. Corey and M. Chaykovsky, J. Am. Chem. Soc. 1965, 87, 1345) to form a cyclopropane which can undergo eventual Curtius rearrangement and subsequent elaboration to the compounds of this invention wherein the carbon containing $R^9R^{10}$ is tied up in a cyclopropane ring with the carbon containing $R^{11}R^{12}$.

Scheme 8

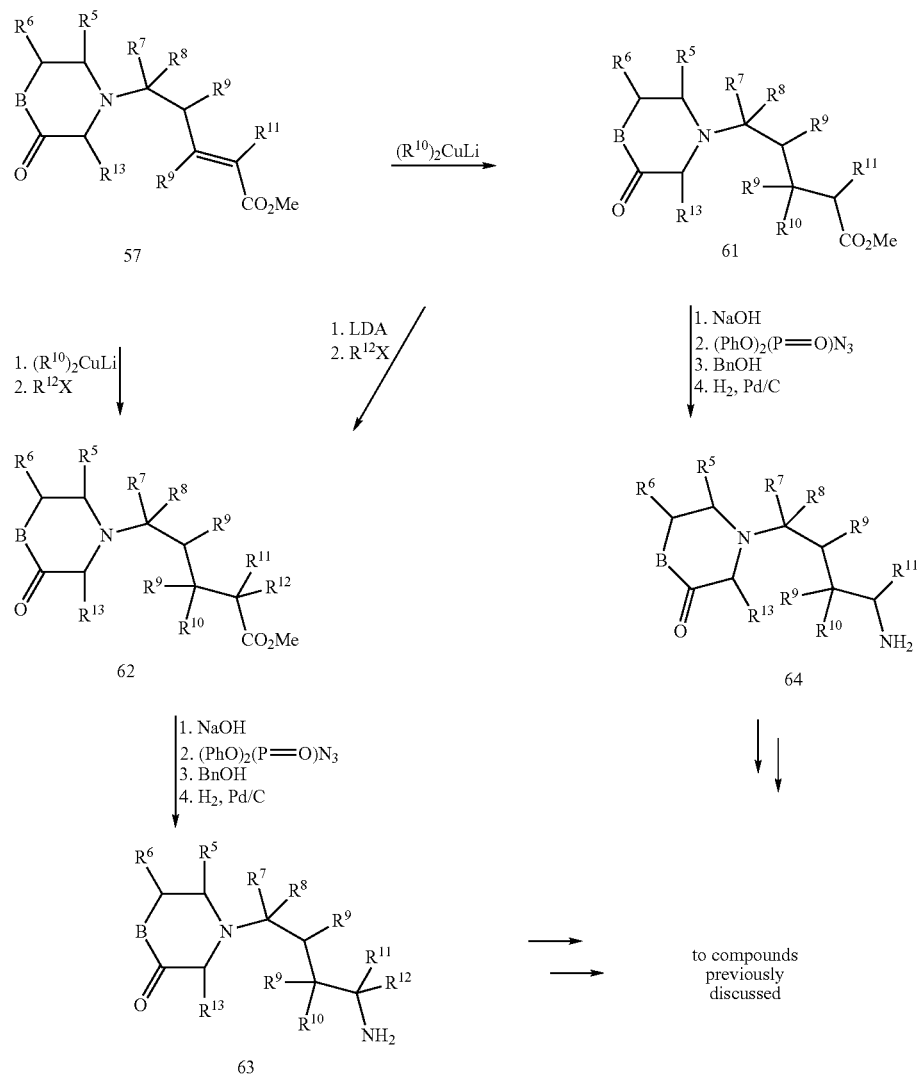

Scheme 9

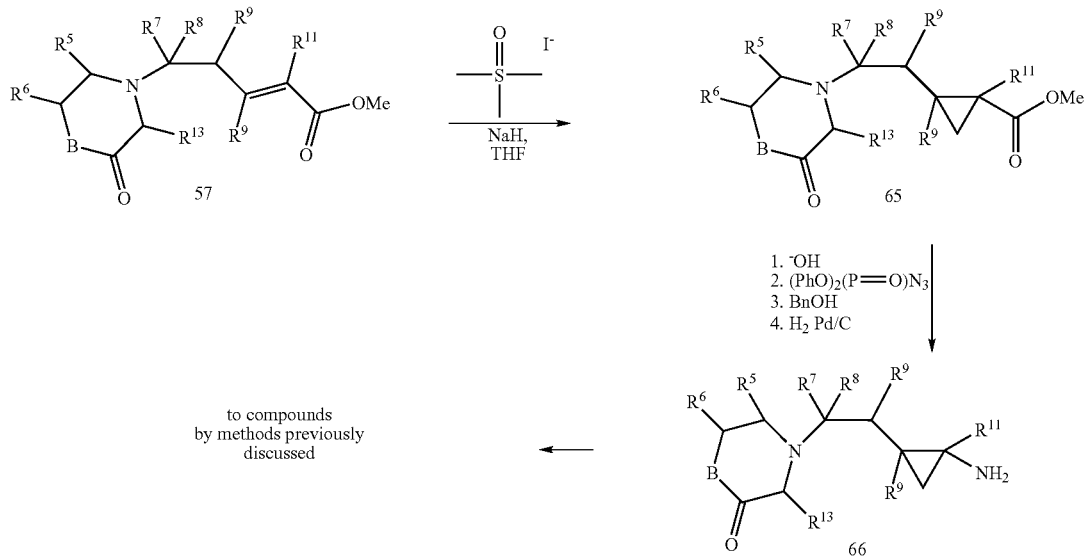

In addition, compound 68 (Scheme 9a) can also undergo the analogous reactions just described to form cyclopropylamine 70, which can be further elaborated into the compounds of this invention as described previously. Compound 68 can also be synthesized by an alkylation reaction of piperazin-2-one 1 or morpholin-2-one 1 with bromide 67 in an inert solvent employing the conditions as described for the alkylation of 2 by 1 in Scheme 1.

Another way to synthesize the compounds in the scope of this application is shown in Scheme 10. Michael reaction of amine 1 with an acrylonitrile 71 (as described by I. Roufos in J. Med. Chem. 1996, 39, 1514-1520) followed by Raney-Nickel hydrogenation yields amine 73 which can be elaborated to the compounds of this invention as previously described.

Scheme 9a

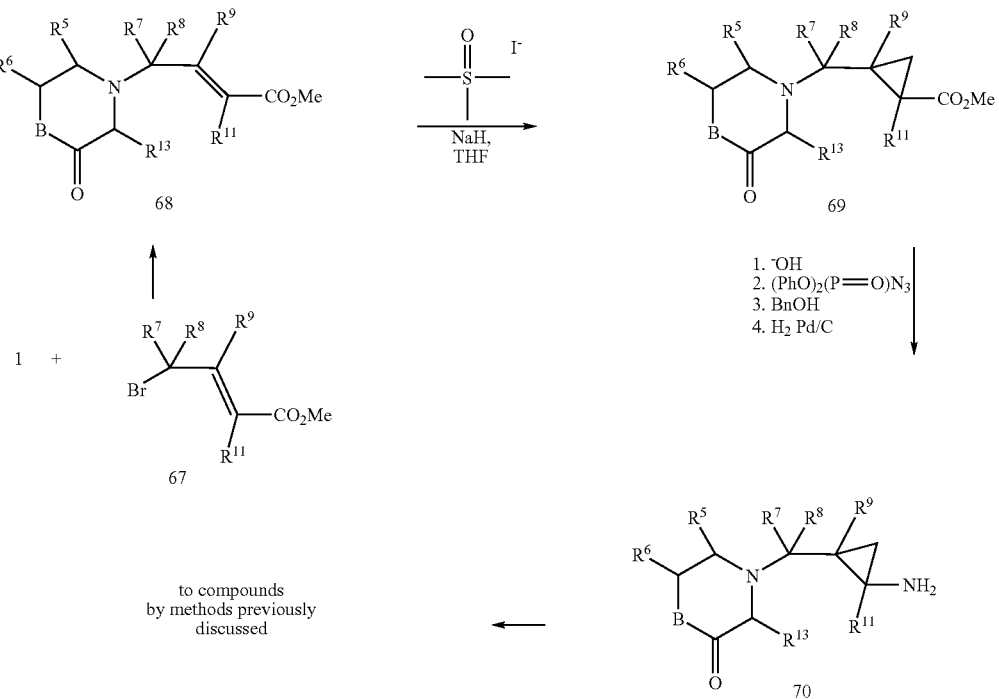

51

Scheme 10

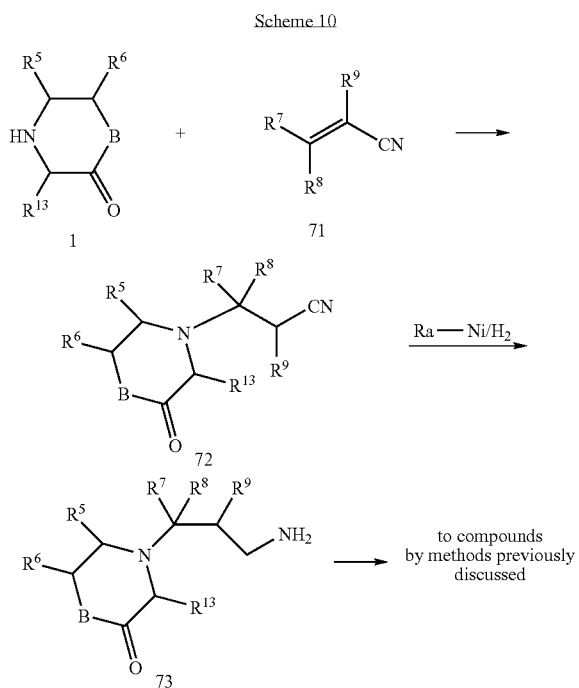

In Schemes 6, 7, and 10, we see that there is no gem-substitution on the alpha-carbon to the electron-withdrawing group of what used to be the Michael acceptor. In other words, in Scheme 6, there is no $R^{10}$ gem to $R^9$; in Scheme 7, there is no $R^{10}$ gem to one of the $R^{9s}$ and in Scheme 10 there is no $R^{10}$ gem to $R^9$. Gem-substitution can be introduced by reacting piperazin-2-one or morpholin-2-one 1 with the epoxide of Michael acceptors 46, 55, and 71 to yield the corresponding alcohols (for amines reacting with epoxides of Michael acceptors, see Charvillon, F. B.; Amouroux, R.; Tet. Lett. 1996, 37, 5103-5106; Chong, J. M.; Sharpless, K. B.; J Org Chem 1985, 50, 1560). These alcohols eventually can be further elaborated into $R^{10}$ by one skilled in the art, as, for example, by tosylation of the alcohol and cuprate displacement (Hanessian, S.; Thavonekham, B.; DeHoff, B.; J. Org. Chem. 1989, 54, 5831), etc., and by other displacement reactions which will be discussed in great detail later on in this application.

Further use of epoxides to synthesize compounds of this invention are shown in Scheme 11. Reaction of piperazin-2-one or morpholin-2-one 1 with epoxide 74 yields protected amino-alcohol 75. This reaction works exceptionaly well when $R^7$ and $R^8$ are H but is not limited thereto. The reaction is performed in an inert solvent at room temperature to the reflux temperature of the solvent. Protecting groups on the nitrogen atom of 74 include BOC and CBZ but are not limited thereto. The hydroxyl group can be optionally protected by a variety of protecting groups familiar to one skilled in the art. Deprotection of the nitrogen gives 76 which can be elaborated to the compounds of this invention by the procedures previously discussed.

Scheme 11

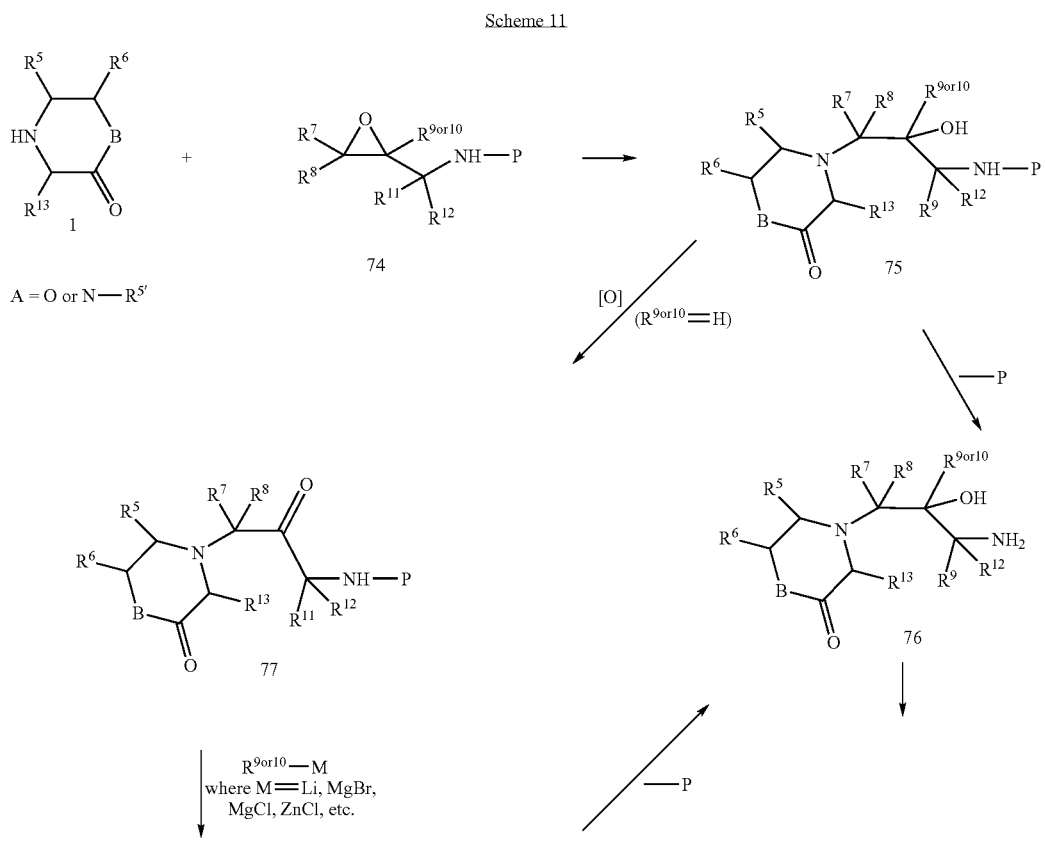

-continued

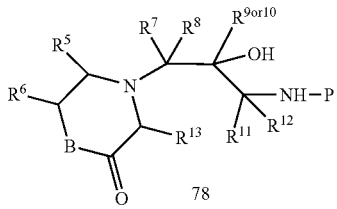

78

If R[9]=H, then oxidation, for example, by using PCC (Corey E. J. and Suggs, J. W., Tet. Lett. 1975, 31, 2647-2650) or with the Dess-Martin periodinane (Dess, D. B. and Martin, J. C., J. Org. Chem. 1983, 48, 4155-4156) yields ketone 77. Ketone 77 may undergo nucleophilic 1,2-addition with organometallic reagents such as alkyl- or aryllithiums, Grignards, or zinc reagents, with or without $CeCl_3$ (T. Imamoto, et al., Tet. Lett. 1985, 26, 4763-4766; T. Imamoto, et al., Tet. Lett. 1984, 25, 4233-4236) in aprotic solvents such as ether, dioxane, or THF to yield alcohol 78. The hydroxyl group can be optionally protected by a variety of protecting groups familiar to one skilled in the art. Deprotection of the nitrogen yields 76 which can be finally elaborated to the compounds of this invention as previously discussed. Epoxides disclosed by structure 74 may be synthesized enantio-selectively from amino acid starting materials by the methods of Dellaria, et al. J Med Chem 1987, 30 (11), 2137, and Luly, et al. J Org Chem 1987, 52 (8), 1487.

The carbonyl group of ketone 77 in Scheme 11 may undergo Wittig reactions followed by reduction of the double bond to yield alkyl, arylalkyl, heterocyclic-alkyl, cycloalkyl, cycloalkylalkyl, etc. substitution at that position, reactions that are familiar to one skilled in the art. Wittig reagents can also contain functional groups which after reduction of the double bond yield the following functionality: esters (Buddrus, J. Angew Chem., 1968, 80), nitrites (Cativiela, C. et al., Tetrahedron 1996, 52 (16), 5881-5888.), ketone (Stork, G. et al., J Am Chem Soc 1996, 118 (43), 10660-10661), aldehyde and methoxymethyl (Bertram, G. et al., Tetrahedron Lett 1996, 37 (44), 7955-7958.), gamma-butyrolactone Vidari, G. et al., Tetrahedron: Asymmetry 1996, 7 (10), 3009-3020.), carboxylic acids (Svoboda, J. et al., Collect Czech Chem Commun 1996, 61 (10), 1509-1519), ethers (Hamada, Y. et al., Tetrahedron Lett 1984, 25 (47), 5413), alcohols (after hydrogenation and deprotection—Schonauer, K.; Zbiral, E.; Tetrahedron Lett 1983, 24 (6), 573), amines (Marxer, A.; Leutert, T. Helv Chim Acta, 1978, 61) etc., all of which may further undergo transformations familiar to one skilled in the art to form a wide variety of functionality at this position.

Scheme 12

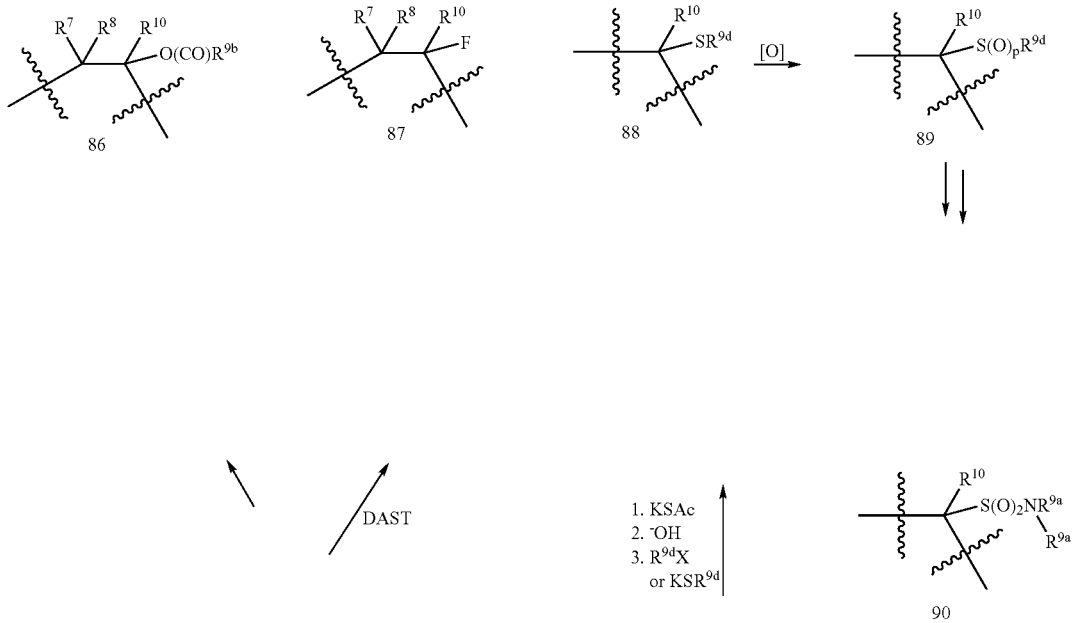

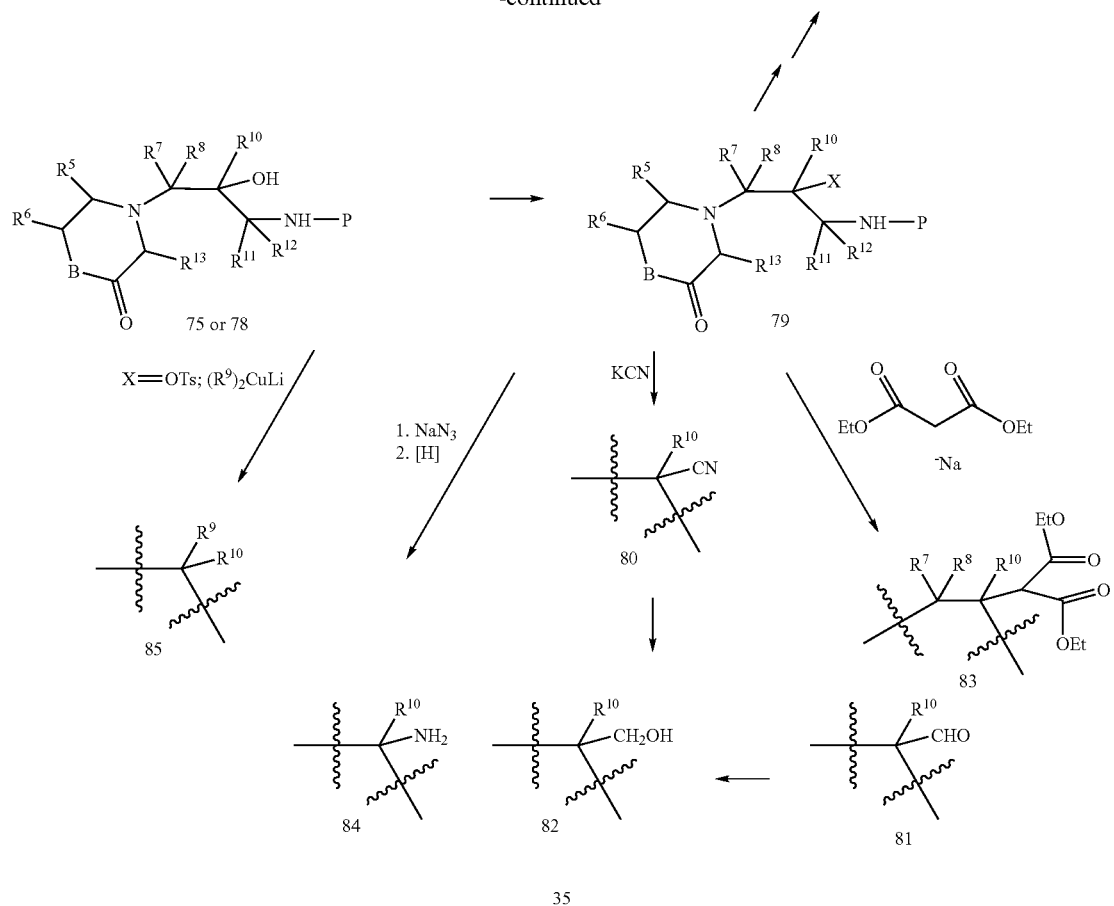

Scheme 12 summarizes the displacement chemistry and subsequent elaborations that can be used to synthesize the $R^9$ groups. In Scheme 12 we see that alcohol 75 or 78 may be tosylated, mesylated, triflated, or converted to a halogen by methods familiar to one skilled in the art to produce compound 79. (Note that all of the following reactions in this paragraph can be also performed on the compounds, henceforth called carbon homologs of 75 or 78 where OH can be $(CH_2)_rOH$ and it is also understood that these carbon homologs may have substituents on the methylene groups as well). For example, a hydroxyl group may be converted to a bromide by $CBr_4$ and $Ph_3P$ (Takano, S. Heterocycles 1991, 32, 1587). For other methods of converting an alcohol to a bromide or to a chloride or to an iodide see R. C. Larock, Comprehensive Organic Transformations, VCH Publishers, New York, 1989, pp. 354-360. Compound 79 in turn may be displaced by a wide variety of nucleophiles as shown in Scheme 12 including but not limited to azide, cyano, malonate, cuprates, potassium thioacetate, thiols, amines, etc., all nucleophilic displacement reactions being familiar to one skilled in the art. Tosylate 79 can undergo displacement with cuprates to yield 85 (Hanessian, S.; Thavonekham, B.; DeHoff, B.; J. Org. Chem. 1989, 54, 5831). Halide, mesylate, tosylate or triflate 79 can undergo displacement with azide followed by reduction to yield amine 84 a procedure familiar to one skilled in the art. Displacement by malonate yields malonic ester 83. Displacement by nitrile yields a one-carbon homologation product 80. Nitrile 80 can be reduced with DIBAL to yield aldehyde 81. This aldehyde can undergo reduction to alcohol 82 with, for example, $NaBH_4$ which in turn can undergo all of the $SN_2$ displacement reactions mentioned for alcohol 75 or 78.

Alcohol 75 or 78, 82, or 97, can be acylated by procedures familiar to one skilled in the art, for example, by Schotten-Baumann conditions with an acid chloride or by an anhydride with a base such as pyridine to yield 86. Alcohol 82 is a one carbon homolog of alcohol 75 or 78. Thus one can envision taking alcohol 82, converting it to a leaving group X as discussed above for compound 75 or 78, and reacting it with NaCN or KCN to form a nitrile, subsequent DIBAL reduction to the aldehyde and subsequent $NaBH_4$ reduction to the alcohol resulting in a two carbon homologation product. This alcohol can undergo activation followed by the same $SN_2$ displacement reactions discussed previously, ad infinitum, to result in 3,4,5 . . . etc. carbon homologation products.

Alcohols may be converted to the corresponding fluoride 87 by DAST (diethylaminosulfur trifluoride) (Middleton, W. J.; Bingham, E. M.; Org. Synth. 1988, VI, pg. 835). Sulfides 88 can be converted to the corresponding sulfoxides 89 (p=1) by sodium metaperiodate oxidation (N. J. Leonard, C. R. Johnson J. Org. Chem. 1962, 27, 282-4) and to sulfones 89 (p=2) by Oxone® (A. Castro, T. A. Spencer J. Org. Chem. 1992, 57, 3496-9). Sulfones 89 can be converted to the corresponding sulfonamides 90 by the method of H.-C. Huang, E. et al., Tet. Lett. (1994) 35, 7201-7204 which involves first, treatment with base followed by reaction with a trialkylborane yielding a sulfinic acid salt which can be reacted with hydroxylamine-O-sulfonic acid to yield a sulfonamide. Another route to sulfonamides involves reaction of amines with a sulfonyl chloride (G. Hilgetag and A. Martini, Preparative Organic Chemistry, New York: John Wiley and Sons, 1972, p. 679). This sulfonyl chloride (not shown in Scheme 12) can be obtained from the corresponding sulfide (88 where $R^9d$=H in Scheme 12, the hydrolysis product after thioacetate displacement), disulfide, or isothiouronium salt by simply reacting with chlorine in water. The isothiouronium salt may be synthesized from the corresponding halide, mesylate or tosylate 79 via reaction with thiourea (for a discussion on the synthesis of sulfonyl chlorides see G. Hilgetag and A. Martini, ibid., p. 670).

As shown in Scheme 13 Aldehyde 81 can also be reacted with a lithium or Grignard reagent to form an alcohol 91 which can also undergo the above displacement reactions. Oxidation by methods familiar to one skilled in the art yields ketone 92. Malonic ester 83 can be saponified and decarboxylated to yield carboxylic acid 93, a two carbon homologation product. Conversion to ester 94 (A. Hassner and V. Alexanian, Tet. Lett, 1978, 46, 4475-8) and reduction with LAH yields alcohol 97 which can undergo all of the displacement reactions discussed for alcohol 75 or 78.

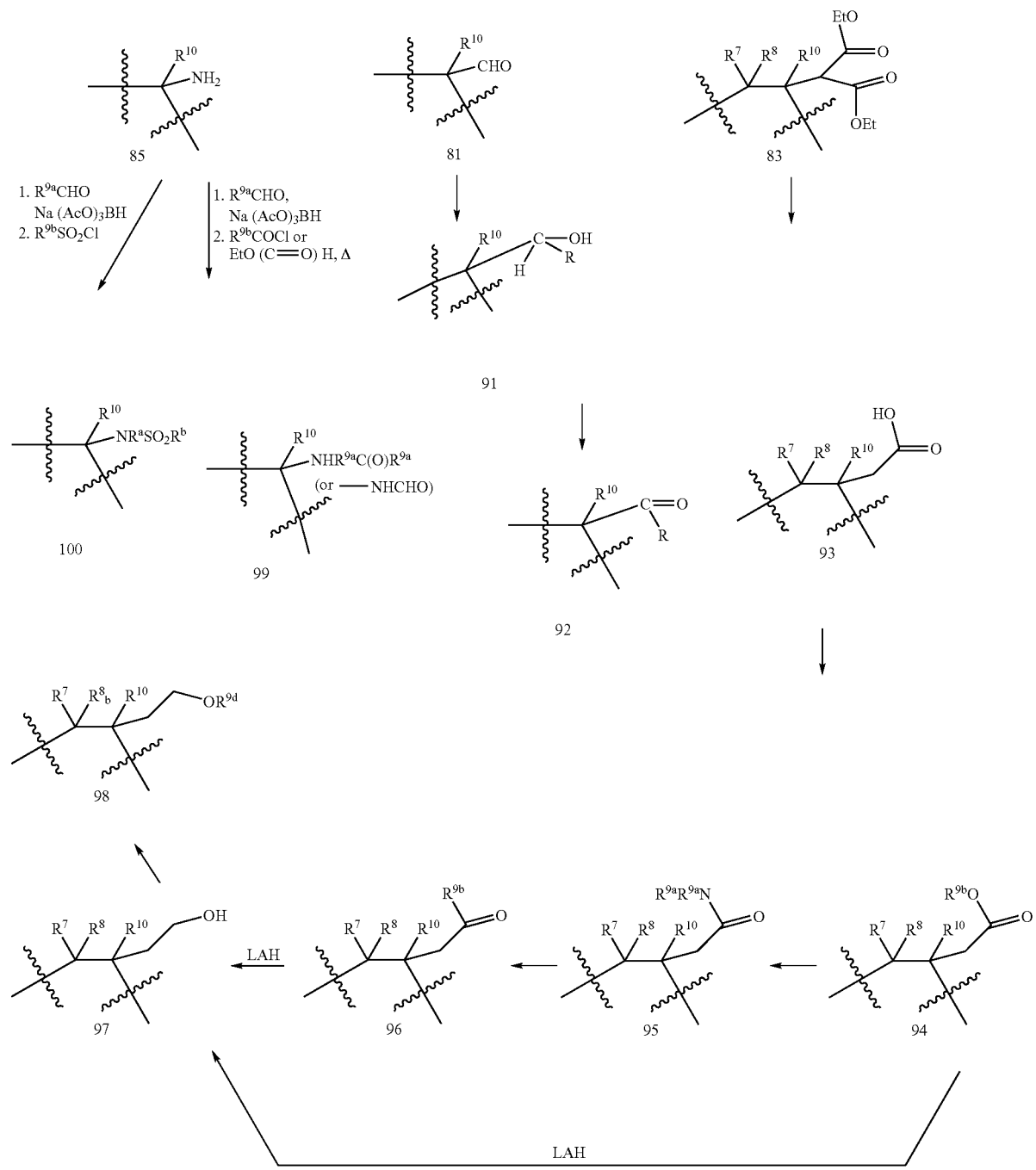

Scheme 13

Carboxylic acid 93 can be converted to amides 95 by standard coupling procedures or via an acid chloride by Schotten-Baumann chemistry or to a Weinreb amide (95: $R^{9a}$=OMe, $R^{9a}$=Me in Scheme 13) (S. Nahm and S. M. Weinreb, Tet. Lett., 1981, 22, 3815-3818) which can undergo reduction to an aldehyde 96 ($R^9$b=H in Scheme 13) with LAH (S. Nahm and S. M. Weinreb, ibid.) or reactions with Grignard reagents to form ketones 96 (S. Nahm and S. M. Weinreb, ibid.). The aldehyde 96 obtained from the Weinreb amide reduction can be reduced to the alcohol with $NaBH_4$. The aldehyde or ketone 96 (or 81 or 92 for that matter) can undergo Wittig reactions as discussed previously followed by optional catalytic hydrogenation of the olefin. This Wittig sequence is one method for synthesizing the carbocyclic and heterocyclic substituted systems at $R^9$ employing the appropriate carbocyclic or heterocyclic Wittig (or Horner-Emmons) reagents. Of course, the Wittig reaction may also be used to synthesize alkenes at $R^9$ and other functionality as well. Ester 94 can also form amides 95 by the method of Weinreb (A. Basha, M. Lipton, and S. M. Weinreb, Tet. Lett. 1977, 48, 4171-74) (J. I. Levin, E. Turos, S. M. Weinreb, Syn. Comm. 1982, 12, 989-993). Alcohol 97 can be converted to ether 98 by procedures familiar to one skilled in the art, for example, NaH, followed by an alkyliodide or by Mitsunobu chemistry (Mitsunobu, O. Synthesis, 1981, 1-28). Amine 84 can again undergo optional reductive amination followed by reaction with a sulfonyl chloride to yield 100, for example under Schotten-Baumann conditions as discussed previously. This amine can undergo optional reductive amination and acylation to yield 99 or reaction with ethyl formate (usually refluxing ethyl formate) to yield formamide 99. This same sequence may be employed for amine obtained from the reduction of nitrile 80.

Aldehyde 81 or its homologous extensions can be reacted with a carbon anion of an aryl (phenyl, naphthalene, etc.) or heterocyclic group to yield an aryl alcohol or a heterocyclic alcohol. If necessary, $CeCl_3$ may be added (T. Imamoto, et al., Tet. Lett. 1985, 26, 4763-4766; T. Imamoto, et al., Tet. Lett. 1984, 25, 4233-4236). This alcohol may be reduced with $Et_3SiH$ and TFA (J. Org. Chem. 1969, 34, 4; J. Org. Chem. 1987, 52, 2226). These aryl and heterocyclic anions may also be alkylated by 79 (or its carbon homolog) to yield compounds where $R^9$ contains an aryl or heterocyclic group. Compound 79 or its carbon homologs may be alkylated by an alkyne anion to produce alkynes at $R^9$ (see R. C. Larock, Comprehensive Organic Transformations, New York, 1989, VCH Publishers, p 297). In addition, carboxaldehyde 81 or its carbon homologs can undergo 1,2-addition by an alkyne anion (Johnson, A. W. The Chemistry of Acetylenic Compounds. V. 1. "Acetylenic Alcohols," Edward Arnold and Co., London (1946)). Nitro groups can be introduced by displacing bromide 79 (or its carbon homologs) with sodium nitrite in DMF (J. K. Stille and E. D. Vessel J. Org. Chem. 1960, 25, 478-490) or by the action of silver nitrite on iodide 79 or its carbon homologs (Org. Syntheses 34, 37-39).

If an anion is made of the piperazin-2-one or morpholin-2-one 1 with LDA or n-BuLi, etc., then that anion in a suitable nonhydroxylic solvent such as THF, ether, dioxane, etc., can react in a Michael-type fashion (1,4-addition) with an alpha, beta-unsaturated ester to yield an intermediate enolate which can be quenched with an electrophile ($R^9$X) (where X is as described in Scheme 1) (Uyehara, T.; Asao, N.; Yamamoto, Y.; J Chem Soc, Chem Commun 1987, 1410) as shown in Scheme 14.

It is to be understood that $R^9$ is either in its final form or in a suitable protected precursor form. This electrophile can be a carbon-based electrophile, some examples being formaldehyde to introduce a $CH_2OH$ group, an aldehyde or a ketone which also introduces a one-carbon homologated alcohol, ethylene oxide (or other epoxides) which introduces a —$CH_2CH_2OH$ group (a two-carbon homologated alcohol), an alkyl halide, etc., all of which can be later elaborated into $R^9$.

It can also be an oxygen-based electrophile such as MCPBA, Davis' reagent (Davis, F. A.; Haque, M. S.; J Org Chem 1986, 51 (21), 4083; Davis, F. A.; Vishwaskarma, L. C.; Billmers, J. M.; Finn, J.; J Org Chem 1984, 49, 3241) or $MoO_5$ (Martin, T. et al., J Org Chem 1996, 61 (18), 6450-6453) which introduces an OH group. These OH groups can undergo the displacement reactions discussed previously in Scheme 12 or protected by suitable protecting groups and deprotected at a later stage when the displacement reactions decribed in Scheme 12 can be performed. In addition, these hydroxyl groups can also undergo displacement reactions to introduce N- or C-substituted heterocycles at this position.

Ester 102 can be converted into its Weinreb amide 104 (S. Nahm and S. M. Weinreb, Tet. Lett., 1981, 22, 3815-3818) or Weinreb amide 104 can be synthesized via Michael-type addition of 1 to alpha,beta-unsaturated Weinreb amide 105. Subsequent reaction with a Grignard reagent forms ketone 107. This ketone can also be synthesized in one step directly from the piperazin-2-one or morpholin-2-one 1 and alpha,beta-unsaturated ketone 106 using the same procedure. This ketone may be reduced with LAH, $NaBH_4$ or other reducing agents to form alcohol 108. Or else, ketone 107 can be reacted with an organolithium or Grignard reagents to form tertiary alcohol 109. Or else, ester 102 can be directly reduced with $LiBH_4$ or LAH to yield primary alcohol 110.

Alcohols 108, 109, and 110 can all be tosylated, mesylated, triflated, or converted to a halogen by methods discussed previously and displaced with an amine nucleophile such as azide, diphenylphosphoryl azide (with or without DEAD and $Ph_3P$), phthalimide, etc. as discussed previously (and which are familiar to one skilled in the art) and after reduction (azide) or deprotection with hydrazine (phthalimide), for example, yield the corresponding amines. These can then be elaborated into the compounds of this invention as discussed previously.

Scheme 14

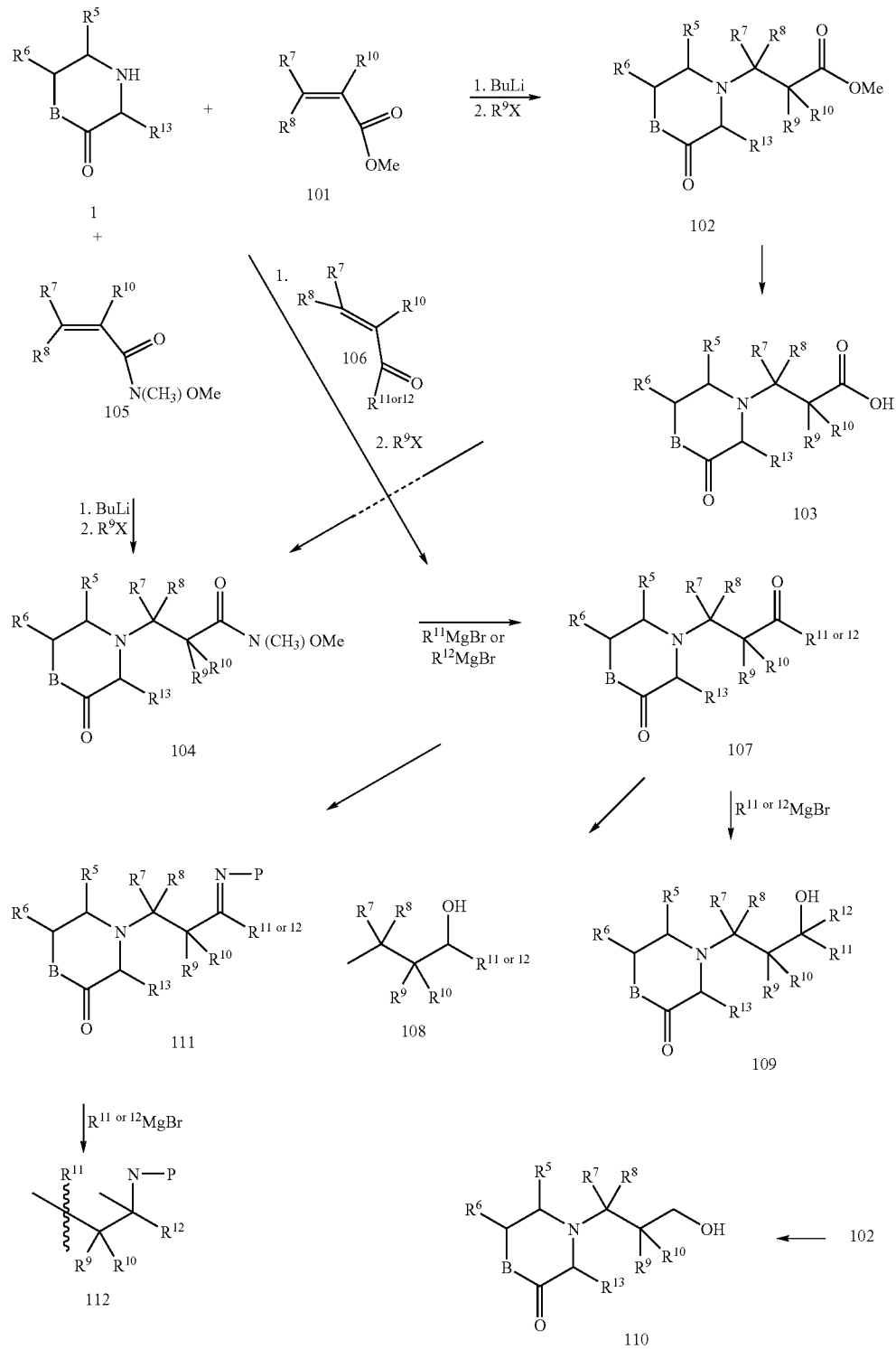

Ketone 107 can also be converted into imine 111 which can be reacted with a Grignard reagent or lithium reagent, etc., to form a protected amine 112 which can be deprotected and elaborated into the compounds of this invention as discussed previously. Some protecting groups include benzyl, substituted benzyls, which can be removed by hydrogenation, and cyanoethyl, which can be removed with aqueous base, etc. It is to be understood that $R^{7-12}$ in Scheme 10 can be in their final form or in precursor form which can be elaborated into final form by procedures familiar to one skilled in the art.

Magnesium amides of amines have been used to add in a Michael-type manner to alpha,beta-unsaturated esters where the substituents at the beta position of the unsaturated ester are tied together to form a cyclopentane ring (for example, compound 101 where $R^7$ and $R^8$ are taken together to be —$(CH_2)_4$—) (Kobayashi, K. et al., Bull Chem Soc Jpn, 1997, 70 (7), 1697-1699). Thus reaction of piperazin-2-one or morpholin-2-one 1 with cycloalkylidine esters 101 as in Scheme 14 yields esters 102 where $R^7$ and $R^8$ are taken together to form a cycloalkyl ring. Subsequent elaboration yields compounds of this invention where $R^7$ and $R^8$ are taken together to form a cycloalkyl ring.

azide, DEAD, and triphenylphosphine (Saito, A. et al., Tet. Lett. 1997, 38 (22), 3955-3958) yields azidoalcohol 115. Hydrogenation over a Pd catalyst yields aminoalcohol 116. This can be protected in situ or in a subsequent step with $BOC_2O$ to put on a BOC protecting group, or with CBZ-Cl and base to put on a CBZ-group or other protecting groups. Alternatively, the amino group can be reacted with an isocyanate, an isothiocyanate, a carbamoyl chloride, or any reagent depicted in Scheme 1 to form 117, which can be alkylated with 1 to form the compounds of this invention.

Scheme 15

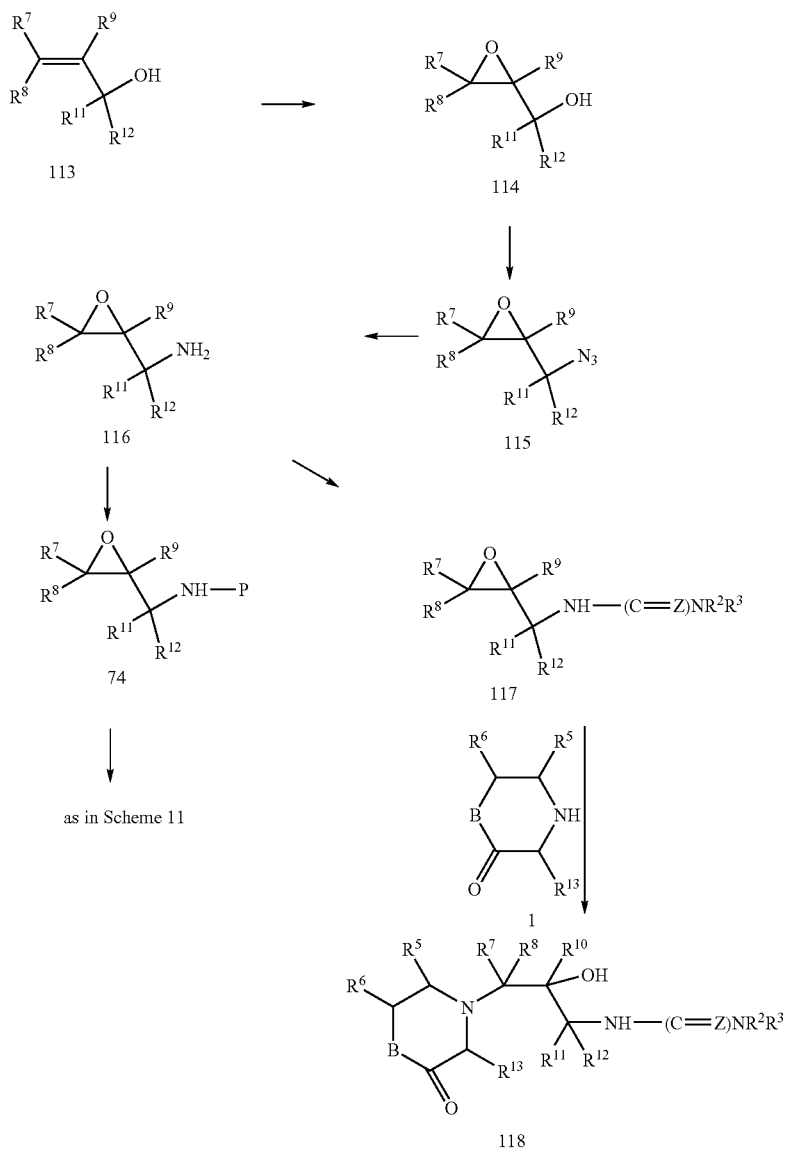

Compounds of structure 118 may also be synthesized from epoxyalcohols as shown in Scheme 15. Allylic alcohol 113 can be epoxidized either stereoselectively using $VO(acac)_2$ catalyst (for a review, see Evans: Chem. Rev. 1993, 93, 1307) or enantioselectively (Sharpless: J. Am. Chem. Soc. 1987, 109, 5765) to epoxyalcohol 114. $S_N2$ displacement of the alcohol using zinc azide and triphenylphosphine (Yoshida, A. J. Org. Chem. 57, 1992, 1321-1322) or diphenylphosphoryl Sometimes the epoxide ring have to be activated with Lewis acids in order for the piperazin-2-one or morpholin-2-one 1 to open the ring (Fujiwara, M.; Imada, M.; Baba, A.; Matsuda, H.; Tetrahedron Lett 1989, 30, 739; Caron, M.; Sharpless, K. B.; J Org Chem 1985, 50, 1557) or 1 has to be deprotonated and used as a metal amide, for example the lithium amide (Gorzynski-Smith, J.; Synthesis 1984 (8), 629)

or MgBr amide (Carre, M. C.; Houmounou, J. P.; Caubere, P.; Tetrahedron Lett 1985, 26, 3107) or aluminum amide (Overman, L. E.; Flippin, L. A.; Tetrahedron Lett 1981, 22, 195).

The quaternary salts ($R^{19}$ is a substituent) of piperazin-2-one or morpholin-2-one can be synthesized by simply reacting the amine with an alkylating agent. Suitable alkylating agent are methyl iodide, methyl bromide, ethyl iodide, ethyl bromide, ethyl or methyl bromoacetate, bromoacetonitrile, allyl iodide, allylbromide, benzyl bromide, etc. Suitable solvents for these reactions include THF, DMF, DMSO, etc. and can be carried our at room temperature to the reflux temperature of the solvent.

Spiroquaternary salts, such as 119, 121, 123, or 125 can be synthesized in a similar manner, the only difference being that the alkylating agent is located intramolecularly as shown in Scheme 16. It is understood by one skilled in the art that functional groups might not be in their final form to permit cyclization to the quaternary ammonium salt and might have to be in precursor form or in protected form to be elaborated to their final form at a later stage. For example, the $NR^1(C=Z)NR^2R^3$ group on the rightmost phenyl ring of compound 124 might exist as a nitro group precursor for ease of manipulation during quaternary salt formation. Subsequent reduction and $NR^1(C=Z)NR^2R^3$ group formation yields product 125. The leaving groups represented by X in Scheme 16 may equal those represented in Scheme 1, but are not limited thereto. N-oxides of piperazin-2-one or morpholin-2-one can be made by the procedure of L. W. Deady (Syn. Comm. 1977, 7, 509-514). This simply entails reacting the piperazin-2-one or morpholin-2-one with MCPBA, for example, in an inert solvent such as methylene chloride.

Scheme 16

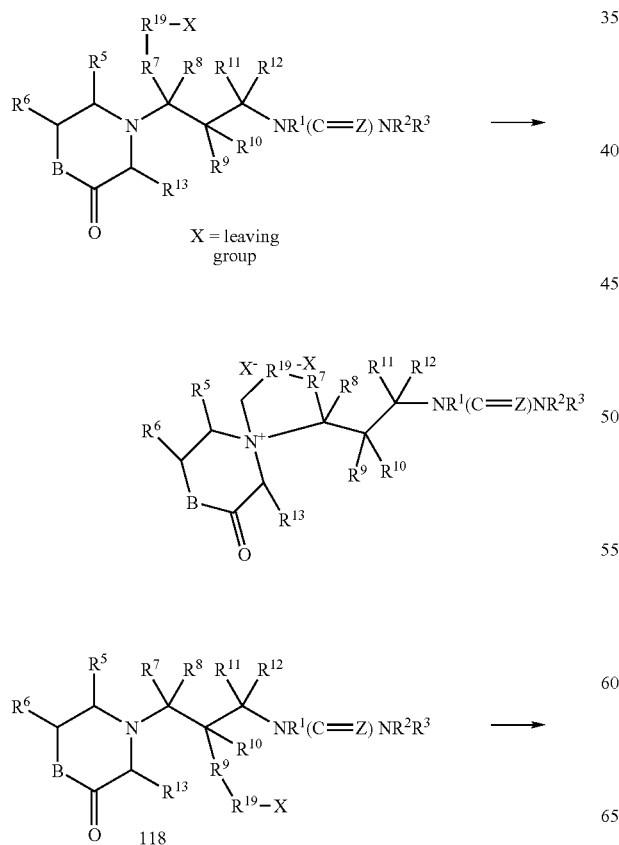

-continued

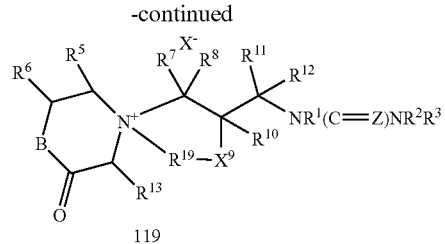

119

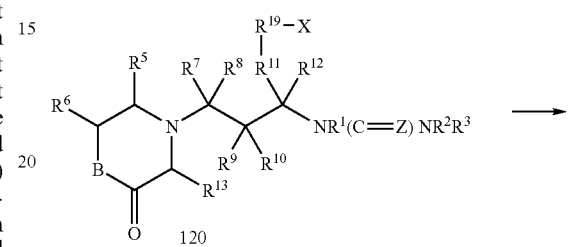

120

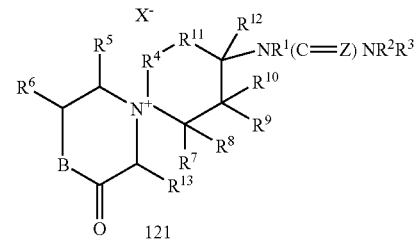

121

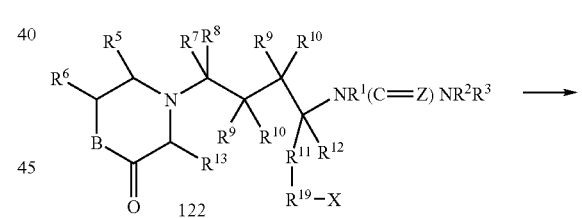

122

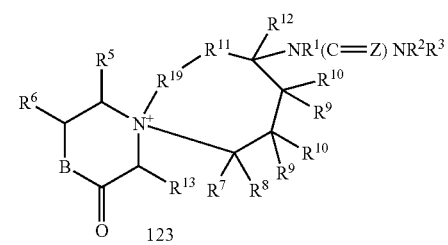

123

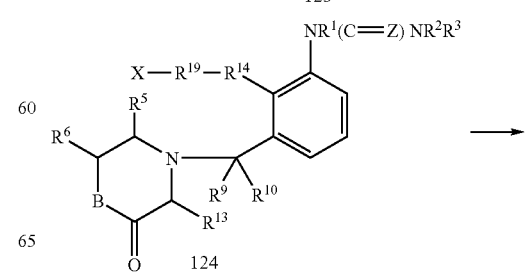

124

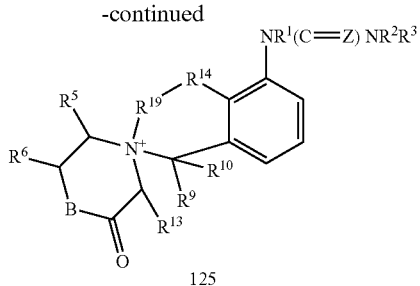

125

Compounds where $R^9$ and $R^{10}$ form a cyclic 3,4,5,6, or 7-membered ring can be synthesized by the methods disclosed in Scheme 17. These same methods may also be used to synthesize gem-disubstituted compounds in which $R^9$ can be different from $R^{10}$ by step-wise alkylation of the malonate derivative. Of course, this scheme may also be used to synthesize compounds where $R^{10}$=H. For example, a cyclohexyl-fused malonate may be synthesized by Michael addition and alkylation of I(CH$_2$)$_4$CH=CCO$_2$Me with dimethyl malonate employing NaH/DMF (Desmaele, D.; Louvet, J.-M.; Tet Lett 1994, 35 (16), 2549-2552) or by a double Michael addition (Reddy, D. B., et al., Org. Prep. Proced. Int. 24 (1992) 1, 21-26) or by an alkylation followed by a second intromolecular alkylation employing an iodoaldehyde (Suami, T.; Tadano, K.; Kameda, Y.; Iimura, Y.; Chem Lett 1984, 1919), or by an alkylation followed by a second intramolecular alkylation employing an alkyl dihalide (Kohnz, H.; Dull, B.; Mullen, K.; Angew Chem 1989, 101 (10), 1375), etc.

Subsequent monosaponification (Pallai, P. V., Richman, S., Struthers, R. S., Goodman, M. Int. J. Peptide Protein Res. 1983, 21, 84-92; M. Goodman Int. J. Peptide Protein Res. 19831, 17, 72-88), standard coupling with piperazin-2-one or morpholin-2-one 1 yields 128. Reduction with borane yields 129 followed by reduction with LAH yields 130 which can be then converted to amine 131 and then to the compounds of this invention by procedures as discussed previously. Ester 129 can also be converted to a Weinreb amide and elaborated to the compounds of this invention as described in Scheme 14 for ester 102 which would introduce substituents $R^{11}$ and $R^{12}$.

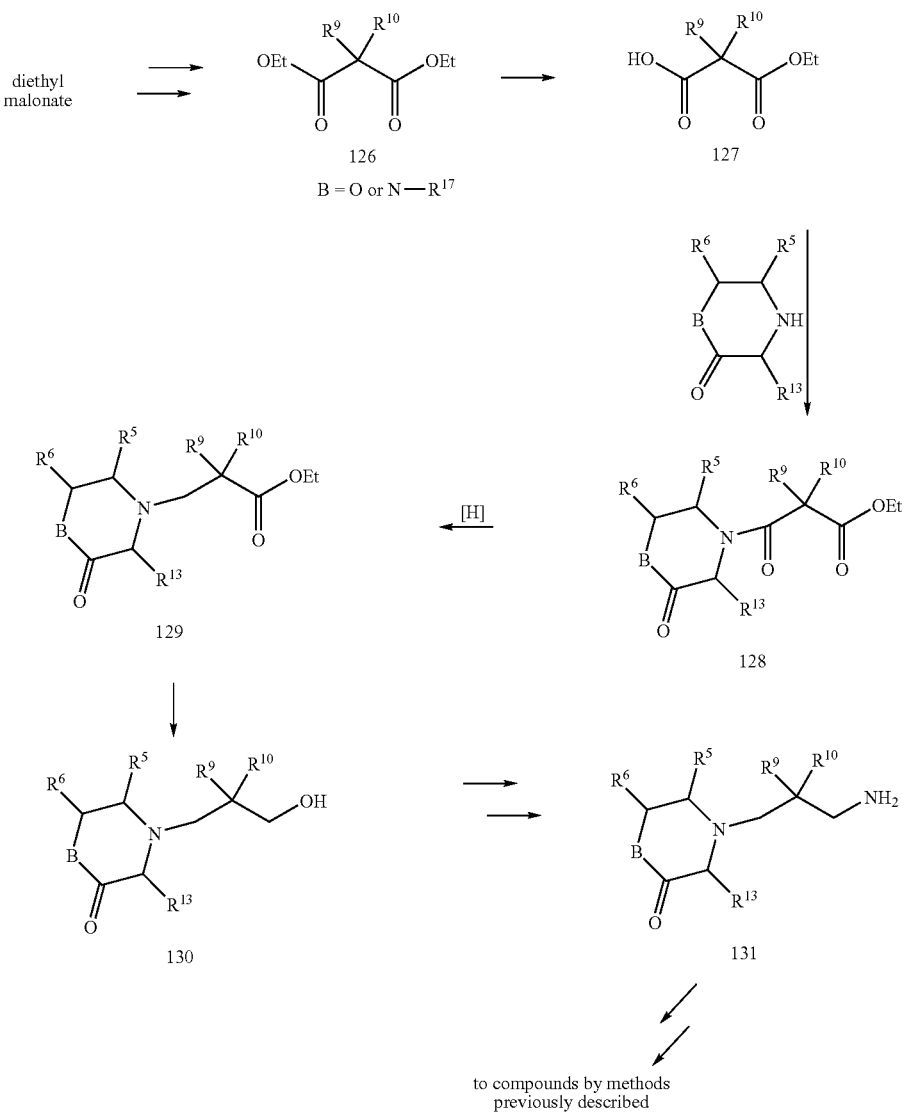

Scheme 18 describes another method for the synthesis of compounds where $R^9$ and $R^{10}$ are taken together to form cycloalkyl groups. Amino alcohols 132 are found in the literature (CAS Registry Nos. for n=0,1,2,3, respectively: 45434-O$_2$-4, 2041-56-7, 2239-31-8, 2041-57-8). They can easily be protected, as with a BOC group (or CBZ, or any other compatible protecting group) by known procedures familiar to one skilled in the art to yield alcohols 133. The alcohols can then be activated by conversion to a halide (or to a mesylate, tosylate or triflate by methods discussed previously), and then alkylated with piperazin-2-one (B=N—$R^{17}$) or morpholin-2-one (B=O) 1 as described in Scheme 1 to yield 135. Subsequent deprotection yields amine 136, which can be elaborated to the compounds of this invention as described previously.

Of course, alcohol 133 can be oxidized to the aldehyde and then reacted with $R^{7or8}$MgBr or $R^{7or8}$Li with or without CeCl$_3$ to yield the corresponding alcohol 133 where instead of —CH$_2$OH, we would have —CHR$^{7or8}$OH. This oxidation-previously. The aldehyde derived from 133 can also undergo reductive amination with 1 to give 135.

A method to introduce cycloalkyl groups at $R^{11}R^{12}$ is shown in Scheme 19. Protection of the nitrogen of compounds 137, which are commercially available, yields 138 (the protecting group may be BOC, CBZ, or any other compatible protecting group) by procedures familiar to one skilled in the art. Esterification by any one of a number procedures familiar to one skilled in the art (for example A. Hassner and V. Alexanian, Tet. Lett, 1978, 46, 4475-8) followed by reduction with DIBAL (or alternatively reduction to the alcohol with, for example, LiBH$_4$, followed by Swern oxidation (op. cit.)) yields aldehyde 139. One carbon homologation via the Wittig reaction followed by hydrolysis of the vinyl ether yields aldehyde 141. Reductive amination (Abdel-Magid, A. F., et al. Tet. Lett. 1990, 31, (39) 5595-5598) yields 142 followed by deprotection yields amine 143

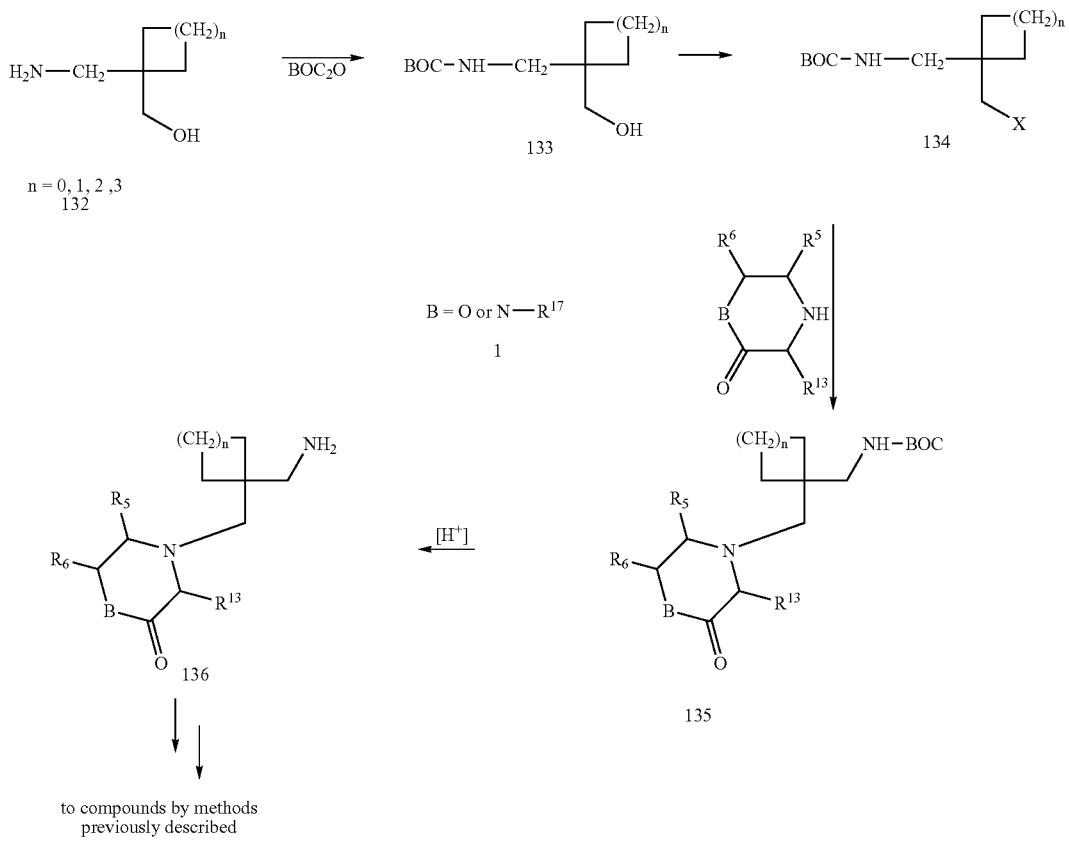

1,2-addition sequence may be repeated to yield a tertiary alcohol. The alcohol may then be tosylated, mesylated, triflated, or converted to Cl, Br, or I to yield 134 and then displaced with piperazin-2-one or morpholin-2-one 1 to yield 135. Subsequent deprotection yields 136, which may undergo elaboration to the compounds of this invention as discussed which can be elaborated to the compounds of this invention by the methods previously discussed. Of course, aldehyde 139 can be reacted with $R^{9or10}$MgBr or $R^{9or10}$Li with or without CeCl$_3$ to yield an alcohol that can be oxidized to a ketone. Wittig one-carbon homologation on this ketone as described above followed by hydrolysis yields 141 where the —CH$_2$CHO is substituted with one R$^{9 or 10}$ group (—CHR$^{9 or 10}$CHO). Aldehyde 141 (—CH$_2$CHO) or its monosubstituted analog synthesized above (—CHR$^{9 or 10}$CHO) can undergo alkylation with R$^{9 or 10}$X where X is as defined in Scheme 1 to yield compound 141 containing one or both of the R$^9$ and R$^{10}$ substituents alpha to the aldehyde group. Alkylation can be performed using LDA or lithium bistrimethylsilyl amide amongst other bases in an inert solvent such as ether, THF, etc., at −78° C. to room temperature. Aldehyde 141 (—CH$_2$CHO) or its substituted analogs synthesized above (i.e., —CHR$^9$R$^{10}$CHO) can undergo reductive amination with 1 and subsequent elaboration to the compounds of this invention. Aldehyde 141 (—CH$_2$CHO) or its substituted analogs synthesized above (i.e., —CHR$^9$R$^{10}$CHO) can also undergo 1,2-addition with R$^{7 or 8}$MgBr or R$^{7 or 8}$Li to yield the corresponding alcohol —CH$_2$CHR$^{7 or 8}$OH or —CHR$^9$R$^{10}$CHR$^{7 or 8}$OH. The alcohol may then be tosylated, mesylated, triflated, or converted to Cl, Br, or I by procedures familiar to one skilled in the art and displaced with piperazin-2-one or morpholin-2-one 1 to yield, after subsequent deprotection and elaboration, the compounds of this invention. Or else alcohol —CH$_2$CHR$^{7 or 8}$OH or —CR$^9$R$^{10}$CHR$^{7 or 8}$OH can be oxidized (i.e., Swern, op. cit.) to the ketone and reductively aminated with 1 and subsequently elaborated to the compounds of this invention. Or else alcohol —CH$_2$CHR$^{7 or 8}$OH or —CR$^9$R$^{10}$CHR$^{7 or 8}$OH can be oxidized (i.e., Swern, op. cit.) to the ketone and reacted once more with R$^{7 or 8}$MgBr or R$^{7 or 8}$Li to yield the corresponding alcohol —CH$_2$CR$^7$R$^8$OH or —CR$^9$R$^{10}$CR$^7$R$^8$OH. If the ketone enolizes easily, CeCl$_3$ may be used together with the Grignard or lithium reagent. The alcohol can again be tosylated, mesylated, triflated, or converted to Cl, Br, or I by procedures familiar to one skilled in the art and displaced with piperazin-2-one or morpholin-2-one 1 to yield, after subsequent deprotection and elaboration, the compounds of this invention. Thus each one of the R$^7$, R$^8$, R$^9$, and R$^{10}$ groups may be introduced into compounds 141, 142 and 143 and, of course, in the compounds of this invention, by the methods discussed above.

The compounds of the present invention in which E contains ring A can be prepared in a number of ways well known to one skilled in the art of organic synthesis. As shown in Scheme 20, reductive amination of aldehyde 148 with monoprotected diamine 147 gives the diprotected triamine 149. The diamine 147 can be synthesized from the α-amino acids via their Weinreb amides 144 as shown in Scheme 20. The Weinreb amide (144: in Scheme 20) (S. Nahm and S. M. Weinreb, Tet. Lett., 1981, 22, 3815-3818) can undergo reduc-

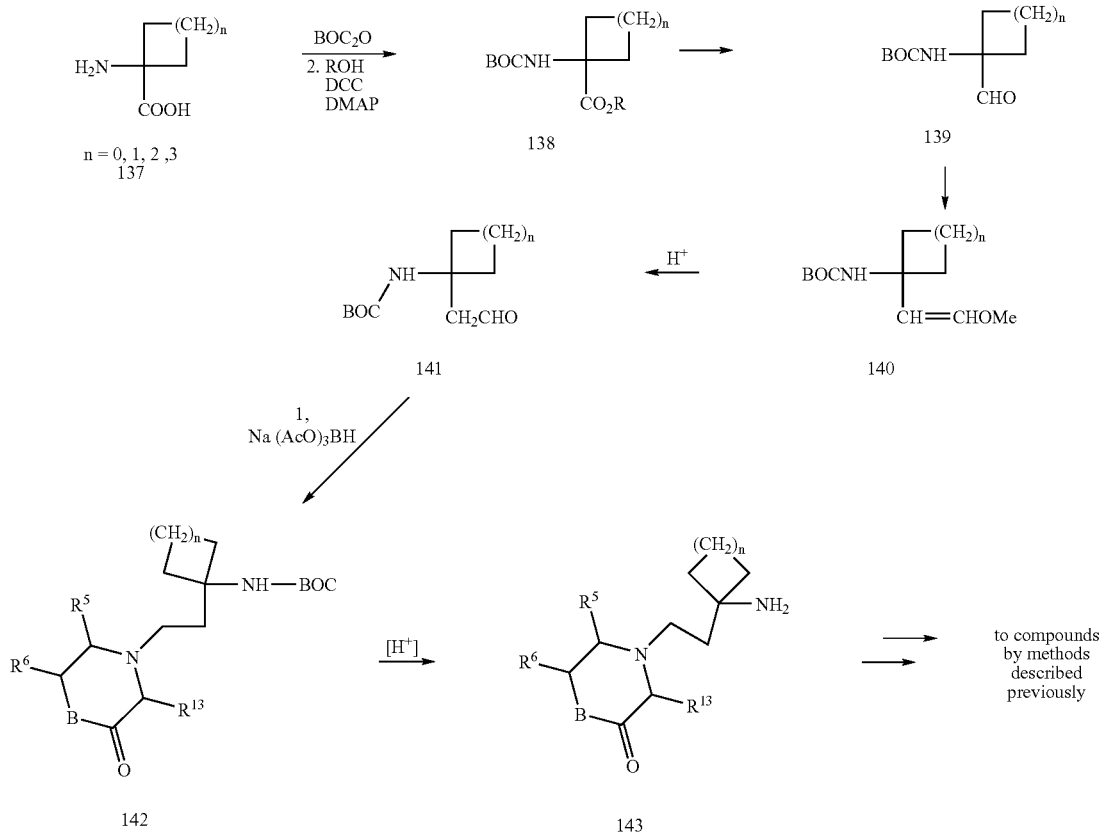

Scheme 19 tion to an aldehyde 145 ($R^6$=H in Scheme 20) with LAH (S. Nahm and S. M. Weinreb, ibid.) or reactions with

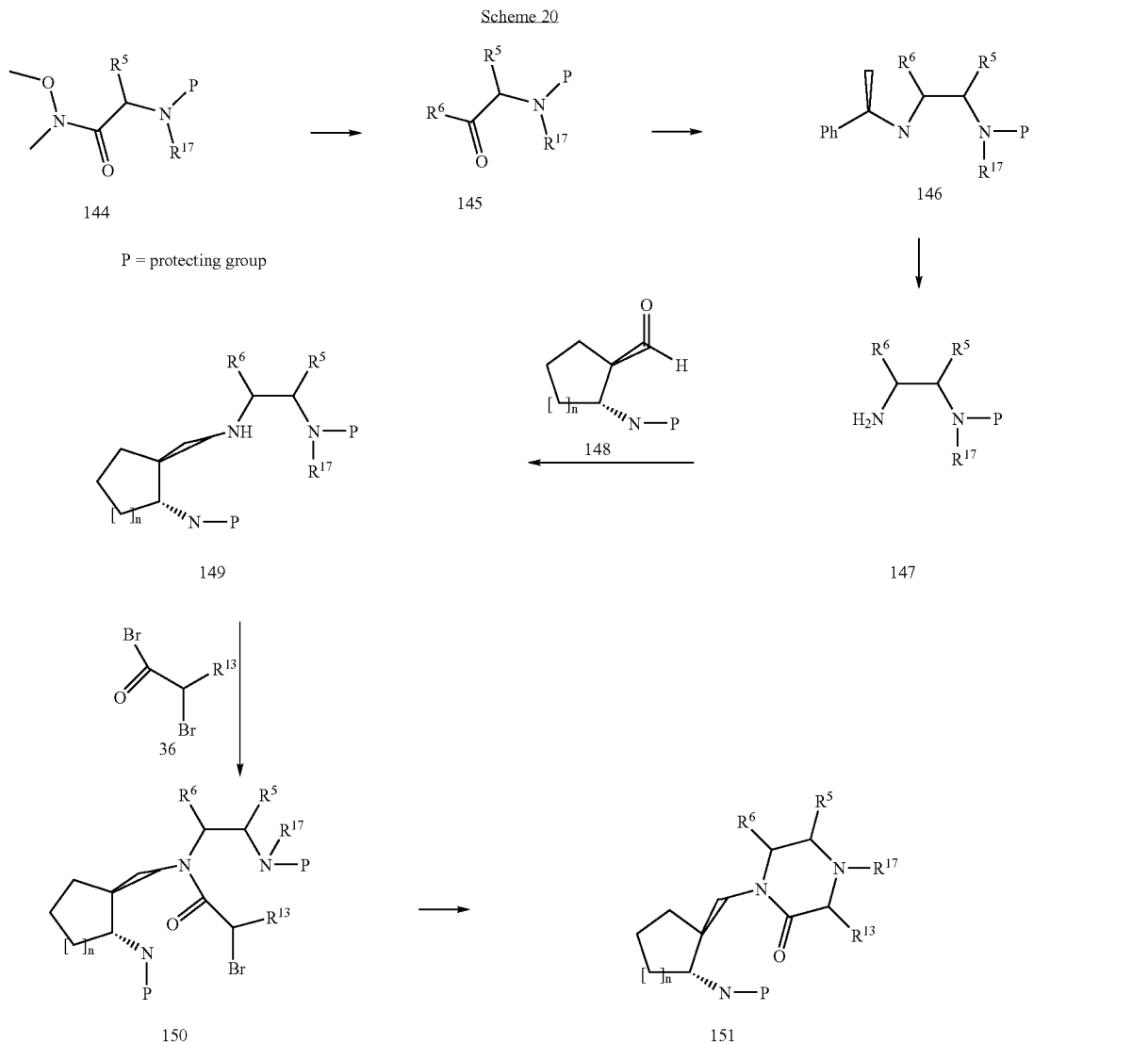

Scheme 20

P = protecting group

Grignard reagents to form ketones 145 (S. Nahm and S. M. Weinreb, ibid.). Reductive amination of the ketone gives the mono-protected diamine 147. The synthesis of 148 can be accomplish from the corresponding known amino acid or amino alcohol (J. Org. Chem. 1996, 61, 5557-63; J. Am. Chem. Soc. 1996, 118, 5502-03). The free amine of 149 can then be acylated with the acyl bromide 36 to give the α-bromo amide 150. Removal of the amino protecting group and cyclization gives the piperazin-3-one 151. Scheme 20 also highlights the synthesis of the isomeric piperazin-3-one instead of the piperazin-2-one that has been exemplified in the previous schemes.

Scheme 21

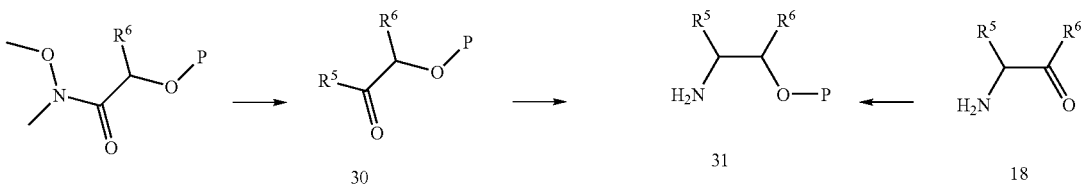

P = protecting group

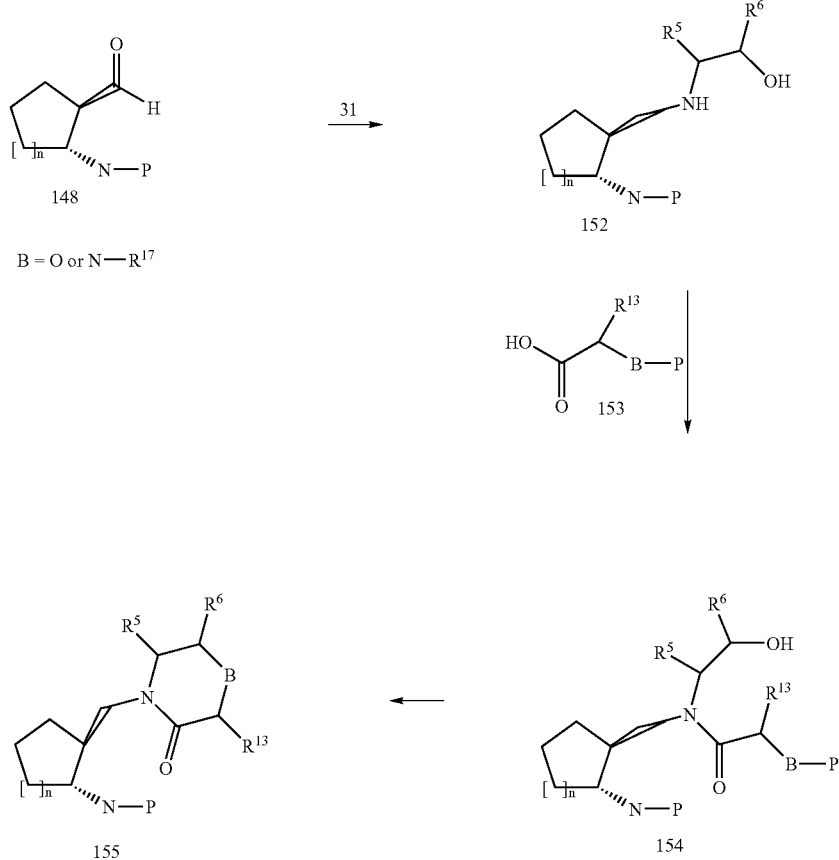

Another method to synthesize the isomeric piperazin-3-ones as well as the isomeric morpholin-3-one analogs (see also 35 in Scheme 3) is shown in Scheme 21. Reductive amination of 148 with amino alcohol 31 gives 152. The free amine is then coupled with the α-amino or α-hydroxy acid derivative 153 to give the amide 154. Conversion of the free hydroxyl group to a good leaving group, removal of the protecting group on a-amino or α-hydroxy amide, and cyclization gives the isomeric piperazin-3-ones or morpholin-3-one analogs 155.

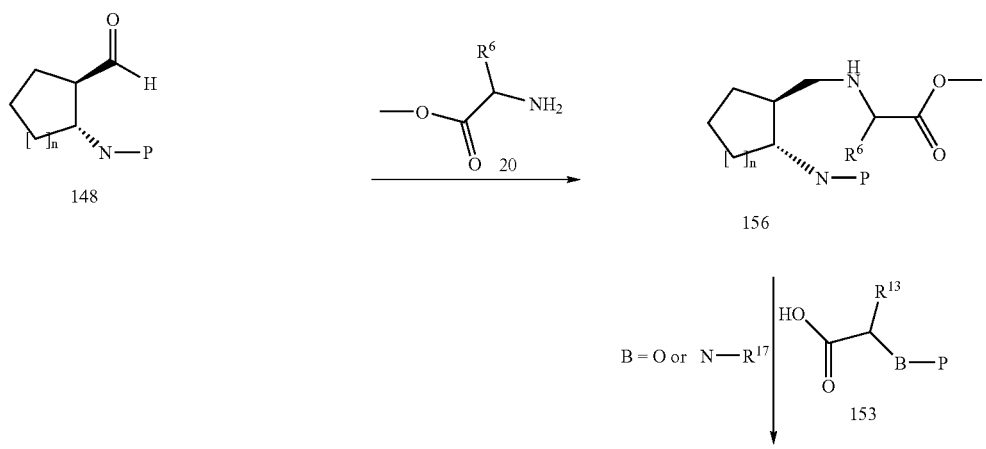

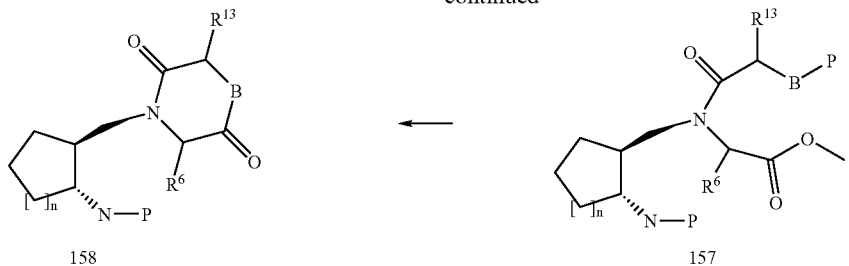

The corresponding diketo-piperazine and diketo-morpholines can also be synthesized using a similar strategy outlined in Scheme 22. Reductive amination of 148 with an α-amino acid ester 20 gives the amino ester 153. This can be coupled with a second α-amino acid or an α-hydroxy acid 153 to give the amide ester 157. Removal of the α-protecting group and cyclization gives the diketo analog 158. Subsequent removal of the amino protecting group of 158 (as well as 155 and 151) gives the free amine which can be elaborated further to compounds of this invention as described in earlier schemes.

Scheme 23

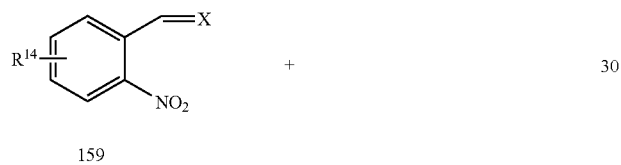

159

+

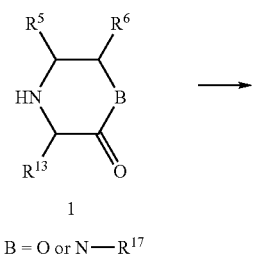

1

B = O or N—R$^{17}$

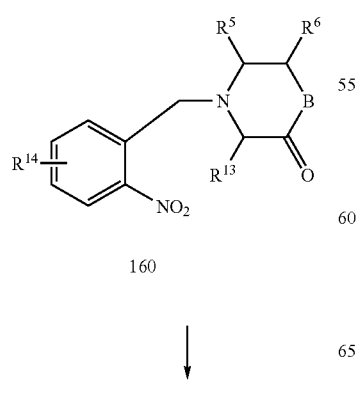

160

↓

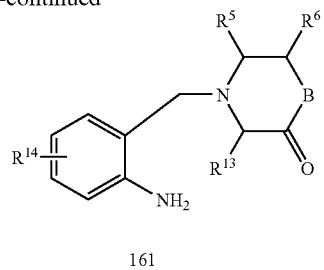

161

Synthesis of examples that incorporate a phenyl group as the carbocycle in linkage E is shown in the next few schemes. Scheme 23 shows the use of a benzyl alkylating agent 159 (X=Br,Cl, mesylate, tosylate, triflate, etc) with piperazin-2-one or morpholin-2-one 1 give the N-benzyl compound 160. The nitro group of 160 is then reduced using catalytic hydrogenation to give the corresponding aniline 161. The aniline amino group can then be elaborated further to compounds of this invention as described in earlier schemes.

As shown in Scheme 24, piperazin-2-one or morpholin-2-one 1 can also be N-alkylated with the phenacyl bromide 162 to give the nitro ketone 163. The nitro group of 163 is then reduced using catalytic hydrogenation to give the corresponding aniline 164. The ketone of 164 can be reduced with NaBH$_4$ to give the alcohol 165. Alternatively, the epoxide 166 can be opened with the piperazin-2-one or morpholin-2-one 1 to give the corresponding nitro benzyl alcohol, which is hydrogenated to give the aniline alcohol 165 directly. The amino group of aniline 164 and 165 can then be elaborated further to compounds of this invention as described in earlier schemes.

Scheme 24
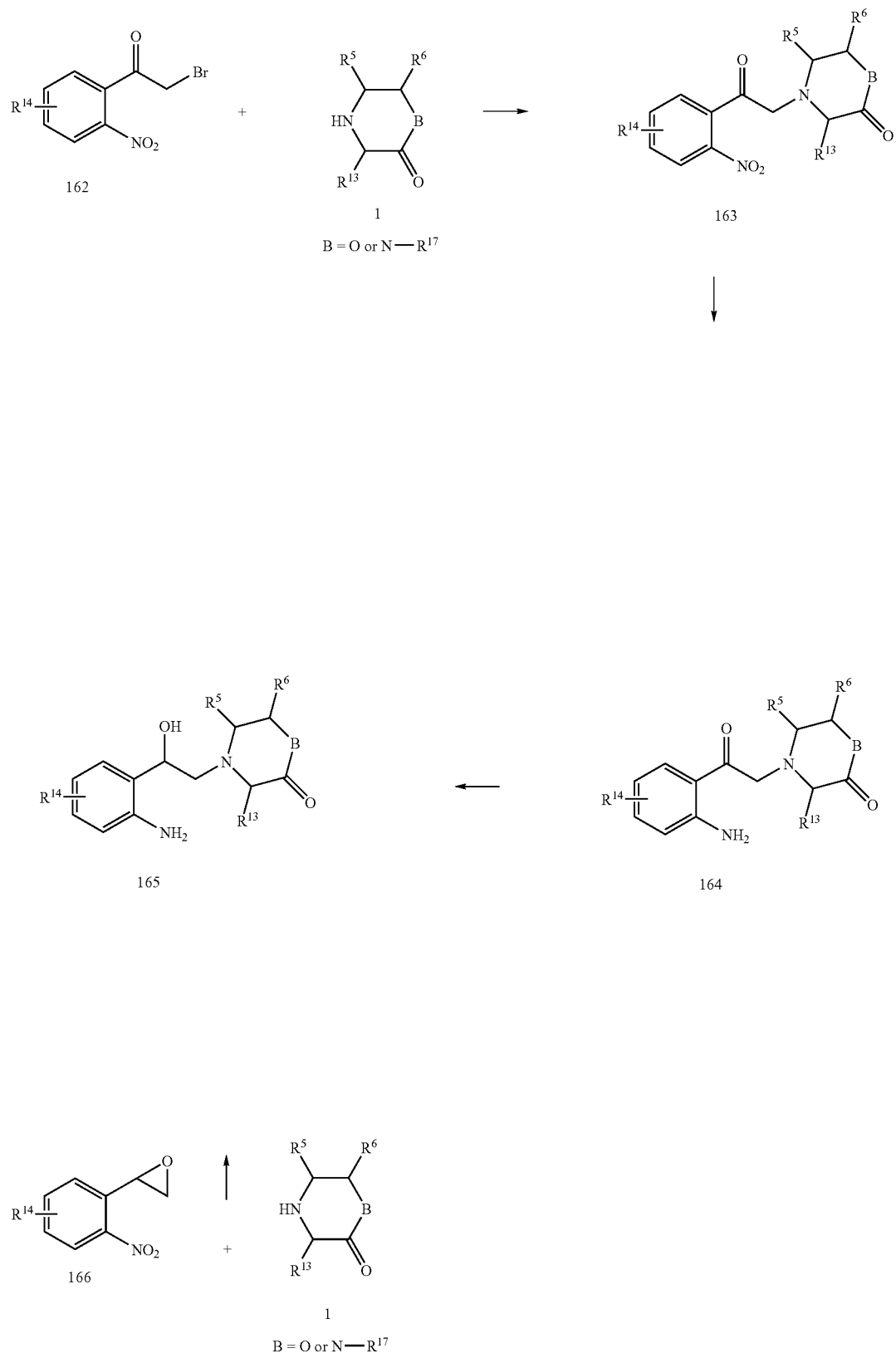

The piperazin-2-one or morpholin-2-one 1 can also be N-alkylated with 3-cyanobenzyl bromide (167, Scheme 25) to give the cyano analog 168. The cyano group is reduced using Raney nickel to give the corresponding benzyl amine 169. The amino group of 169 can then be elaborated further to compounds of this invention 170 as described in earlier schemes.

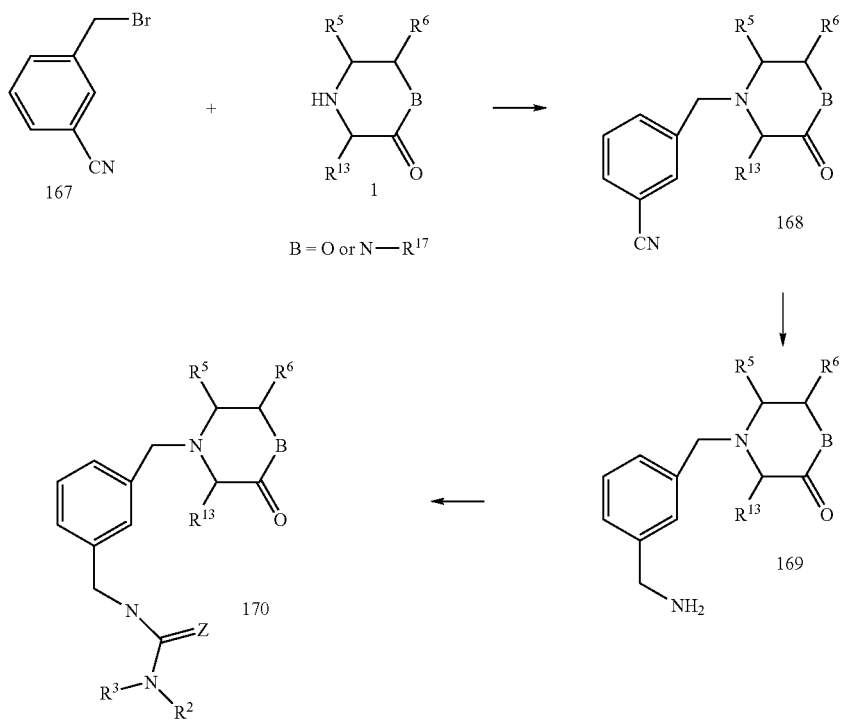

As shown in Scheme 26, 3-cyano aniline can be converted to the urea, thiourea, or other urea isostere as described in previous schemes to give 171. Treatment with HCl/ethanol then converts the cyano group of 171 to the imidate 172. Reaction with piperazin-2-one or morpholin-2-one 1 with the imidate 172 in ethanol then gives the amidine 173.

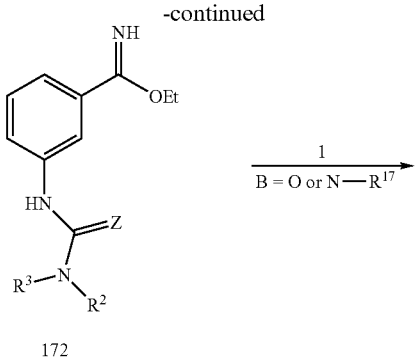

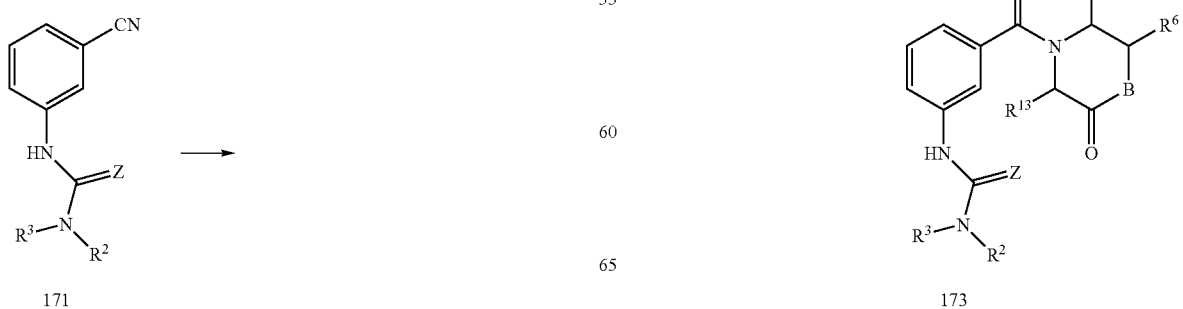

Scheme 27

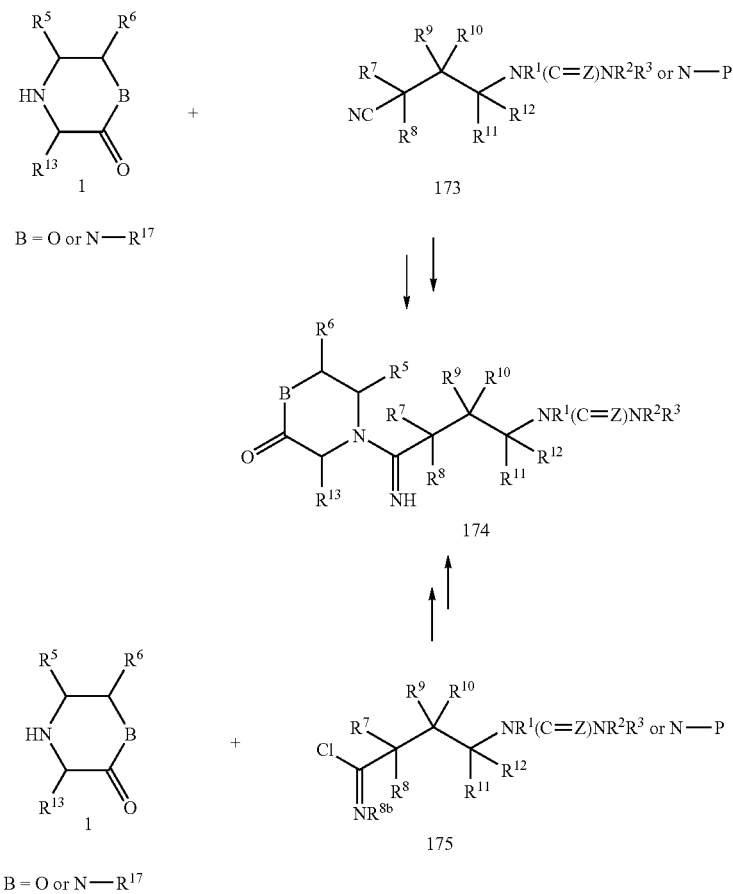

Other methods of synthesizing amidines (compounds where $R^7$ and $R^8$ are taken together to form $=NR^{8b}$) are shown in Scheme 27. Reaction of the piperazin-2-one or morpholin-2-one 1 with nitrile 173 in the presence of CuCl catalysis forms amidine 174 where $R^{8b}$ is H (Rousselet, G.; Capdevielle, P.; Maumy, M.; Tetrahedron Lett. 1993, 34 (40), 6395-6398). Note that the urea portion may be in final form or in precursor form (for example, a protected nitrogen atom; P=protecting group such as STABASE, bis-BOC, etc., as was discussed previously) which may be subsequently elaborated into the compounds of this invention. Compounds 174 may be also synthesized by reacting iminoyl chloride 175 with piperazin-2-one or morpholin-2-one 1 to yield 174 where $R^{8b}$ is not H (Povazanec, F., et al., J. J. Heterocycl. Chem., 1992, 29, 6, 1507-1512). Iminoyl chlorides are readily available from the corresponding amide via $PCl_5$ or $CCl_4/PPh_3$ (Duncia, J. V. et al., J. Org. Chem., 1991, 56, 2395-2400). Again, the urea portion may be in final form or in precursor form.

Syntheses of amines 9, 10, and the amines which are precursors to isocyanates or isothiocyanates 5 will now be discussed. Many amines are commercially available and can be used as 9, 10, or used as precursors to isocyanates or isothiocyanates 5. There are numerous methods for the synthesis of non-commercially available amines familiar to one skilled in the art. For example, aldehydes and ketones may be converted to their O-benzyl oximes and then reduced with LAH to form an amine (Yamazaki, S.; Ukaji, Y.; Navasaka, K.; Bull Chem Soc Jpn 1986, 59, 525). Ketones and trifluoromethylketones undergo reductive amination in the presence of $TiCl_4$ followed by $NaCNBH_4$ to yield amines (Barney, C. L., Huber, E. W., McCarthy, J. R. Tet. Lett. 1990, 31, 5547-5550). Aldehydes and ketones undergo reductive amination with $Na(AcO)_3BH$ as mentioned previously to yield amines (Abdel-Magid, A. F., et al. Tet. Lett. 1990, 31, (39) 5595-5598). Amines may also be synthesized from aromatic and heterocyclic OH groups (for example, phenols) via the Smiles rearrangement (Weidner, J. J., Peet, N. P. J. Het. Chem., 1997, 34, 1857-1860). Azide and nitrile displacements of halides, tosylates, mesylates, triflates, etc. followed by LAH or other types or reduction methods yield amines. Sodium diformyl amide (Yinglin, H., Hongwen, H. Synthesis 1989 122), potassium phthalimide, and bis-BOC-amine anion can all displace halides, tosylates, mesylates, etc., followed by standard deprotection methods to yield amines, procedures which are familiar to one skilled in the art. Other methods to synthesize more elaborate amines involve the Pictet-Spengler reaction, imine/immonium ion Diels-Alder reaction (Larsen, S. D.; Grieco, P. A. J. Am. Chem. Soc. 1985, 107, 1768-69; Grieco, P. A., et al., J. Org. Chem. 1988, 53, 3658-3662; Cabral, J. Laszlo, P. Tet. Lett. 1989, 30, 7237-7238; amide reduction (with LAH or diborane, for example), organometallic addition to imines (Bocoum, A. et al., J. Chem. Soc. Chem. Comm. 1993, 1542-4).

There are many other syntheses of amines like 9 and 10, which are known in the literature. For example, 3-nitrobenzeneboronic acid 176, which is commercially available, and can undergo Suzuki couplings (Suzuki, A. Pure Appl. Chem. 1991, 63, 419) with a wide variety of substituted iodo- or bromo aryls (aryls such as phenyl, naphthalene, etc.), heterocycles, alkyls, akenyls (Moreno-manas, M., et al., J. Org. Chem., 1995, 60, 2396), or alkynes (154, Scheme 28). It can also undergo coupling with triflates of aryls, heterocycles, etc. (Fu, J.-m, Snieckus, V. Tet. Lett. 1990, 31, 1665-1668). Both of the above reactions can also undergo carbonyl insertion in the presence of an atmosphere of carbon monoxide (Ishiyama, et al., Tet. Lett. 1993, 34, 7595). These nitro-containing compounds (178 and 180) can then be reduced to the corresponding amines either via catalytic hydrogenation, or via a number of chemical methods such as $Zn/CaCl_2$ (Sawicki, E. J Org Chem 1956, 21). The carbonyl insertion compounds (181) can also undergo reduction of the carbonyl group to either the CHOH or CH2 linkages by methods already discussed ($NaBH_4$ or $Et_3SiH$, TFA, etc.). These amines can then be converted to isocyanate 5 via the following methods (Nowakowski, J. J Prakt Chem/Chem-Ztg 1996, 338 (7), 667-671; Knoelker, H.-J. et al., Angew Chem 1995, 107 (22), 2746-2749; Nowick, J. S. et al., J Org Chem 1996, 61 (11), 3929-3934; Staab, H. A.; Benz, W.; Angew Chem 1961, 73); to isothiocyanate 5 via the following methods (Strekowski L. et al., J Heterocycl Chem 1996, 33 (6), 1685-1688; Kutschy, Pet al., Synlett 1997, (3), 289-290); to carbamoyl chloride 11 (after 179 or 181 is reductively aminated with an $R^2$ group) (Hintze, F.; Hoppe, D.; Synthesis (1992) 12, 1216-1218); to thiocarbamoyl chloride 11 (after 179 or 181 is reductively aminated with an $R^2$ group) (Ried, W.; Hillenbrand, H.; Oertel, G.; Justus Liebigs Ann Chem 1954, 590); or just used as 9, or 10 (after 179 or 181 is reductively aminated with an $R^2$ group), in synthesizing the compounds of this invention by the methods depicted in Scheme 1.

Scheme 28

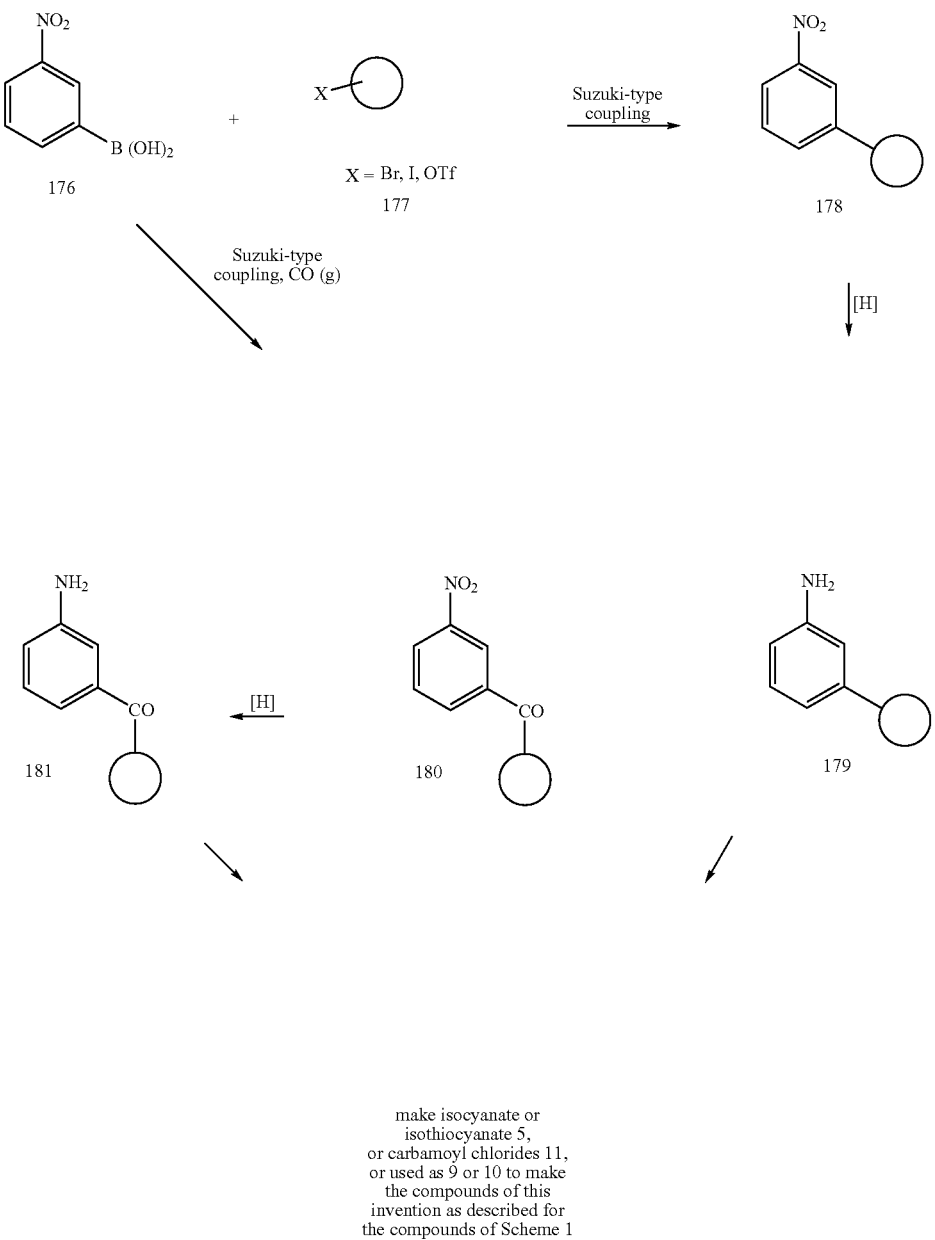

Likewise, protected aminobromobenzenes or triflates or protected aminobromoheterocycles or triflates 182 (Scheme 29) may undergo Suzuki-type couplings with arylboronic acids or heterocyclic boronic acids (183). These same bromides or triflates 182 may also undergo Stille-type coupling (Echavarren, A. M., Stille, J. K. J. Am. Chem. Soc., 1987, 109, 5478-5486) with aryl, vinyl, or heterocyclic stannanes 186. Bromides or triflates 182 may also undergo Negishi-type coupling with other aryl or heterocyclic bromides 187 (Negishi E. Accts. Chem. Res. 1982, 15, 340; M. Sletzinger, et al., Tet. Lett. 1985, 26, 2951). Deprotection of the amino group yields an amine with can be coupled to make a urea and other linkers containing Z as described above and for Scheme 1. Amino protecting groups include phthalimide, 2,4-dimethyl pyrrole (S. P. Breukelman, et al. J. Chem. Soc. Perkin Trans. I, 1984, 2801); N-1,1,4,4-Tetramethyldisilyl-azacyclopentane (STABASE) (S. Djuric, J. Venit, and P. Magnus Tet. Lett 1981, 22, 1787) and others familiar to one skilled in the art.

Scheme 29

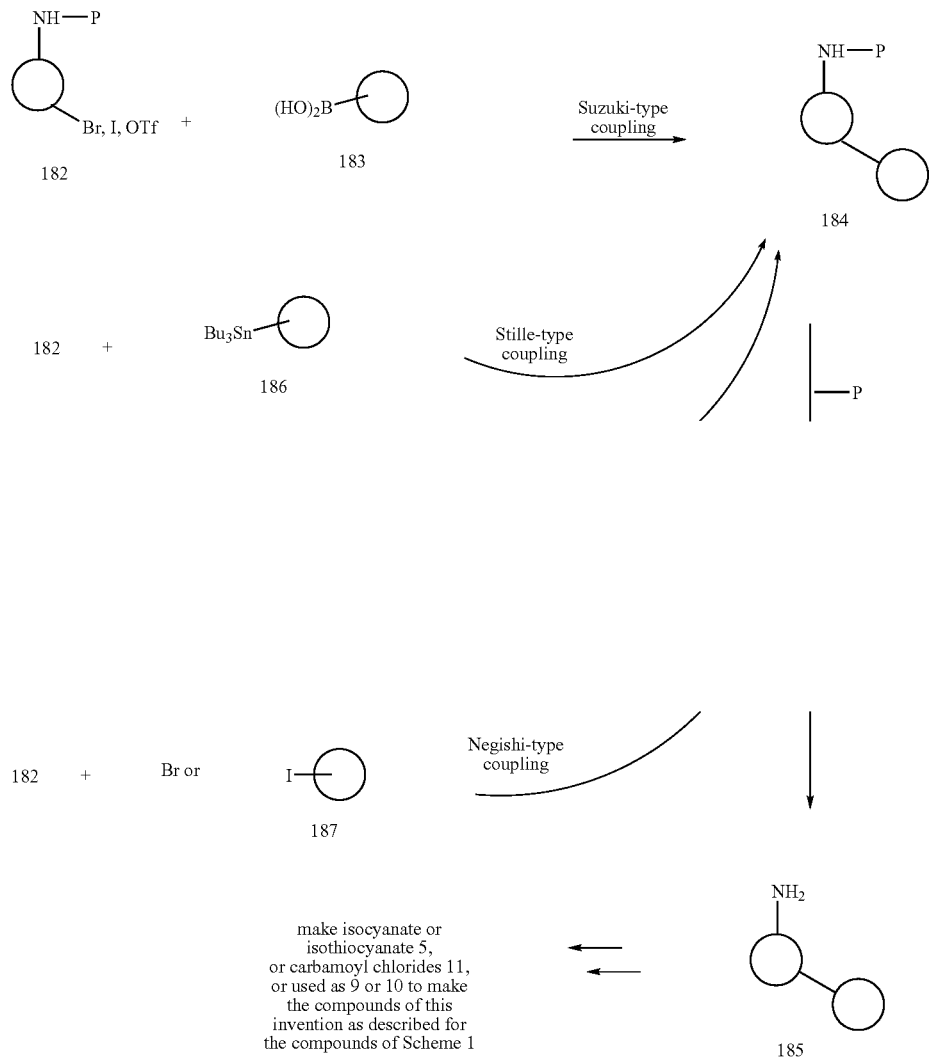

EXAMPLES

The compounds of this invention and their preparation can be understood further by the following working examples. These examples are meant to be illustrative of the present invention, and are not to be taken as limiting thereof.

Example 1

(6S)-6-(4-Fluoro-benzyl)-piperazin-2-one

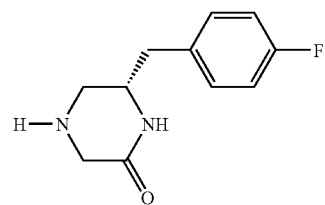

Part 1. [(1S)-2-(4-Fluoro-phenyl)-1-(methoxy-methyl-carbamoyl)-ethyl]-carbamic acid tert-butyl ester

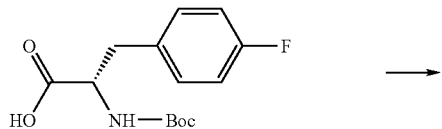

A solution of N-Boc 4-fluorophenylalanine (10.0 g, 35 mmol) in THF (100 ml) was cooled in an ice bath under an inert atmosphere and treated with N-methylmorphline (4.0 g, 40 mmol). To the cold reaction solution was added, dropwise while stirring, isobutylchloroformate (4.8 g, 35 mmol). The mixture was stirred for a few minutes and then treated with a suspension of N,O-dimethyl hydroxylamine HCl (4.0 g, 40 mmol) in DMF. The resulting suspension was stirred for 20 minutes in the ice bath and then diluted with 500 ml of water and extracted into EtOAc. The organic extract was washed successively with 1N NaOH, 1N HCl, water, and brine. The extract was dried over MgSO$_4$, filtered and concentrated in vacuo to give 11.4 grams of the desired Weinreb amide as a thick colorless oil. This was sufficiently clean that it was used without further purification. $^1$H NMR (300 MHz, CDCl$_3$) δ 7.26-7.10 (m, 2H), 6.99-6.93 (m, 2H), 5.18 (bd, J=8 Hz, 1H), 4.91 (m, 1H), 3.68 (s, 3H), 3.16 (s, 3H), 3.06-2.99 (dd, J=7 Hz, J=13 Hz, 1H), 2.88-2.81 (dd, J=7 Hz, J=13 Hz, 1H), 1.39 (s, 9H).

Part 2. [(1S)-1-(4-Fluoro-benzyl)-2-oxo-ethyl]-carbamic acid tert-butyl ester

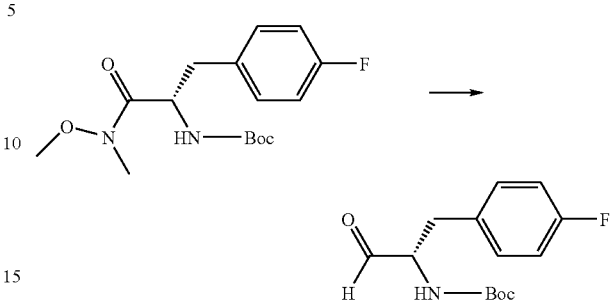

A solution of the crude amide from part 1 (11.4 g, 35 mmol) in ether (200 ml) was cooled to 0° C. in an ice bath and slowly treated portion-wise, with solid LAH (1.66 g, 43 mmol). The resulting suspension was stirred at 0° C. for 30 minutes. The reaction was quenched by drop-wise addition of a saturated aqueous solution of KHSO$_4$ (300 ml). The layers separated and the organic extract washed with 1 N HCl, water, and brine. The extract was dried over MgSO$_4$, filtered and concentrated on a rotary evaporator to give 9.1 grams of the aldehyde as a white solid of sufficient purity that it was used without further purification. $^1$H NMR (300 MHz, CDCl$_3$) δ 9.63 (s, 1H), 7.16-7.11 (m, 2H), 6.99-6.95 (m, 2H), 5.08 (bm, 1H), 4.20 (m, 1H), 3.10 (m, 2H), 1.43 (s, 3H).

Part 3. [(1S)-1-(4-Fluoro-benzyl)-2-((1R)-1-phenyl-ethylamino)-ethyl]-carbamic acid tert-butyl ester

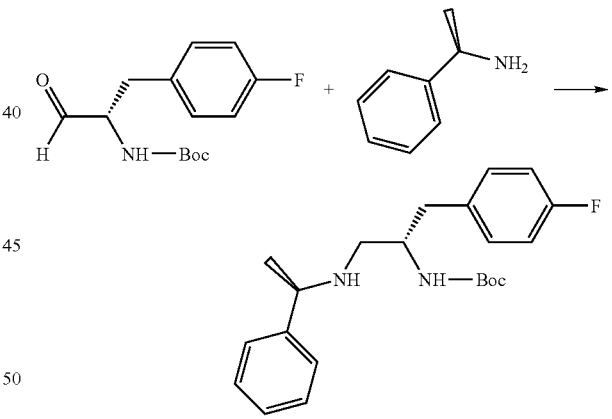

A solution of crude aldehyde from part 2 above (5.0 g, 18 mmol) in CH$_2$Cl$_2$ (100 ml) was treated with R-α-methylbenzyl amine (2.43 g, 20 mmol) and Na(OAc)$_3$BH. The resulting mixture was stirred at room temperature for 3 hours (until reaction was complete by TLC). The mixture was quenched with 1N NaOH (50 ml) and stirred for 30 minutes. The organic layer separated and washed with water, and brine. The extract was dried over MgSO$_4$, filtered and concentrated on a rotary evaporator to give a thick oil. This was chromatographed on silica gel (50% EtOAc/Hexane) to give 6.0 grams of diamine product as an oil. $^1$H NMR (300 MHz, CDCl$_3$) δ 7.33-7.20 (m, 5H), 7.09-7.01 (m, 2h), 6.98-6.88 (m, 2H), 4.63 (bm, 1H), 3.89 (bm, 1H), 3.70 (q, 1H), 2.80-2.74 (bm, 1H), 2.64-2.52 (m, 3H), 2.37-2.31 (dd, J=7 Hz, J=12 Hz, 1H), 1.42 (s, 9H), 1.32 (d, J=7 Hz, 3H). ESI MS: (M+H)$^+$=373.2.

Part 4. [[(2S)-2-tert-Butoxycarbonylamino-3-(4-fluoro-phenyl)-propyl]-((1R)-1-phenyl-ethyl)-amino]-acetic acid methy ester

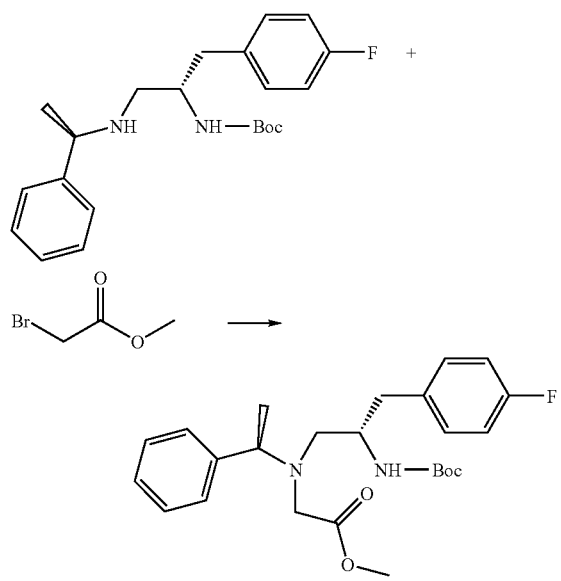

A solution of the diamine from part 3 above (6.0 g, 16 mmol) in DMF (50 ml) was treated with methyl bromoacetate (3.7 g, 24 mmol) and K$_2$CO$_3$ (2.25 g, 16 mmol) and the resulting mixture stirred overnight at room temperature. The reaction mixture was diluted with 300 ml of water and extracted into EtOAc. The organic extracts were washed with water, and brine. The extract was dried over MgSO$_4$, filtered and concentrated on a rotary evaporator to give a thick oil that was used without further purification.

Part 5. 6-(4-Fluoro-benzyl)-4-(1-phenyl-ethyl)-piperazin-2-one

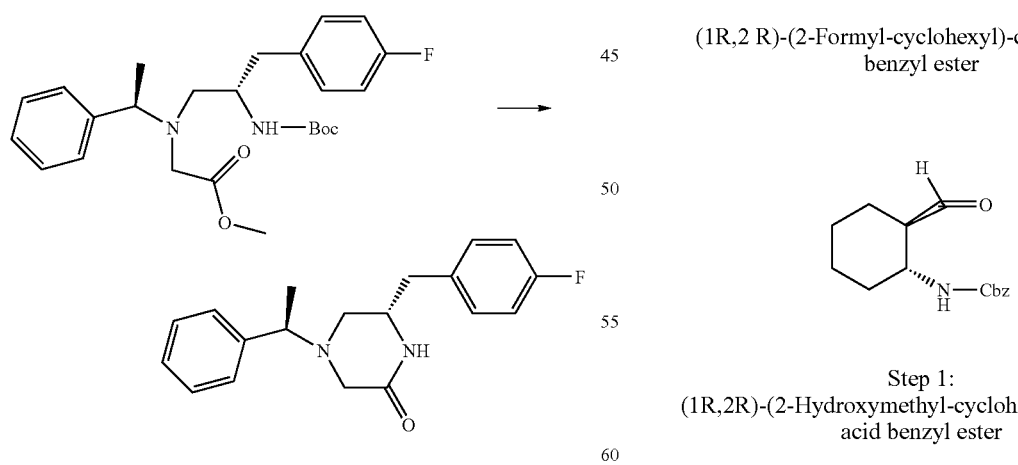

A solution of crude ester from part 4 above (7.1 g, 16 mmol) was dissolved in 60 ml of CH$_2$Cl$_2$ and treated with 75 ml of TFA. The solution was stirred at room temperature for 1 hour. The solvent was removed on a rotary evaporator to give a thick syrup. This syrup was dissolved in methanol (200 ml) and neutralized with 1N NaOH. The solution was stirred for 10 minutes and then diluted with water and extracted into EtOAc. The organic extracts were washed with water, and brine. The extract was dried over MgSO$_4$, filtered and concentrated on a rotary evaporator to give 4.3 g of a white solid. This was chromatographed on silica gel (50-70% EtOAc/Hexane) to give 2.6 grams of the piperazin-2-one. $^1$H NMR (300 MHz, CDCl$_3$) δ 7.36-7.26 (m, 5H), 7.07-6.92 (m, 4H), 5.90 (bs, 1H), 3.58-3.5- (m, 1H), 3.45 (q, J=7 Hz, 1H), 3.28 (d, J=17 Hz, 1H), 3.08 (d, J=17 Hz, 1H), 2.77-2.73 (m, 2H), 2.69-2.64 (dd, J=6 Hz, J=12 Hz, 1H), 2.45-2.39 (dd, J=6 Hz, J=15 Hz, 1H), 1.40 (d, J=7 Hz, 1).

Part 6. (6S)-6-(4-Fluoro-benzyl)-piperazin-2-one

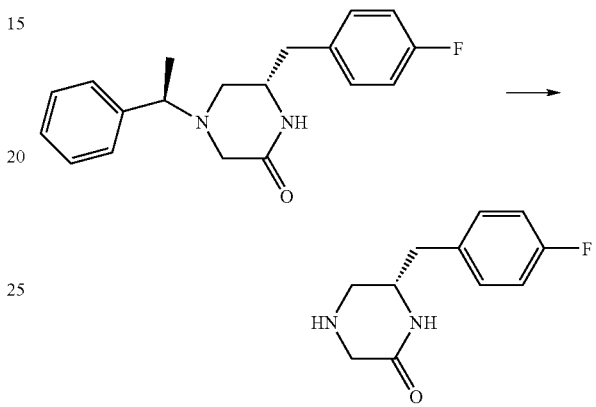

A solution of 4-benzyl-piperazin-2-one from part 5 (2.6 g, 8.3 mmol) in methanol (200 ml) was treated with 1 g of 10% Pd(OH)$_2$/C and hydrogenated at 60 psi of hydrogen for 15 hours. The mixture is filtered and the solvent on a rotary evaporator to give 1.7 grams of the piperazinone as a white solid. [α]$_D^{25}$=+27.70° (CH$_3$OH, c=0.354 g/dL). $^1$H NMR (300 MHz, CDCl$_3$) δ 7.17-7.13 (m, 2H), 7.05-6.99 (m, 2H), 6.05 (bs, 1H), 3.70-3.62 (m, 1H), 3.57-4.31 (dd, J=17 Hz, J=22 Hz, 2H), 3.18-3.12 (dd, J=6 Hz, J=13 Hz, 1H), 2.87-2.81 (dd, J=6 Hz, J=14 Hz, 1H), 2.75-2.64 (overlap dd, 2H), 1.90 (bs, 1H).

Example 2

(1R,2 R)-(2-Formyl-cyclohexyl)-carbamic acid benzyl ester

Step 1: (1R,2R)-(2-Hydroxymethyl-cyclohexyl)-carbamic acid benzyl ester

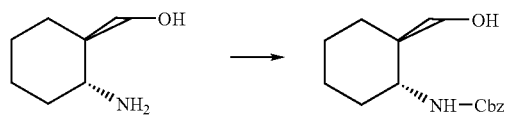

To a solution of (1R,2R)-(2-Amino-cyclohexyl)-methanol [*J. Am. Chem. Soc.* 1996, 118, 5502-5503 and references therein] (1.9 g, 14.7 mmol) in CH$_2$Cl$_2$ (50 mL) is added 50 ml of an aqueous solution of Na$_2$CO$_3$ (2.4 g, 28.9 mmol). While stirring, benzyl chloroformate (2.51 g, 14.7 mmol) is added and the mixture is stirred at room temperature for 1 hour. The organic layer is separated and washed with water and brine. The solution is concentrated on a rotary evaporator and the residue is chromatographed on silica gel (30% ethyl acetate/hexane) to give 3.1 g (12 mmol) of the N—Cbz amino alcohol as a white solid. $^1$H NMR (300 MHz, CDCl$_3$) δ 7.40-7.29 (m, 5H), 5.11 (s, 2H), 4.71 (bd, 1H), 3.76-3.71 (m, 1H), 3.53-3.28 (m, 3H), 2.00-1.95 (m, 1H), 1.90-1.09 (m, 8H). MS AP$^+$ (M+H)$^+$=264.3 (100%)

Step 2: (1R,2R)-(2-Formyl-cyclohexyl)-carbamic acid benzyl ester

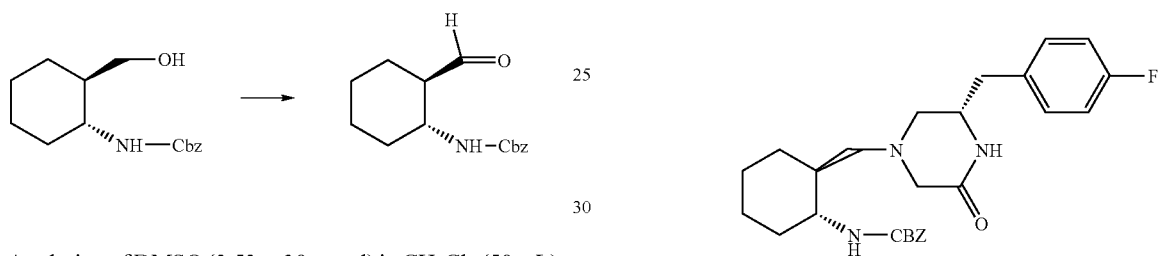

A solution of DMSO (2.52 g, 30 mmol) in CH$_2$Cl$_2$ (50 mL) is cooled to −78° C. To this solution is added drop-wise oxalyl chloride (1.81 g, 14 mmol) and the resulting solution is stirred for an additional 10 min. Then a solution of N—CBZ amino alcohol from part 1 above (2.5 g, 9.5 mmol) in CH$_2$Cl$_2$ (70 ml) is added via an addition funnel and stirred for 10 min. Then Et$_3$N (5.0 g, 50 mmol) is added and the solution is allowed to warm to room temperature. The solution is diluted with water and the organic layer washed with water, 1 N HCl, and brine. The organic layer is dried over Na$_2$SO$_4$, filtered, and concentrated to give 2.5 g (9.5 mmol) of the aldehyde as a white solid. $^1$H NMR (300 MHz, CDCl$_3$) δ 9.59 (d, 3.6 Hz, 1H), 7.38-7.28 (m, 5H), 5.07 (m, 2H), 4.69 (m, 1H), 3.84 (m, 21H), 2.19-2.11 (m, 1H), 2.09-2.01 (m, 1H), 1.86-1.75 (m, 3H), 1.54-1.17 (m, 4H).

Example 3

4-((1R,2R)-2-Amino-cyclohexylmethyl)-(6S)-6-(4-fluoro-benzyl)-piperazin-2-one

Part 1. {(1R,2S)-2-[(3S)-3-(4-Fluoro-benzyl)-5-oxo-piperazin-1-ylmethyl]-cyclohexyl}-carbamic acid benzyl ester

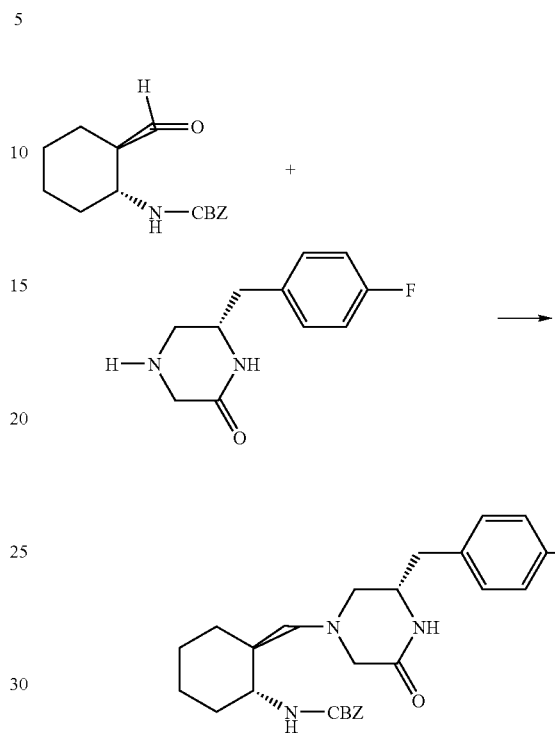

A solution of cyclohexyl aldehyde from EXAMPLE 2 above (2.2 g, 8.4 mmol) and piperazinone from EXAMPLE 1 above (1.7 g, 8.2 mmol) in CH$_2$Cl$_2$ (50 ml) was treated with Na(OAc)$_3$BH (2.68 g, 12.6 mmol). The resulting mixture was stirred at room temperature for 4 hours (until reaction was judged to be complete by TLC). The mixture was quenched with 1N NaOH (50 ml) and stirred for 30 minutes. The organic layer separated and washed with water, and brine. The extract was dried over MgSO$_4$, filtered and concentrated on a rotary evaporator to give a thick oil. This was chromatographed on silica gel (70% EtOAc/Hexane) to give 3.5 grams of product as a white solid. $^1$H NMR (300 MHz, CDCl$_3$) δ 7.36-7.29 (m, 5H), 7.03-6.93 (m, 4H), 5.81 (bs, 1H), 5.67 (bs, 1H), 5.09 (bs, 2H), 3.60 (bm, 1H), 3.25-3.20 (m, 1H), 3.17 (d, J=16 Hz, 1H), 3.01 (d, J=16 Hz, 1H), 2.83-2.51 (m, 5H), 2.40-2.22 (m, 1H), 2.29-2.16 (m, 2H), 1.85-1.81 (m, 1H), 1.74-1.70 (m, 2H), 1.39-0.96 (m, 5H).

Part 2. 4-((1R,2R)-2-Amino-cyclohexylmethyl)-(6S)-6-(4-fluoro-benzyl)-piperazin-2-one

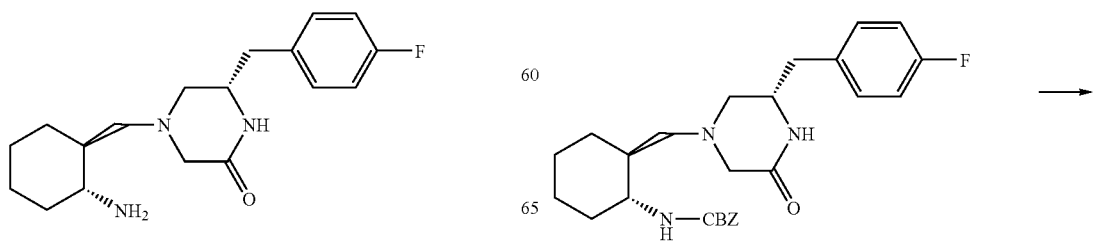

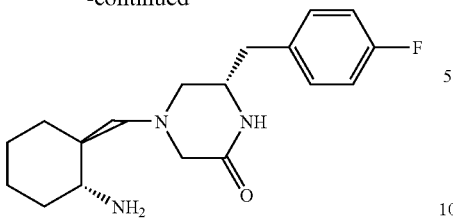

A solution of N—CBZ cyclohexyl piperazinone from part 1 above (3.5 g, 7.7 mmol) in methanol (200 ml) was treated with 2 g of 10% Pd/C and hydrogenated at 60 psi of hydrogen for 15 hours. The mixture is filtered and the solvent removed on a rotary evaporator to give 2.0 grams of the free amino cyclohexyl piperazinone as a white solid. $^1$H NMR (300 MHz, CDCl$_3$) δ 7.19-7.14 (m, 3H), 7.04-6.98 (m, 2H), 6.05 (bs, 1H), 3.84 (bm, 2H), 3.74 (m, 1H), 3.46 (d, J=16 Hz, 1H), 2.84 (d, J=16 Hz, 1H), 2.83-2.71 (m, 2H), 2.57 (m, 2H), 2.33 (m, 2H), 1.93 (m, 1H), 1.71 (m, 3H), 1.47 (m, 1H), 1.23 (m, 3H), 0.88 (m, 2H).

Example 4

(6S)-6-benzyl-piperazin-2-one

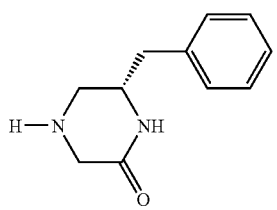

Part 1. (2-Benzyloxycarbonylamino-3-phenyl-propylamino)-acetic acid methyl ester

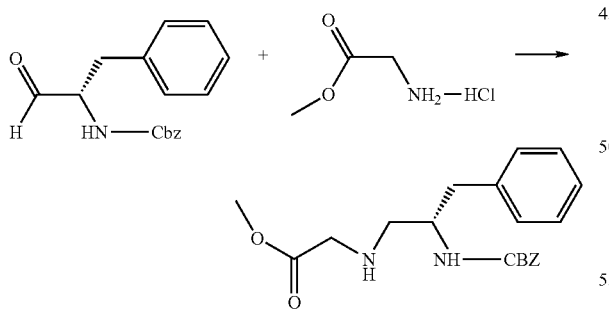

A solution of glycine methyl ester hydrochloride (2.0 g, 15 mmol) in CH$_2$Cl$_2$ was treated with triethylamine (1.5 g, 15 mmol). N—Cbz-Phenylalinal (2.0 g, 7.06 mmol) [synthesized following the same procedure described above for Example 1 (Part 1 and 2)] and was added to the resulting solution. Then Na(OAc)$_3$BH was added and the resulting mixture was stirred at room temperature for 4 hours (until reaction was complete by TLC). The mixture was quenched with 1N NaOH (50 ml) and stirred for 30 minutes. The organic layer separated and washed with water, and brine. The extract was dried over MgSO$_4$, filtered and concentrated on a rotary evaporator to give crude diamine.

Part 2. (6S)-6-benzyl-piperazin-2-one

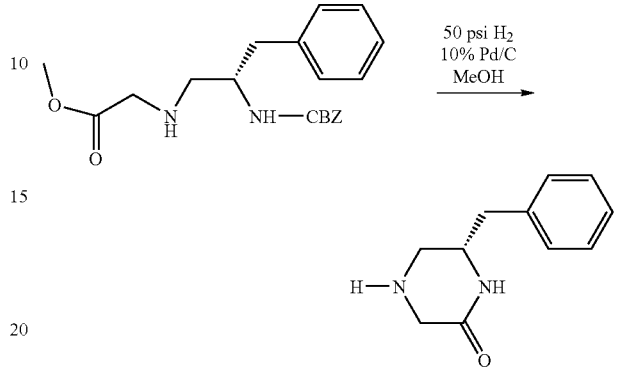

The above crude diamine (1.9 g, 5.3 mmol) was dissolved in methanol and treated with 10% Pd/C and hydrogenated at 50 psi of hydrogen overnight. The mixture is filtered and the solvent removed on a rotary evaporator to give 0.96 grams of the piperazinone directly as a white solid. $[\alpha]_D^{25}$=+14.8° (CH$_3$OH, c=0.834 g/dL). ESI MS: (M+H)$^+$=295.2. $^1$H NMR (300 MHz, CDCl$_3$) δ 7.36-7.20 (m, 4H), 7.18 (d, J=7 Hz, 1H), 5.84 (bs, 1H), 3.73-3.65 (m, 1H), 3.57-4.48 (dd, J=5 Hz, J=22 Hz, 2H), 3.20-3.16 (dd, J=4 Hz, J=13 Hz, 1H), 2.92-2.85 (dd, J=5 Hz, J=13 Hz, 1H), 2.77-2.62 (overlap dd, 2H), 1.78 (bs, 1H). [Note: A sample of same piperazinone synthesized using the method of EXAMPLE 1 above gave an $[\alpha]_D^{25}$=+35.1° (CH$_3$OH, c=0.462 g/dL)].

Example 5

4-((1R,2R)-2-Amino-cyclohexylmethyl)-(6S)-6-benzyl-piperazin-2-one

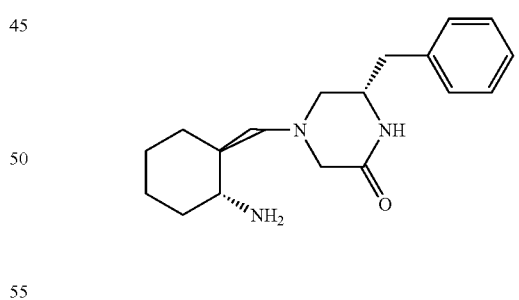

Part 1. {(1R,2S)-2-[(3S)-3-benzyl-5-oxo-piperazin-1-ylmethyl]-cyclohexyl}-carbamic acid benzyl ester

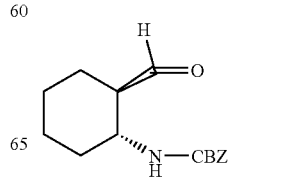

-continued

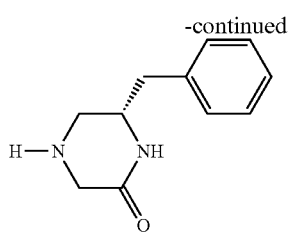

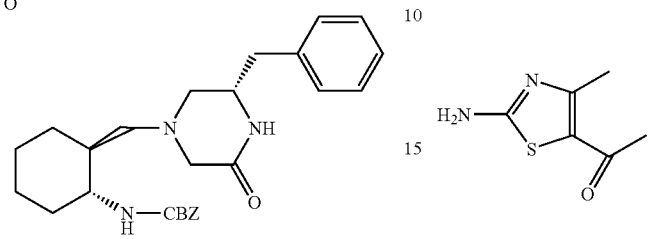

A solution of cyclohexyl aldehyde from EXAMPLE 2 above (1.7 g, 6.5 mmol) and piperazinone from EXAMPLE 4 above (1.0 g, 5.3 mmol) in CH$_2$Cl$_2$ (50 ml) was treated with Na(OAc)$_3$BH (1.5 g, 7.0 mmol). The resulting mixture was stirred at room temperature for 4 hours (until reaction was judged to be complete by TLC). The mixture was quenched with 1N NaOH (50 ml) and stirred for 30 minutes. The organic layer separated and washed with water, and brine. The extract was dried over MgSO$_4$, filtered and concentrated on a rotary evaporator to give white solid. This was chromatographed on silica gel (EtOAc) to give 1.7 grams of product as a white solid. $^1$H NMR (300 MHz, CDCl$_3$) δ 7.36-7.29 (m, 8H), 7.06-7.04 (m, 2H), 5.81 (bs, 1H), 5.67 (bs, 1H), 5.09 (bs, 2H), 3.65 (bm, 1H), 3.25-3.20 (m, 1H), 3.20 (d, J=16 Hz, 1H), 3.01 (d, J=16 Hz, 1H), 2.83-2.51 (m, 5H), 2.40-2.22 (m, 1H), 2.29-2.16 (m, 2H), 1.85-1.81 (m, 1H), 1.74-1.70 (m, 2H), 1.40-0.96 (m, 5H). ESI MS: (M+H)$^+$=436.2.

Part 2. 4-((1R,2R)-2-Amino-cyclohexylmethyl)-(6S)-6-(4-fluoro-benzyl)-piperazin-2-one

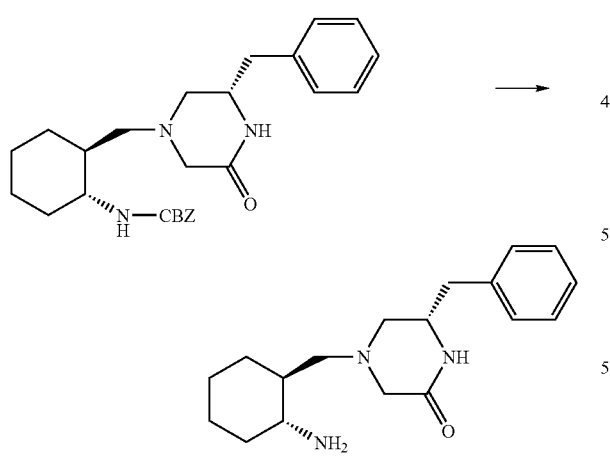

A solution of N-CBZ cyclohexyl piperazinone from part 1 above (1.7 g, 3.9 mmol) in methanol (200 ml) was treated with 2 g of 10% Pd/C and hydrogenated at 60 psi of hydrogen for 15 hours. The mixture is filtered and the solvent removed on a rotary evaporator to give 1.1 grams of the free amino cyclohexyl piperazinone as a white solid. $^1$H NMR (300 MHz, CDCl$_3$) δ 7.36-7.27 (m, 3H), 7.20-7.18 (m, 2H), 6.05 (bs, 1H), 3.74 (m, 1H), 3.30 (d, J=16 Hz, 1H), 2.96 (d, J=16 Hz, 1H), 2.93-2.78 (m, 4H), 2.71-2.58 (m, 4H), 2.50-2.39 (m, 1H), 2.33 (dd, J=7 Hz, J=12 Hz, 1H), 2.20 (dd, J=7 Hz, J=12 Hz, 1H), 2.02 (bs, 2H), 1.91-1.69 (m, 4H), 1.38-0.85 (m, 5H). ESI MS: (M+H)$^+$=302.3; HRMS: (M+H)$^+$=302.2235.

Example 6

(5-Acetyl-4-methyl-thiazol-2-yl)-carbamic acid phenyl ester

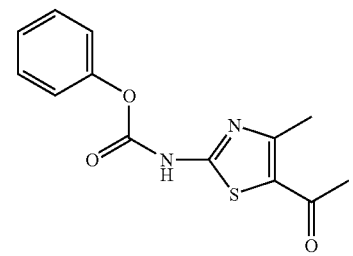

In a round-bottom flask, NaH 60% dispersion in mineral oil (3.07 g, 77 mmol) was washed 2× with hexane and suspended in DMF. Then 2-amino-5-acetyl-4-methyl-thiazole (10.0 g, 64 mmol) was added and stirred while cooling in an ice bath. Stirring continued until the NaH was consumed. Diphenyl carbonate (34 g, 160 mmol) was added while cooling and after the addition was complete the reaction mixture was stirred for an additional ~30 minutes at room temperature. The DMF was removed on a rotary evaporator (high vacuum, 40° C.) to yield a brown residue. This residue was dissolved in 1 L of CHCl$_3$ and washed successively with 2 L of 0.5N HCl, 2×1 L of water, and finally by 1 L of brine. The aqueous portions were back extracted twice with ~300 mL of CHCl$_3$. The combined organic fractions were dried over anhydrous sodium sulfate, filtered and concentrated on a rotary evaporator to give a white solid. This was chromatographed on silica (15%-70% EtOAc/hexane) to give 15 g of the desired carbamate as a white solid. $^1$H NMR (300 MHz, CDCl$_3$) δ 11.42 (bs, 1H), 7.47-7.40 (m, 2H), 7.33-7.27 (m, 1H), 7.22-7.18 (m, 2H), 2.72 (s, 3H), 2.50 (s, 3H). ESI MS: (M+H)$^+$=277.1.

Example 7

N-(3-Acetyl-phenyl)-N'-[3-((3S)-3-benzyl-5-oxo-piperazin-1-yl)-propyl]-urea

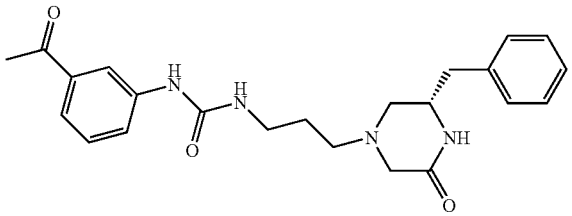

Part 1. 4-(3-Amino-propyl)-(6S)-6-benzyl-piperazin-2-one

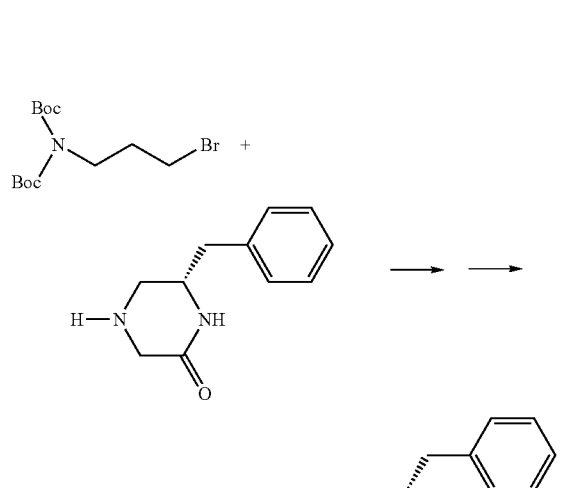

A solution of (6S)-6-benzyl-piperazin-2-one (0.5 g, 2.6 mmol) in DMF was treated with N,N-di-Boc-3-bromo-propylamine (1.0 g, 2.9 mmol) and $K_2CO_3$ (0.5 g, 3.6 mmol) and stirred overnight at room temperature. The reaction mixture was diluted with water and extracted into EtOAc and washed with water, and brine. The extract was dried over $MgSO_4$, filtered and concentrated on a rotary evaporator to give crude alkylated piperazin-2-one as an oil. The crude oil was dissolved in $CH_2Cl_2$ (25 ml) and treated with TFA (25 ml) at room temperature for 1 hour. The solvent was removed under vacuum on a rotary evaporator to give a syrup that was neutralized with 1 N NaOH. The basic solution was extracted into EtOAc and washed with water, and brine. The extract was dried over $MgSO_4$, filtered and concentrated on a rotary evaporator to give 0.2 g of crude amine that was used without further purification.

Part 2. N-(3-Acetyl-phenyl)-N'-[3-((3S)-3-benzyl-5-oxo-piperazin-1-yl)-propyl]-urea

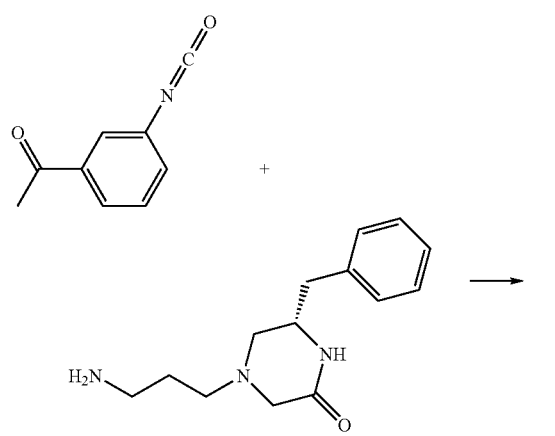

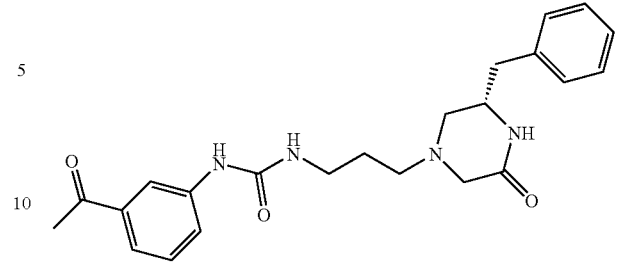

A solution of crude amine from part 1 above (0.2 g, 0.8 mmol) in THF was treated with 3-acetyl-phenylisocyanate (0.16 g, 1.0 mmol) and stirred at room temperature for 30 minutes. The solvents were removed under vacuum on a rotary evaporator and the residue chromatographed on silica gel (first EtOAc; then 10% MeOH/EtOAc) to give 100 mg of desired urea as a white solid. $^1$H NMR (300 MHz, $CDCl_3$/$CD_3OD$) δ 7.95 (bs, 1H), 7.87 (m, 1H), 7.71 (dd, J=1 Hz, J=8 Hz, 1H), 7.55 (d, J=8 Hz, 1H), 7.37-7.23 (m, 4H), 7.14 (d, J=7 Hz, 2H), 6.20 (bs, 1H), 5.87 (bs, 1H), 3.75 (m, 1H), 3.46-3.30 (m, 3H), 3.04 (d, J=16 Hz 1H), 2.94-2.55 (m, 5H), 2.57 (s, 3H), 2.38 (m, 1H), 1.86 (m, 2H), 1.74 (q, J=7 Hz, 2H). ESI MS: (M+H)$^+$=409.2.

Example 8

N-(5-Acetyl-4-methyl-thiazol-2-yl)-N'-{(1R,2S)-2-[(3S)-3-(4-fluoro-benzyl)-5-oxo-piperazin-1-ylmethyl]-cyclohexyl}-urea

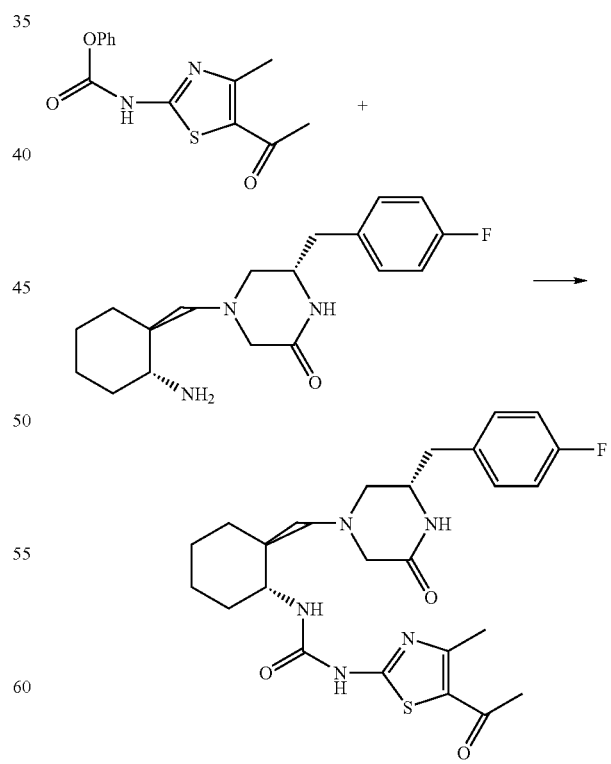

A solution of amine from EXAMPLE 3 (75 mg, 0.23 mmol) and carbamate from EXAMPLE 6 (65 mg, 0.23 mmol) in AcCN (4 ml) was warm to 45° C. for 30 minutes. A solid form and the mixture cooled to room temperature and the solid filtered off to give 50 mg of the desired urea. $^1$H NMR (300 MHz, CDCl$_3$) δ12.21 (bs, 1H), 8.56 (bs, 1H), 6.99-6.90 (m, 4H), 5.49 (bd, J=8 Hz, 1H), 3.52 (m, 1H), 3.40 (m, 1H), 3.24 (d, J=17 Hz, 1H), 2.96 (d, J=17 Hz, 1H), 2.88 (dd, J=5 Hz, J=14 Hz, 1H), 2.73 (dd, J=9 Hz, J=14 Hz, 1H), 2.54 (m, 2H), 2.47 (s, 6H), 2.20-2.06 (m, 3H), 1.90-1.76 (m, 4H), 1.43-1.00 (m, 4H). ESI MS: (M+H)$^+$=502.2; HRMS: (M+H)$^+$=502.2287.

Example 9

N-(5-Acetyl-4-methyl-thiazol-2-yl)-N'-{(1R,2R)-2-[(3S)-3-(4-fluoro-benzyl)-2,5-dioxo-piperazin-1-ylmethyl]-cyclohexyl}-urea

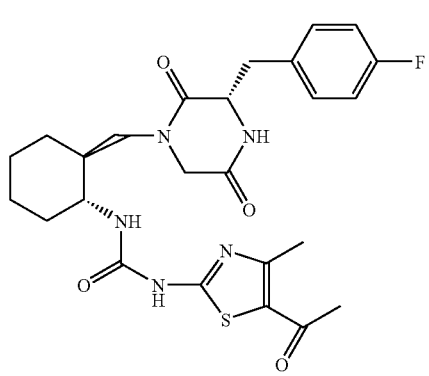

Part 1. [(1S,2R)-(2-Benzyloxycarbonylamino-cyclohexylmethyl)-amino]-acetic acid methyl ester

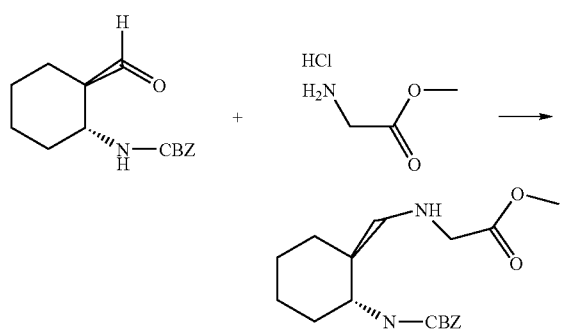

A solution of aldehyde from Example 2 above (5.0 g, 19.1 mmol) and glycine methyl ester HCl (4.80 g, 38.3 mmol) in DMSO (80 ml) was treated with Na(OAc)$_3$BH (8.92 g, 42.08 mmol) and stirred overnight at room temperature. Reaction was quenched by adding water drop-wise and made basic to pH 12 with 1 N NaOH. The aqueous mixture was extracted into EtOAc and washed with water, and brine. The extract was dried over MgSO$_4$, filtered and concentrated on a rotary evaporator to give a residue that was chromatographed on silica (30% EtOAc/hexane) to give 5.37 g of amine product.

Part 2. {((1R,2S)-2-Benzyloxycarbonylamino-cyclohexylmethyl)-[(2S)-2-tert-butoxycarbonylamino-3-(4-fluoro-phenyl)-propionyl]-amino}-acetic acid methyl ester

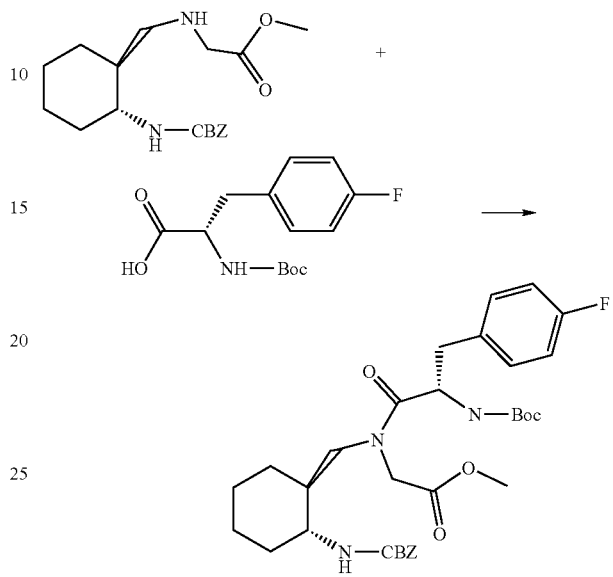

A solution of the amine obtained in part 1 above (1.0 g, 2.99 mmol), N-Boc-4-F-phenylalanine (1.02 g, 3.59 mmol), and HOBT (0.81 g, 5.98 mmol) in CH$_2$Cl$_2$ was treated with DCC (0.74 g, 3.59 mmol) and stirred at room temperature for 48 hours. The reaction mixture was washed with water, brine, and dried over MgSO$_4$. The drying agent was filtered and the solvent removed under vacuum on a rotary evaporator to give a residue that was chromatographed on silica (50% EtOAc/hexane to 100% EtOAc) to give 1.04 g of the amide.

Part 3. {(1R,2R)-2-[(3S)-3-(4-Fluoro-benzyl)-2,5-dioxo-piperazin-1-ylmethyl]-cyclohexyl}-carbamic acid benzyl ester

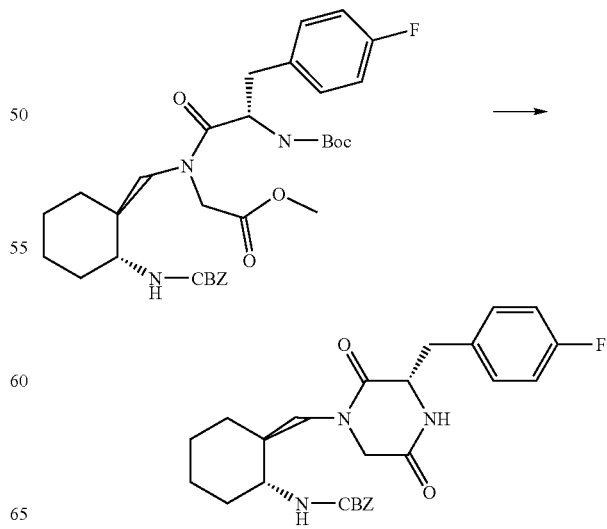

A solution of the amide from part 2 above (0.98 g, 1.63 mmol) in 30 ml of TFA/CH$_2$Cl$_2$ (2:1) was stirred at room temprature for 2 hours. The solvent was removed on a rotary evaporator to give a thick syrup. This syrup was dissolved in methanol (200 ml) and made basic to pH 12 with 1N NaOH. Most of the methanol was removed on a rotary evaporator and then diluted with water and extracted into EtOAc. The organic extracts were washed with water, and brine. The extract was dried over Na$_2$SO$_4$, filtered and concentrated on a rotary evaporator to give a residue that was chromatographed on silica gel (100% EtOAc) to give 0.37 grams of the piperazine-2,5-dione as a white solid.

Part 4. 1-((1R,2R)-2-Amino-cyclohexylmethyl)-(3S)-3-(4-fluoro-benzyl)-piperazine-2,5-dione

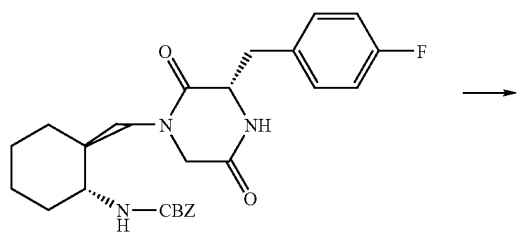

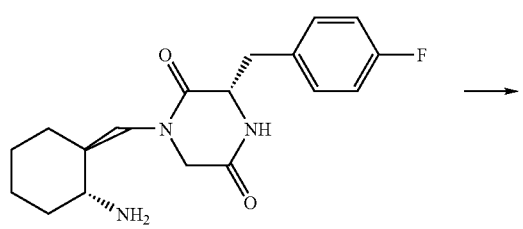

A solution of the piperazine-2,5-dione from part 3 above (0.37 g, 0.23 mmol) in MeOH (20 ml) was treated with 20 mg of 10% Pd/C and hydrogenated at 45 psi of hydrogen for 15 hours. The mixture is filtered and the solvent removed on a rotary evaporator to give 0.28 grams of the free amino which was used without further purification.

Part 5. N-(5-Acetyl-4-methyl-thiazol-2-yl)-N'-{(1R,2R)-2-[(3S)-3-(4-fluoro-benzyl)-2,5-dioxo-piperazin-1-ylmethyl]-cyclohexyl}-urea

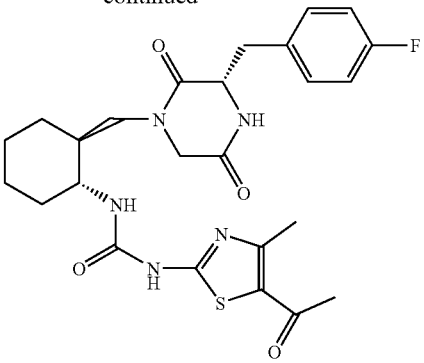

A solution of amine from part 4 (80 mg, 0.23 mmol) in DMF (10 ml) is treated with 5-Acetyl-4-methyl-thiazol-2-yl carbamate from EXAMPLE 6 (63 mg, 0.26 mmol) and stirred overnight at room temperature. The mixture was diluted with water and extracted into EtOAc. The organic extracts were washed with water, and brine. The extract was dried over Na$_2$SO$_4$, filtered and concentrated on a rotary evaporator to give a residue that was chromatographed on silica gel (1:9:90 NH$_3$/MeOH/CHCl$_3$) to give desired urea. $^1$H NMR (300 MHz, CDCl$_3$) δ7.16-7.12 (m, 2H), 6.99 (t, J=11 Hz, 2H), 6.15 (bs, 1H), 4.27 (t, J=5 Hz, 1H), 3.61-3.42 (m, 3H), 3.22 (dd, J=5 Hz, J=6 Hz, 1H), 3.09-2.97 (m, 3H), 2.54 (s, 3H), 2.47 (s, 3H), 2.12 (d, J=10 Hz, 1H), 1.72-1.11 (m, 9H). ESI MS: (M+H)$^+$=516.2.

Example 10

N-(5-Acetyl-4-methyl-thiazol-2-yl)-N'-{(1R,2S)-2-[(5S)-5-(4-fluoro-benzyl)-(2S)-2-hydroxymethyl-3-oxo-piperazin-1-yl-methyl]-cyclohexyl}-urea

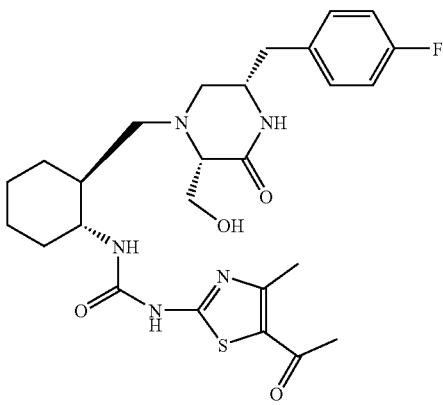

Part 1. (2S)-2-[(2S)-2-tert-Butoxycarbonylamino-3-(4-fluoro-phenyl)-propylamino]-3-hydroxy-propionic acid methyl ester

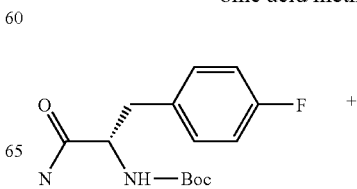

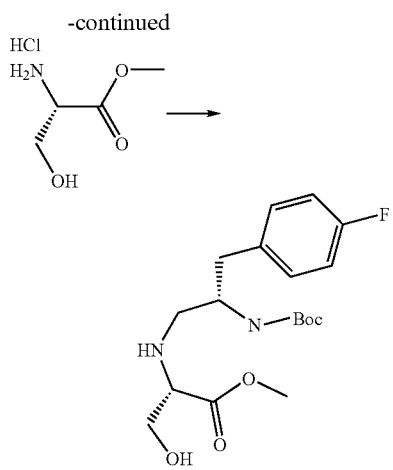

A solution of N-Boc-4-fluorophenylalinal from Example 1 above (2.0 g, 7.48 mmol) and serine methyl ester HCl (1.17 g, 7.48 mmol) in DMSO (50 ml) was treated with Na(OAc)₃BH (2.37 g, 11.2 mmol) and stirred overnight at room temperature. Reaction was quenched by adding water drop-wise and made basic to pH 12 with 1 N NaOH. The aqueous mixture was extracted into EtOAc and washed with water, and brine. The extract was dried over Na₂SO₄, filtered and concentrated on a rotary evaporator to give 2.5 g of crude amine product as a white solid.

Part 2. (2S)-2-{((1S,2R)-2-Benzyloxycarbony-lamino-cyclohexylmethyl)-[(2S)-2-tert-butoxycarbo-nylamino-3-(4-fluoro-phenyl)-propyl]-amino}-3-hydroxy-propionic acid methyl ester

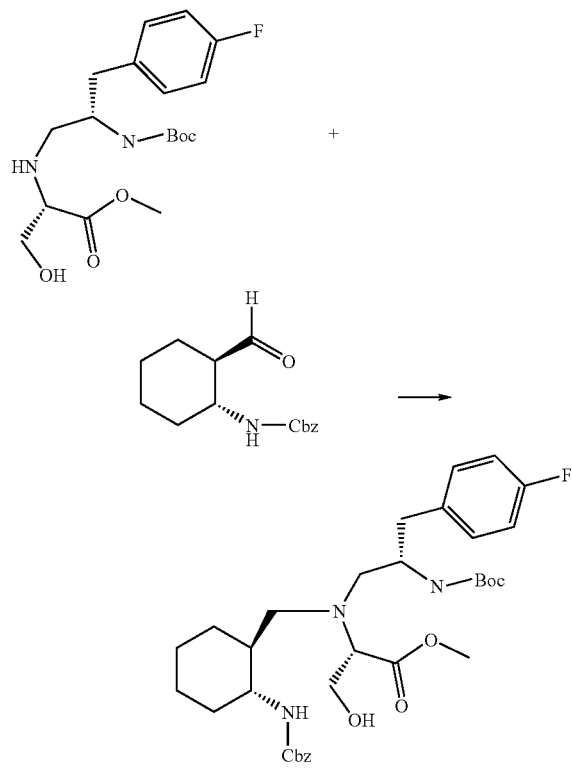

A solution of cyclohexyl aldehyde from EXAMPLE 2 above (1.35 g, 5.18 mmol) and amine from part 1 above (1.92 g, 5.18 mmol) in CH₂Cl₂ (50 ml) was treated with Na(OAc)₃BH (1.65 g, 7.77 mmol). The resulting mixture was stirred at room temperature overnight. The mixture was quenched with 1 N NaOH (50 ml) and stirred for 30 minutes. The organic layer separated and washed with water, and brine. The extract was dried over Na₂SO₄, filtered and concentrated on a rotary evaporator to give a residue. This was chromatographed on silica gel (30% EtOAc/Hexane) to give 1.69 grams of amino alcohol product.

Part 3. {(1R,2S)-2-[(5S)-5-(4-Fluoro-benzyl)-(2S)-2-hydroxymethyl-3-oxo-piperazin-1-ylmethyl]-cyclo-hexyl}-carbamic acid benzyl ester

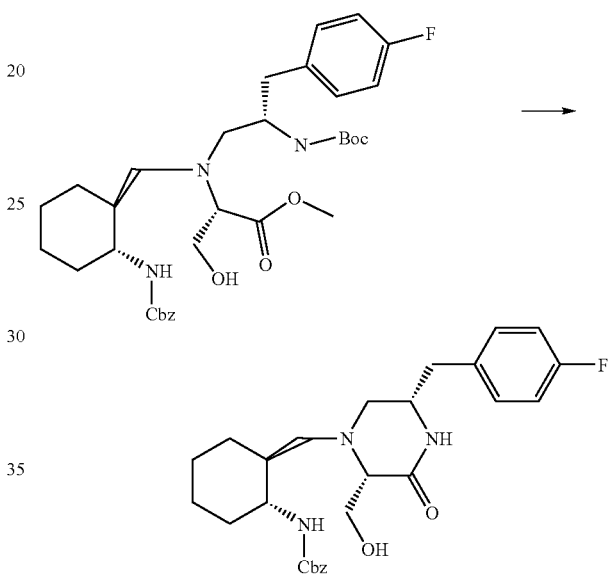

A solution of the amino alcohol from part 2 above (1.69 g, 2.74 mmol) in 30 ml of TFA/CH₂Cl₂ (2:1) was stirred at room temperature for 1 hours. The solvent was removed on a rotary evaporator to give a thick syrup. This syrup was dissolved in methanol (200 ml) and made basic to pH 12 with 1N NaOH. Most of the methanol was removed on a rotary evaporator and then diluted with water and extracted into EtOAc. The organic extracts were washed with water, and brine. The extract was dried over Na₂SO₄, filtered and concentrated on a rotary evaporator to give 1.3 g of the piperazin-2-one as a white solid.

Part 4. 4-((1S,2R)-2-Amino-cyclohexylmethyl)-(6S)-6-(4-fluoro-benzyl)-(3S)-3-hydroxymethyl-piper-azin-2-one

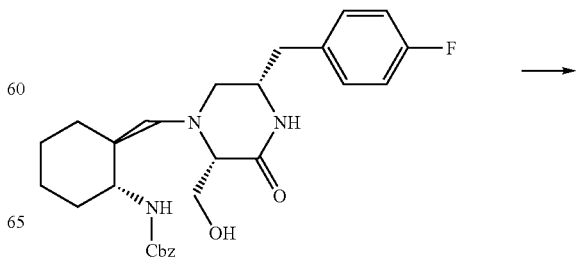

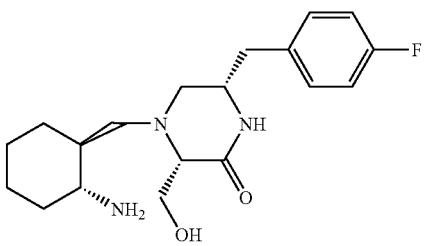

A solution of the piperazin-2-one from part 3 above (1.33 g, 2.75 mmol) in MeOH (50 ml) was treated with 1 g of 10% Pd/C and hydrogenated at 45 psi of hydrogen for 15 hours. The mixture is filtered and the solvent removed on a rotary evaporator to give 0.9 grams of the free amino which was used without further purification.

Part 5. N-(5-Acetyl-4-methyl-thiazol-2-yl)-N'-{(1R, 2S)-2-[(5S)-5-(4-fluoro-benzyl)-(2S)-2-hydroxymethyl-3-oxo-piperazin-1-yl-methyl]-cyclohexyl}-urea

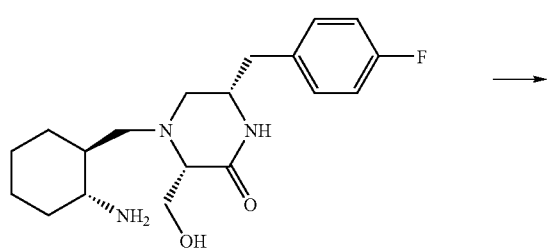

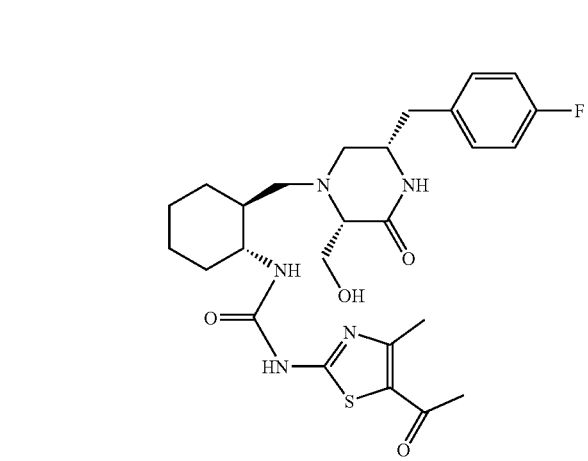

A solution of amine from part 4 above (130 mg, 0.36 mmol) and carbamate from EXAMPLE 6 (100 mg, 0.36 mmol) in AcCN (5 ml) was stirred overnight at room temperature. The solvents were removed under vacuum on a rotary evaporator and the residue chromatographed on silica gel (5% MeOH/EtOAc) to give the desired urea as a white solid. $^1$H NMR (300 MHz, DMSO) δ10.68 (br s, 1H), 7.84 (s, 1H), 7.23-7.18 (m, 2H), 7.08 (t, J=9 Hz, 2H), 6.70 (br s, 1H), 4.57 (br s, 1H), 3.61 (br s, 2H), 3.31 (s, 2H), 2.88-2.73 (m, 4H), 2.51 (s, 3H), 2.43 (s, 3H), 2.37 (m, 1H), 2.36 (m, 1H), 2.15 (m, 1H), 1.89-1.15 (m, 9H). ESI MS: $(M+H)^+=532.3$.

Example 27

N-[(1R,2S)-2-[(2S)-2-Benzyl-6-oxo-morpholin-4-ylmethyl]-cyclohexyl]-N'-phenyl-urea

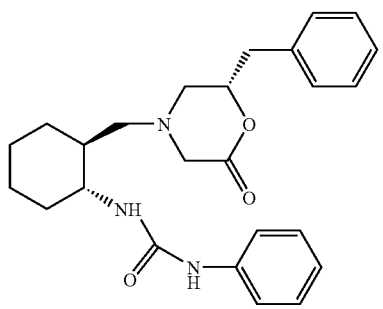

Part 1. 3-Phenyl-(2S)-2-(tetrahydro-pyran-2-yloxy)-propionic acid methyl ester

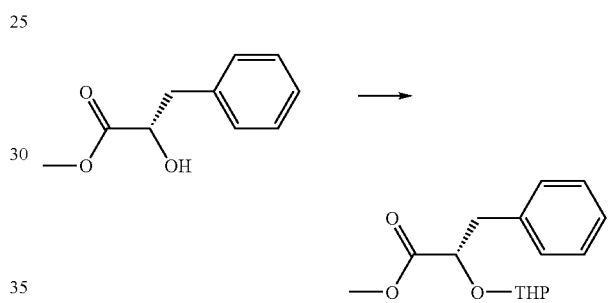

A solution of L-phenyl lactic acid methyl ester (20.0 g, 111 mmol) in $CH_2Cl_2$ (300 mL) was treated with dihydropyran (9.32 g, 111 mmol) and p-toluenesulphonic acid (56 mg) and stirred at room temperature for 20 minutes. The reaction is quenched with 1 N NaOH and then washed with water, brine and dried over $Na_2SO_4$. The solution is filtered and the solvent removed under vacuum to give 28 grams of the THP protected alcohol as an oil. This was used without further purification.

Part 2. 3-Phenyl-(2S)-2-(tetrahydro-pyran-2-yloxy)-propan-1-ol

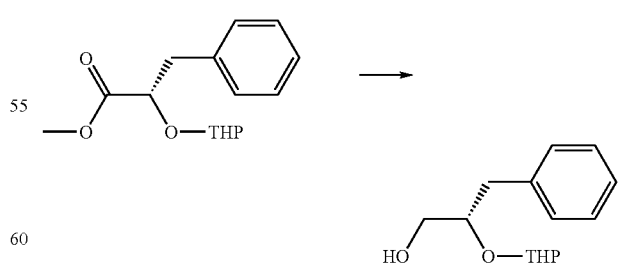

A solution of crude THP protected alcohol ester from Part 1 (28 g, 106 mmol) in ether (300 ml) was cooled in an ice bath and treated with solid LAH (5.0 g, 130 mmol) a small portion at a time [Caution: foaming]. The solution is stirred for 2 hours while cooling in the ice bath. The reaction is quenched by drop-wise addition of 5 ml of water followed by 20 ml of 1 N NaOH [Caution: foaming]. The resulting suspension is stirred for 30 minutes and then filtered and the solids washed with ether. The ether filtrates were dried over Na₂SO₄, the drying agent filtered off, and the solvent removed under vacuum to give 22 g of diol as an oil.

Part 3. 3-Phenyl-(2S)-2-(tetrahydro-pyran-2-yloxy)-propionaldehyde

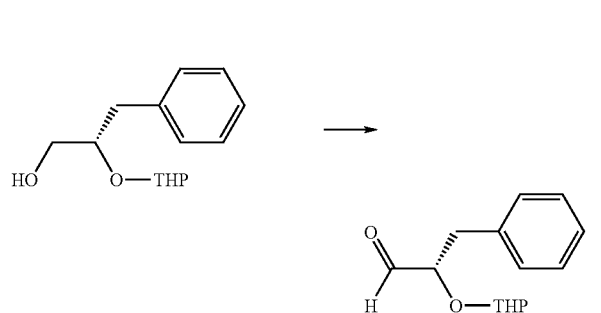

A solution of DMSO (6.3 g, 75 mmol) in methylene chloride was cooled to −78° C. in a dry ice/acetone bath and treated drop-wise with oxalyl chloride (7.0 g, 55 mmol). After the addition was complete, the resulting mixture was stirred for 15 minutes at −78° C. A solution of the alcohol from part 2 (6.6 g, 28 mmol) in CH₂Cl₂ (100 ml) was then added slowly to the reaction mixture via an addition funnel and stirred for another 15 minutes. Then 20 ml of Et₃N was added drop-wise and the resulting mixture was stirred for 10 minutes before removing the dry ice/acetone bath and allowing the mixture to warm to room temperature. The solution is diluted with water and the organic layer washed with water, 1 N HCl, and brine. The organic layer is dried over Na₂SO₄, filtered, and concentrated to give 6.6 g (9.5 mmol) of the crude aldehyde as an oil.

Part 4. [3-(4-Fluoro-phenyl)-(2S)-2-(tetrahydro-pyran-2-yloxy)-propyl]-((1R)-1-phenyl-ethyl)-amine

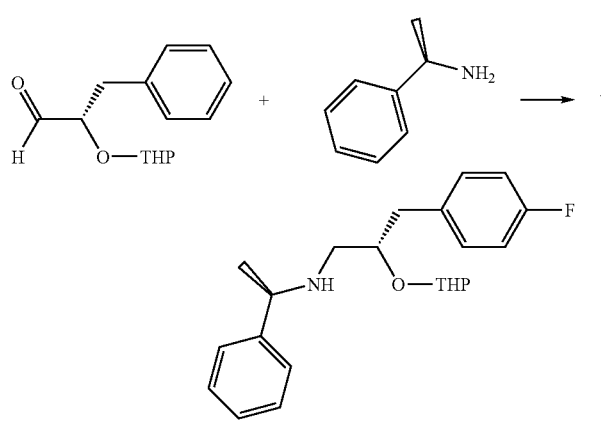

A solution of crude aldehyde from part 3 above (6.6 g, 28 mmol) in CH₂Cl₂ (100 ml) was treated with R-α-methylbenzyl amine (3.4 g, 28 mmol) and Na(OAc)₃BH (8.9 g, 42 mmol). The resulting mixture was stirred at room temperature overnight. The mixture was quenched with 1 N NaOH (50 ml) and stirred for 30 minutes. The organic layer separated and washed with water, and brine. The extract was dried over MgSO₄, filtered and concentrated on a rotary evaporator to give a thick oil. This was chromatographed on silica gel (50% EtOAc/Hexane) to give 3.38 g grams of one amine diastereomer and 2.65 g of a second amine diastereomer. An additional 0.5 g of a mixture of diastereomers was also obtained.

Part 5. {((1R)-1-Phenyl-ethyl)-[3-phenyl-(2S)-2-(tetrahydro-pyran-2-yloxy)-propyl]-amino}-acetic acid methyl ester

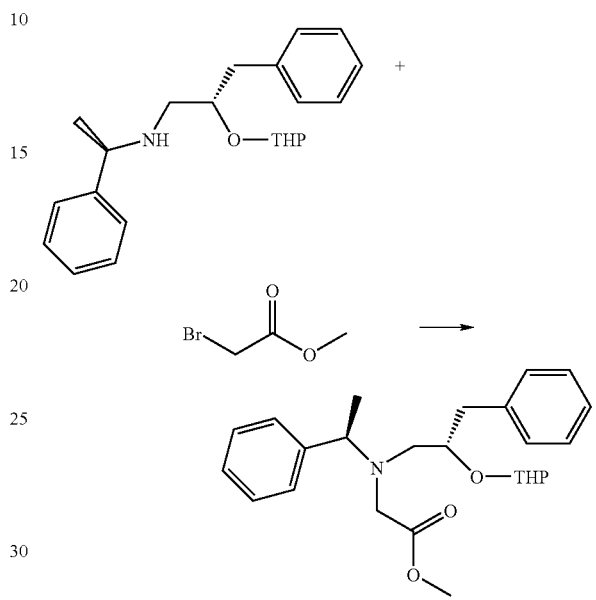

A solution of the amine from part 4 above (3.38 g, 10 mmol) in DMF (20 ml) was treated with methyl bromoacetate (2.29 g, 15 mmol) and K₂CO₃ (2.0 g, 15 mmol). The resulting mixture stirred overnight at room temperature. The reaction mixture was diluted with 300 ml of water and extracted into EtOAc. The organic extracts were washed with water, and brine. The extract was dried over MgSO₄, filtered and concentrated on a rotary evaporator to give 4.1 g of the amine ester as a thick oil and was used without further purification.

Part 6. (6S)-6-Benzyl-4-((1S)-1-phenyl-ethyl)-morpholin-2-one

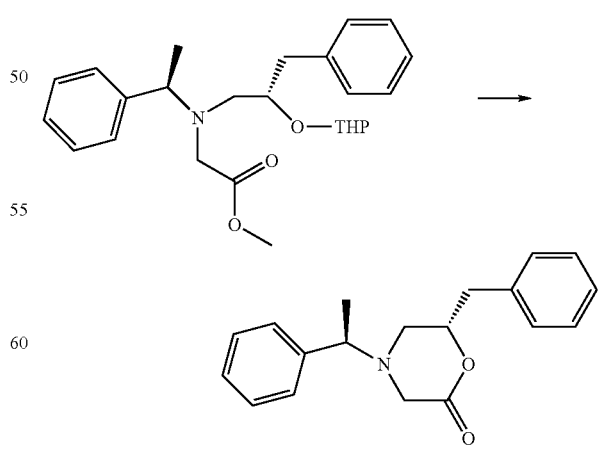

The crude amine ester (4.1 g, 10 mmol) from Part 5 was dissolved in methanol and treated with 1 ml of H₂SO₄ and heated to reflux for 2 hours. Most of the methanol was then removed under vacuum on a rotary evaporator and the resulting residue neutralized with 1 N NaOH and extracted into EtOAc. The organic extract was washed with water and brine. The organic solvent was removed on a rotary evaporator and the resulting residue chromatographed on silica gel (15% EtOAc/hexane) to give 1.8 grams of morpholinone as an oil.

Part 7. (6S)-6-Benzyl-morpholin-2-one

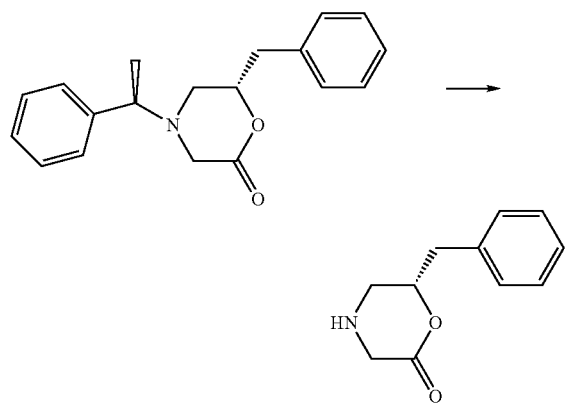

A solution of N-benzyl morpholin-2-one from part 6 (1.8 g, 6.1 mmol) in methanol (100 ml) was treated with 0.5 g of 10% Pd(OH)$_2$/C and hydrogenated at 60 psi of hydrogen for 15 hours. The mixture is filtered and the solvent removed under vacuum on a rotary evaporator to give 1.16 grams of the morpholin-2-one as an oil.

Part 8. [(1R,2S)-2-(2-Benzyl-6-oxo-morpholin-4-ylmethyl)-cyclohexyl]-carbamic acid benzyl ester

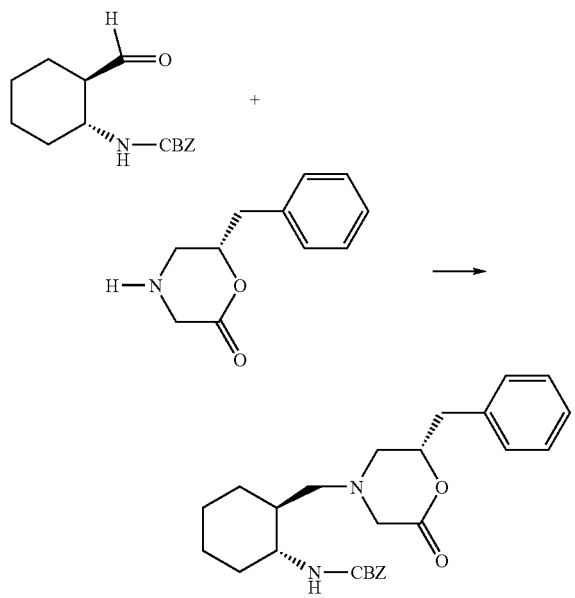

A solution of cyclohexyl aldehyde from EXAMPLE 2 above (1.6 g, 6.1 mmol) and morpholin-2-one from Part 7 above (1.16 g, 6.0 mmol) in CH$_2$Cl$_2$ (50 ml) was treated with Na(OAc)$_3$BH (1.93 g, 9.1 mmol). The resulting mixture was stirred at room temperature for 4 hours (until reaction was judged to be complete by TLC). The mixture was quenched with 1N NaOH (50 ml) and stirred for 30 minutes. The organic layer separated and washed with water, and brine. The extract was dried over MgSO$_4$, filtered and concentrated on a rotary evaporator to give a thick oil. This was chromatographed on silica gel (25% EtOAc/Hexane) to give 1.2 grams of product as a white solid.

Part 9. 4-((1R,2R)-2-Amino-cyclohexylmethyl)-(6S)-6-benzyl-morpholin-2-one

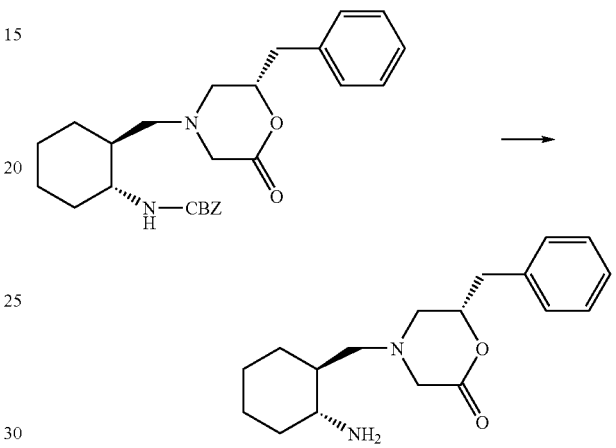

A solution of N—CBZ cyclohexyl morpholin-2-one from part 8 above (1.2 g, 2.7 mmol) in methanol (100 ml) was treated with 0.5 g of 10% Pd/C and hydrogenated at 60 psi of hydrogen for 15 hours. The mixture is filtered and the solvent removed on a rotary evaporator to give 0.83 grams of the free amino cyclohexyl morpholin-2-one as a white solid.

Part 10. N-[(1R,2S)-2-[(2S)-2-Benzyl-6-oxo-morpholin-4-ylmethyl]-cyclohexyl]-N'-phenyl-urea

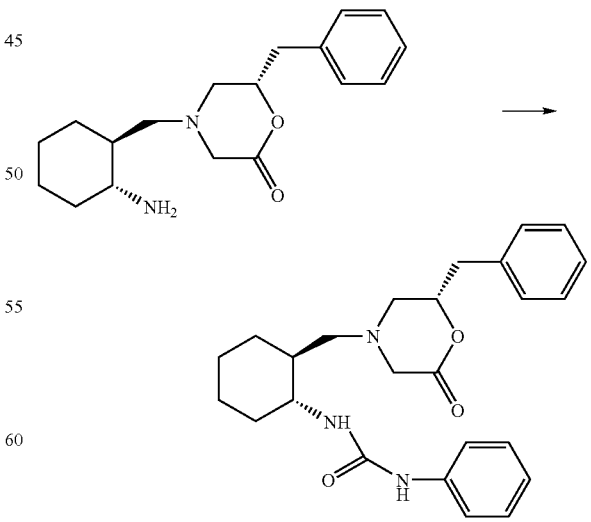

A solution of crude amine from part 9 above (75 mg, 0.25 mmol) in THF was treated with phenylisocyanate (30 mg, 0.25 mmol) and stirred at room temperature for 30 minutes.

The solvents were removed under vacuum on a rotary evaporator and the residue chromatographed on silica gel (25%-50% EtOAc/Hexane) to give 30 mg of desired urea as a white solid. $^1$H NMR (300 MHz, CDCl$_3$) δ 7.33-7.19 (m, 7H), 7.05-7.00 (m, 3H), 6.92 (bs, 1H), 5.69 (d, J=8 Hz, 1H), 4.40 (m, 1H), 3.50 (d, J=18 Hz, 1H), 3.43 (, 1H), 2.93 (d, J=18 Hz, 1H), 2.90(abx m, 2H), 2.62 (m, 2H), 2.31-2.03 (m, 3H), 1.66 (m, 2H), 1.34-0.81 (m, 5H). ESI MS: (M+H)$^+$=422.2.

The following compounds in Table 1 were prepared by above methods or by methods familiar to one skilled the art:

TABLE 1

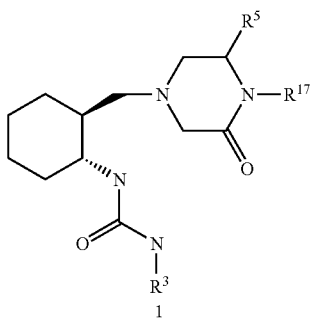
1

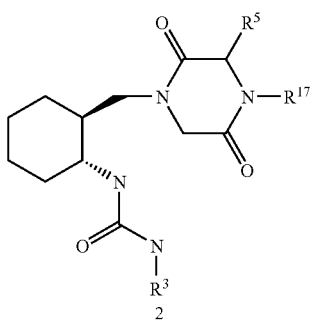
2

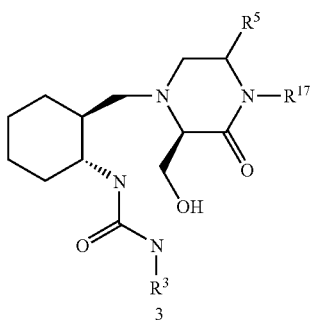
3

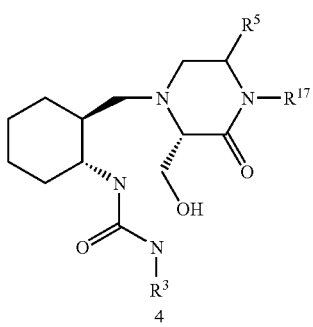
4

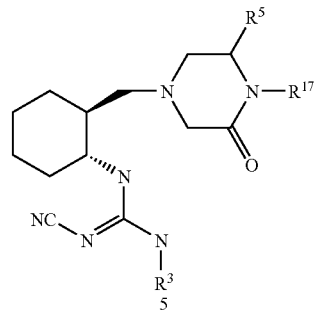
5

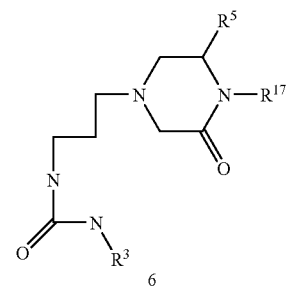
6

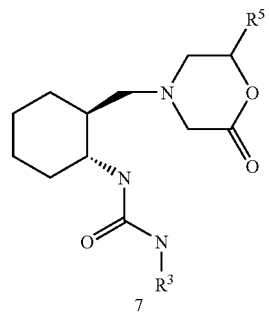
7

| Ex # | Core | R$^5$ | R$^3$ | R$^{17}$ | MS (M + H)+ |
|---|---|---|---|---|---|
| 7 | 6 | (S) CH2Ph | 3-Ac-Ph | H | 409.2 |
| 8 | 1 | (S) CH2Ph(4-F) | 4-Me-5-Ac-Thiazole | H | 502.2 |
| 9 | 2 | (S) CH2Ph(4-F) | 4-Me-5-Ac-Thiazole | H | 516.2 |
| 10 | 3 | (S) CH2Ph(4-F) | 4-Me-5-Ac-Thiazole | H | 532.3 |
| 11 | 4 | (S) CH2Ph(4-F) | 4-Me-5-Ac-Thiazole | H | 532.3 |
| 12 | 1 | (S) CH2Ph(4-F) | 4-Me-5-Ac-Thiazole | Me | 611.3 |
| 13 | 1 | (S) CH2Ph(3-F) | 4-Me-5-Ac-Thiazole | H | 502.2 |
| 14 | 1 | (S) CH2Ph(2-F) | 4-Me-5-Ac-Thiazole | H | 502.2 |
| 15 | 2 | (S) CH2Ph | 4-Me-5-Ac-Thiazole | H | 498.2 |
| 16 | 1 | (S) CH2Ph | 4-Me-5-Ac-Thiazole | H | 484.3 |
| 17 | 1 | (R) CH2Ph(4-F) | 4-Me-5-Ac-Thiazole | H | 502.2 |
| 18 | 1 | (S) CH2Ph(4-Cl) | 4-Me-5-Ac-Thiazole | H | 518.2 |
| 19 | 1 | (R) CH2Ph(4-Cl) | 4-Me-5-Ac-Thiazole | H | 518.2 |
| 20 | 1 | (S) CH2CH2Ph | 4-Me-5-Ac-Thiazole | H | 498.3 |
| 21 | 1 | H | 4-Me-5-Ac-Thiazole | 4-F-Bn | 502.5 |
| 23 | 1 | (S) CH2Ph | Ph | H | 421.1 |
| 24 | 1 | (R) CH2Ph | Ph | H | 421.1 |
| 25 | 5 | (S) CH2Ph | Ph | H | 445.3 |
| 26 | 1 | H | Ph | 4-F-Bn | 439.5 |
| 27 | 7 | (S) CH2Ph | Ph | — | 422.2 |
| 28 | 1 | (S) CH2Ph | 3-CN-Ph | H | 446.3 |
| 29 | 5 | (S) CH2Ph | 3-CN-Ph | H | 470.1 |
| 30 | 1 | (S) CH2Ph(4-F) | 3-Ac-4-F-Ph | H | 499.3 |
| 31 | 5 | (S) CH2Ph | 3-Ac-Ph | H | 487.3 |
| 32 | 1 | (S) CH2Ph | 3-Ac-Ph | H | 463.3 |
| 33 | 1 | (S) CH2Ph(4-F) | 3-Ac-Ph | H | 481.2 |
| 34 | 1 | (S) CH2Ph(3-F) | 3-Ac-Ph | H | 481.3 |
| 35 | 1 | (S) CH2Ph(2-F) | 3-Ac-Ph | H | 481.2 |

TABLE 1-continued

| | | | | | |
|---|---|---|---|---|---|
| 36 | 3 | (S) CH2Ph(4-F) | 3-Ac-Ph | H | 511.3 |
| 37 | 4 | (S) CH2Ph(4-F) | 3-Ac-Ph | H | 511.3 |
| 38 | 1 | (S) CH2Ph(4-F) | 3-Ac-Ph | Me | 495.3 |
| 39 | 1 | (S) CH2Ph(4-F) | 3-Ac-Ph | Bn | 571.3 |
| 40 | 2 | (S) CH2Ph(4-F) | 3-Ac-Ph | H | 477.1 |
| 41 | 1 | (R) CH2Ph(4-F) | 3-Ac-Ph | H | 481.3 |
| 42 | 1 | (S) CH2Ph(4-Cl) | 3-Ac-Ph | H | 497.4 |
| 43 | 1 | (S) CH2Ph(3-CN) | 3-Ac-Ph | H | 488.4 |
| 44 | 1 | (R) CH2Ph(3-CN) | 3-Ac-Ph | H | 488.4 |
| 45 | 1 | (S) CH2CH2Ph | 3-Ac-Ph | H | 477.3 |
| 46 | 1 | H | 3-Ac-Ph | 4-F-Bn | 481.6 |
| 47 | 7 | (S) CH2Ph | 3-Ac-Ph | — | 464.6 |
| 49 | 4 | (S) CH2Ph(4-F) | 3-(1-Hydroxy-ethyl)-Ph | H | 513.5 |
| 51 | 2 | (S) CH2Ph(4-F) | 5-indazole | H | 493.2 |
| 52 | 2 | (S) CH2Ph | 5-indazole | H | 475.1 |
| 53 | 1 | (S) CH2Ph | 5-indazole | H | 461.3 |
| 54 | 1 | (S) CH2Ph(4-F) | 5-indazole | H | 479.2 |
| 55 | 1 | (S) CH2Ph(4-F) | 3,5-di-Ac-Ph | H | 523.3 |
| 56 | 1 | (S) CH2Ph(3-F) | 3,5-di-Ac-Ph | H | 523.4 |
| 57 | 1 | (S) CH2Ph(2-F) | 3,5-di-Ac-Ph | H | 523.2 |
| 58 | 1 | (S) CH2Ph(4-F) | 3,5-di-Ac-Ph | Me | 537.5 |
| 59 | 1 | (R) CH2Ph(4-F) | 3,5-di-Ac-Ph | H | 523.3 |
| 60 | 1 | (S) CH2CH2Ph | 3,5-di-Ac-Ph | H | 519.3 |
| 63 | 7 | (S) CH2Ph | 3,5-di-Ac-Ph | — | 506.3 |
| 64 | 1 | (S) CH2Ph(4-F) | 3,5-di-Ac-Ph | Bn | 613.3 |
| 65 | 1 | (S) CH2Ph(4-F) | 3-(Me-Tetrazole)-Ph | H | 521.3 |
| 66 | 1 | (S) CH2Ph(2-F) | 3-(Me-Tetrazole)-Ph | H | 521.3 |
| 67 | 3 | (S) CH2Ph(4-F) | 3-(Me-Tetrazole)-Ph | H | 551.3 |
| 68 | 4 | (S) CH2Ph(4-F) | 3-(Me-Tetrazole)-Ph | H | 551.3 |
| 69 | 1 | (S) CH2Ph(4-F) | 3-(Me-Tetrazole)-Ph | Me | 535.3 |
| 70 | 1 | (S) CH2Ph(4-F) | 3-(Me-Tetrazole)-Ph | Bn | 611.3 |
| 71 | 1 | (R) CH2Ph(4-F) | 3-(Me-Tetrazole)-Ph | H | 521.3 |
| 72 | 1 | (S) CH2Ph(4-Cl) | 3-(Me-Tetrazole)-Ph | H | 537.5 |
| 73 | 1 | (S) CH2Ph(3-CN) | 3-(Me-Tetrazole)-Ph | H | 528.4 |
| 74 | 1 | (R) CH2Ph(3-CN) | 3-(Me-Tetrazole)-Ph | H | 528.4 |
| 75 | 1 | (S) CH2CH2Ph | 3-(Me-Tetrazole)-Ph | H | 517.3 |
| 78 | 1 | H | 3-(Me-Tetrazole)-Ph | 4-F-Bn | 521.1 |
| 79 | 7 | (S) CH2Ph | 3-(Me-Tetrazole)-Ph | — | 504.2 |
| 81 | 1 | (S) CH2Ph(4-F) | 5-indoline | H | 480.3 |
| 82 | 1 | (S) CH2Ph(3-F) | 5-indoline | H | 480.4 |
| 83 | 1 | (S) CH2Ph(4-F) | 4-Me-2-Thiazole | H | 460.2 |
| 84 | 1 | (S) CH2Ph(4-F) | 2-Thiadiazole | H | 447.2 |
| 85 | 1 | (S) CH2Ph(4-F) | 1-Me-3-Pyrazole | H | 443.3 |
| 86 | 1 | (S) CH2Ph(4-F) | 2-Thiazole | H | 446.2 |

The following contains representative examples of the present invention, and may be prepared by procedures described above, or methods familiar to one skilled in the art. Each entry in each of the tables ($R^3$ and $R^5$) is intended to be paired with each core 1-7 shown at the beginning of the tables.

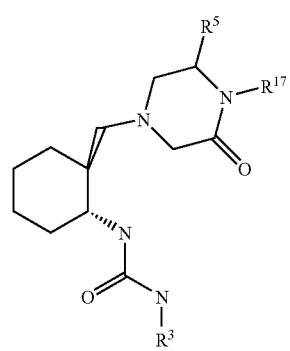

1

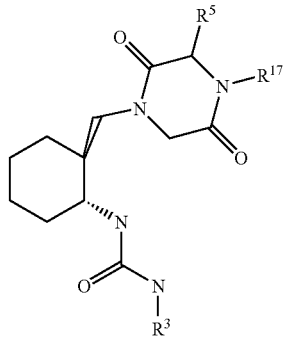

2

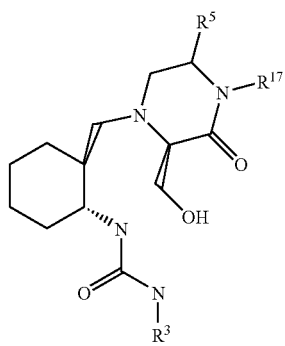

3

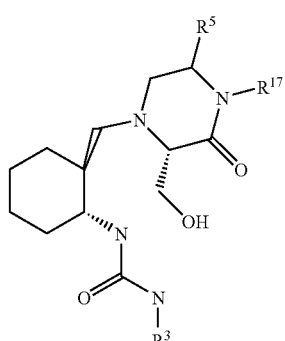

4

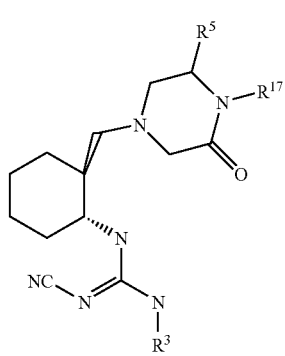

5

-continued

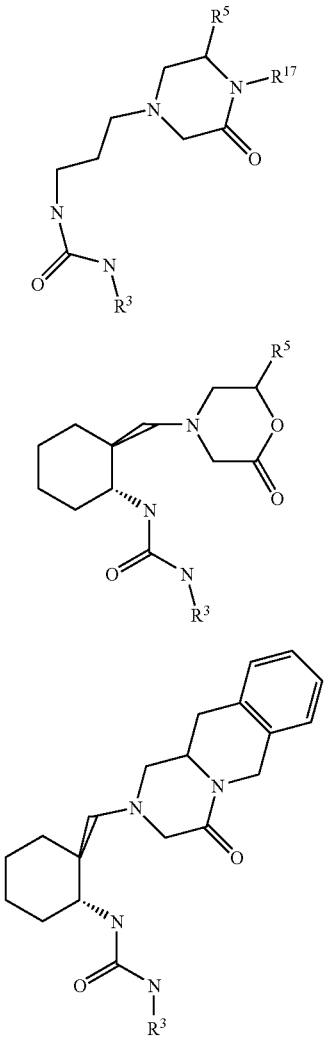

| | | |
|---|---|---|
| 1. | 3-CN—Ph | |
| 2. | 3-COCH3—Ph | |
| 3. | 3-CO2Me—Ph | |
| 4. | 3-CO2Et—Ph | |
| 5. | 3-CO2H—Ph | |
| 6. | 3-CONH2—Ph | |
| 7. | 3-CONHMe—Ph | |
| 8. | 3-F—Ph | |
| 9. | 3-Cl—Ph | |
| 10. | 3-Br—Ph | |
| 11. | 3-NO2—Ph | |
| 12. | 3-NH2—Ph | |
| 13. | 3-NHMe—Ph | |
| 14. | 3-NMe2—Ph | |
| 15. | 3-NHCOCH3—Ph | |
| 16. | 3-SO2NH2—Ph | |
| 17. | 3-SO2NHMe—Ph | |
| 18. | 3-CF3—Ph | |
| 19. | 3-OCH3—Ph | |
| 20. | 3-OPh—Ph | |
| 21. | 3-OCF3—Ph | |
| 22. | 3-SCH3—Ph | |
| 23. | 3-SOCH3—Ph | |
| 24. | 3-SO2CH3—Ph | |
| 25. | 3-OH—Ph | |

-continued

| | | |
|---|---|---|
| 26. | 3-CH2OH—Ph | |
| 27. | 3-CHOHCH3—Ph | |
| 28. | 3-COH(CH3)2—Ph | |
| 29. | 3-CHOHPh—Ph | |
| 30. | 3-CH3—Ph | |
| 31. | 3-C2H5—Ph | |
| 32. | 3-iPr—Ph | |
| 33. | 3-tBu—Ph | |
| 34. | 3-Ph—Ph | |
| 35. | 3-CH2Ph—Ph | |
| 36. | 3-CH2CO2Me—Ph | |
| 37. | 3-(1-piperidinyl)-Ph | |
| 38. | 3-(1-pyrrolidinyl)-Ph | |
| 39. | 3-(2-imidazolyl)-Ph | |
| 40. | 3-(1-imidazolyl)-Ph | |
| 41. | 3-(2-thiazolyl)-Ph | |
| 42. | 3-(3-pyrazolyl)-Ph | |
| 43. | 3-(1-pyrazolyl)-Ph | |
| 44. | 3-(1-tetrazolyl)-Ph | |
| 45. | 3-(5-tetrazolyl)-Ph | |
| 46. | 3-(2-pyridyl)-Ph | |
| 47. | 3-(2-thienyl)-Ph | |
| 48. | 3-(2-furanyl)-Ph | |
| 49. | 4-CN—Ph | |
| 50. | 4-COCH3—Ph | |
| 51. | 4-CO2Me—Ph | |
| 52. | 4-CO2Et—Ph | |
| 53. | 4-CO2H—Ph | |
| 54. | 4-CONH2—Ph | |
| 55. | 4-CONHMe—Ph | |
| 56. | 4-CONHPh—Ph | |
| 57. | 4-NHCONH2—Ph | |
| 58. | 4-F—Ph | |
| 59. | 4-Cl—Ph | |
| 60. | 4-Br—Ph | |
| 61. | 4-NO2—Ph | |
| 62. | 4-NH2—Ph | |
| 63. | 4-NHMe—Ph | |
| 64. | 4-NMe2—Ph | |
| 65. | 4-NHCOCH3—Ph | |
| 66. | 4-SO2NH2—Ph | |
| 67. | 4-SO2NHMe—Ph | |
| 68. | 4-CF3—Ph | |
| 69. | 4-OCH3—Ph | |
| 70. | 4-OPh—Ph | |
| 71. | 4-OCF3—Ph | |
| 72. | 4-SCH3—Ph | |
| 73. | 4-SOCH3—Ph | |
| 74. | 4-SO2CH3—Ph | |
| 75. | 4-OH—Ph | |
| 76. | 4-CH2OH—Ph | |
| 77. | 4-CHOHCH3—Ph | |
| 78. | 4-COH(CH3)2—Ph | |
| 79. | 4-CH3—Ph | |
| 80. | 4-C2H5—Ph | |
| 81. | 4-iPr—Ph | |
| 82. | 4-tBu—Ph | |
| 83. | 4-Ph—Ph | |
| 84. | 4-CH2Ph—Ph | |
| 85. | 4-CH2CO2Me—Ph | |
| 86. | 4-(1-piperidinyl)-Ph | |
| 87. | 4-(1-pyrrolidinyl)-Ph | |
| 88. | 4-(2-imidazolyl)-Ph | |
| 89. | 4-(1-imidazolyl)-Ph | |
| 90. | 4-(2-thiazolyl)-Ph | |
| 91. | 4-(3-pyrazolyl)-Ph | |
| 92. | 4-(1-pyrazolyl)-Ph | |
| 93. | 4-(1-tetrazolyl)-Ph | |
| 94. | 4-(5-tetrazolyl)-Ph | |
| 95. | 4-(2-pyridyl)-Ph | |
| 96. | 4-(2-thienyl)-Ph | |
| 97. | 4-(2-furanyl)-Ph | |
| 98. | 2-CN—Ph | |
| 99. | 2-COCH3—Ph | |
| 100. | 2-CO2Me—Ph | |
| 101. | 2-CO2Et—Ph | |
| 102. | 2-CO2H—Ph | |
| 103. | 2-CONH2—Ph | |
| 104. | 2-CONHMe—Ph | |

-continued

| | |
|---|---|
| 105. | 2-F—Ph |
| 106. | 2-Cl—Ph |
| 107. | 2-Br—Ph |
| 108. | 2-NO2—Ph |
| 109. | 2-NH2—Ph |
| 110. | 2-NHMe—Ph |
| 111. | 2-NMe2—Ph |
| 112. | 2-NHCOCH3—Ph |
| 113. | 2-SO2NH2—Ph |
| 114. | 2-SO2NHMe—Ph |
| 115. | 2-CF3—Ph |
| 116. | 2-OCH3—Ph |
| 117. | 2-OPh—Ph |
| 118. | 2-OCF3—Ph |
| 119. | 2-SCH3—Ph |
| 120. | 2-SOCH3—Ph |
| 121. | 2-SO2CH3—Ph |
| 122. | 2-OH—Ph |
| 123. | 2-CH2OH—Ph |
| 124. | 2-CHOHCH3—Ph |
| 125. | 2-COH(CH3)2-Ph |
| 126. | 2-CHOHPh—Ph |
| 127. | 2-CH3—Ph |
| 128. | 2-C2H5—Ph |
| 129. | 2-iPr—Ph |
| 130. | 2-tBu—Ph |
| 131. | 2-Ph—Ph |
| 132. | 2-CH2Ph—Ph |
| 133. | 2-CH2CO2Me—Ph |
| 134. | 2-(1-piperidinyl)-Ph |
| 135. | 2-(1-pyrrolidinyl)-Ph |
| 136. | 2-(2-imidazolyl)-Ph |
| 137. | 2-(1-imidazolyl)-Ph |
| 138. | 2-(2-thiazolyl)-Ph |
| 139. | 2-(3-pyrazolyl)-Ph |
| 140. | 2-(1-pyrazolyl)-Ph |
| 141. | 2-(1-tetrazolyl)-Ph |
| 142. | 2-(5-tetrazolyl)-Ph |
| 143. | 2-(2-pyridyl)-Ph |
| 144. | 2-(2-thienyl)-Ph |
| 145. | 2-(2-furanyl)-Ph |
| 146. | 2,4-diF—Ph |
| 147. | 2,5-diF—Ph |
| 148. | 2,6-diF—Ph |
| 149. | 3,4-diF—Ph |
| 150. | 3,5-diF—Ph |
| 151. | 2,4-diCl—Ph |
| 152. | 2,5-diCl—Ph |
| 153. | 2,6-diCl—Ph |
| 154. | 3,4-diCl—Ph |
| 155. | 3,5-diCl—Ph |
| 156. | 3,4-diCF3—Ph |
| 157. | 3,5-diCF3—Ph |
| 158. | 5-Cl-2-MeO—Ph |
| 159. | 5-Cl-2-Me—Ph |
| 160. | 2-F-5-Me—Ph |
| 161. | 2-F-5-NO2—Ph |
| 162. | 3,4-OCH2O—Ph |
| 163. | 3,4-OCH2CH2O—Ph |
| 164. | 2-MeO-4-Me—Ph |
| 165. | 2-MeO-5-Me—Ph |
| 166. | 1-naphthyl |
| 167. | 2-naphthyl |
| 168. | 2-thienyl |
| 169. | 3-thienyl |
| 170. | 2-furanyl |
| 171. | 3-furanyl |
| 172. | 2-pyridyl |
| 173. | 3-pyridyl |
| 174. | 4-pyridyl |
| 175. | 2-indolyl |
| 176. | 3-indolyl |
| 177. | 5-indolyl |
| 178. | 6-indolyl |
| 179. | 3-indazolyl |
| 180. | 5-indazolyl |
| 181. | 6-indazolyl |
| 182. | 2-imidazolyl |
| 183. | 3-pyrazolyl |
| 184. | 2-thiazolyl |
| 185. | 5-tetrazolyl |
| 186. | 2-benzimidazolyl |
| 187. | 5-benzimidazolyl |
| 188. | 2-benzothiazolyl |
| 189. | 5-benzothiazolyl |
| 190. | 2-benzoxazolyl |
| 191. | 5-benzoxazolyl |
| 192. | 1-adamantyl |
| 193. | 2-adamantyl |
| 194. | 3-(1-methyltetrazol-5-yl)-Ph |
| 195. | 3-(5-methyltetrazol-1-yl)-Ph |
| 196. | 3-(1-ethyltetrazol-5-yl)-Ph |
| 197. | 3-(1-cyclopropylyltetrazol-5-yl)-Ph |
| 198. | 3-(1-(2-methoxyethyl)tetrazol-5-yl)-Ph |
| 199. | 3-(1-(2-cyanoethyl)tetrazol-5-yl)-Ph |
| 200. | 3-(1-methyltetrazol-5-yl)-5-[(CH3)2N-CO]—Ph |
| 201. | 3-(1-methyltetrazol-5-yl)-5-[(CH3)NH-CO]—Ph |
| 202. | 3-(1-methyltetrazol-5-yl)-5-[H2N-CO]—Ph |
| 203. | 3-(1-methyltetrazol-5-yl)-5-[COCH3]—Ph |
| 204. | 3-(1-methyltetrazol-5-yl)-5-[morpholin-1-yl-CO]-Ph |
| 205. | 3-(1-methyltetrazol-5-yl)-5-F—Ph |
| 206. | 3-(1-methyltetrazol-5-yl)-5-Cl—Ph |
| 207. | 3-(1-methyltetrazol-5-yl)-5-Br—Ph |
| 208. | 3-(1-methyltetrazol-5-yl)-4-F—Ph |
| 209. | 3-(1-methyltetrazol-5-yl)-4-Cl—Ph |
| 210. | 3-(1-methyltetrazol-5-yl)-4-Br—Ph |
| 211. | 3-(1-methyltetrazol-5-yl)-5-CF3—Ph |
| 212. | 3-(1-methyltetrazol-5-yl)-4-CF3—Ph |
| 213. | 3-(1-methyltetrazol-5-yl)-2-CH3O—Ph |
| 214. | 3-(1-methyltetrazol-5-yl)-4-CH3O—Ph |
| 215. | 3-(1-methyltetrazol-5-yl)-5-CH3O—Ph |
| 216. | 3-(1-methyltetrazol-5-yl)-6-CH3O—Ph |
| 217. | 3-(1-methyltetrazol-5-yl)-5-CH3—Ph |
| 218. | 3-(1-methyltetrazol-5-yl)-5-CH3CH2—Ph |
| 219. | 4-(1-methyltetrazol-5-yl)-5-[morpholin-1-yl-CO]-Ph |
| 220. | 4-(1-methyltetrazol-5-yl)-5-F—Ph |
| 221. | 4-(1-methyltetrazol-5-yl)-5-Cl—Ph |
| 222. | 4-(1-methyltetrazol-5-yl)-5-Br—Ph |
| 223. | 4-(1-methyltetrazol-5-yl)-3-CF3—Ph |
| 224. | 4-(1-methyltetrazol-5-yl)-2-CH3O—Ph |
| 225. | 4-(1-methyltetrazol-5-yl)-5-CH3O—Ph |
| 226. | 3,5-bis(morpholin-1-yl)-Ph |
| 227. | 3,5-bis(1,2,4-triazol-1-yl)-Ph |
| 228. | 3,5-bis(pyrazol-1-yl)-Ph |
| 229. | 3,5-bis(oxazol-2-yl)-Ph |
| 230. | 3,5-bis(isoxazol-3-yl)-Ph |
| 231. | 3,5-bis(isoxazol-5-yl)-Ph |
| 232. | 3,5-bis(1,2,3-triazol-1-yl)-Ph |
| 233. | 3,5-bis(COCH3)-Ph |
| 234. | 3,5-bis(CH2OH)-Ph |
| 235. | 3-(thiazol-4-yl)-Ph |
| 236. | 3-(thiazol-5-yl)-Ph |
| 237. | 3-(pyrazol-4-yl)-Ph |
| 238. | 3-(1-methyl-3-pyrazolyl)-Ph |
| 239. | 3-(3-isoxazolyl)-Ph |
| 240. | 3-(4-isoxazolyl)-Ph |
| 241. | 3-(5-isoxazolyl)-Ph |
| 242. | 1-methyl-5-pyrazolyl |
| 243. | 1-ethyl-5-pyrazolyl |
| 244. | [1,3,4]-oxadiazol-2-yl |
| 245. | CO—NH-(2-ethylpyrazol-3-yl) |
| 246. | CO—NH-(thiazol-2-yl) |

-continued

| | |
|---|---|
| 247. | CO—NH-(isoxazol-3-yl) |
| 248. | 5-acetyl-4-methylthiazol-2-yl |
| 249. | 5-acetyl-4-methyloxazol-2-yl |
| 250. | 5-acetyl-4-methylimidazol-2-yl |
| 251. | 3-acetyl-5-[(CH3)2N—CO]-Ph |
| 252. | 3-acetyl-5-[(CH3)NH—CO]-Ph |
| 253. | 3-acetyl-5-[H2N-CO]-Ph |
| 254. | 3-acetyl-5-[morpholin-1-yl-CO]-Ph |
| 255. | 3-acetyl-5-F—Ph |
| 256. | 3-acetyl-5-Cl—Ph |
| 257. | 3-acetyl-5-Br—Ph |
| 258. | 3-acetyl-4-F—Ph |
| 259. | 3-acetyl-4-Cl—Ph |
| 260. | 3-acetyl-4-Br—Ph |
| 261. | 3-acetyl-5-CF3—Ph |
| 262. | 3-acetyl-4-CF3—Ph |
| 263. | 3-acetyl-2-CH3O—Ph |
| 264. | 3-acetyl-4-CH3O—Ph |
| 265. | 3-acetyl-5-CH3O—Ph |
| 266. | 3-acetyl-6-CH3O—Ph |
| 267. | 3-acetyl-5-CH3—Ph |
| 268. | 3-acetyl-5-CH3CH2—Ph |
| 269. | 4-acetyl-5-[morpholin-1-yl—CO]-Ph |
| 270. | 4-acetyl-5-F—Ph |
| 271. | 4-acetyl-5-Cl—Ph |
| 272. | 4-acetyl-5-Br—Ph |
| 273. | 4-acetyl-3-CF3—Ph |
| 274. | 4-acetyl-2-CH3O—Ph |
| 275. | 4-acetyl-4-CH3O—Ph |
| 276. | 3-acetyl-5-(1-methyltetrazol-5-yl)-Ph |
| 277. | 3-acetyl-5-(1-ethyltetrazol-5-yl)-Ph |
| 278. | 3-acetyl-5-(1-cyclopropyltetrazol-5-yl)-Ph |
| 279. | 3-acetyl-5-(oxazol-2-yl)-Ph |
| 280. | 3-acetyl-5-(isoxazol-3-yl)-Ph |
| 281. | 3-acetyl-5-(isoxazol-5-yl)-Ph |
| 282. | 3-acetyl-5-(pyrazol-1-yl)-Ph |
| 283. | 3-acetyl-5-(1,2,4-triazol-1-yl)-Ph |
| 284. | 3-acetyl-5-(CH2OH)—Ph |
| 285. | 3-acetyl-5-(furan-2-yl)-Ph |
| 286. | 3-acetyl-5-(furan-3-yl)-Ph |
| 287. | 3-acetyl-5-(thien-2-yl)-Ph |
| 288. | 3-acetyl-5-(thien-3-yl)-Ph |
| 289. | 3-acetyl-5-CN—Ph |
| 290. | 3-acetyl-5-(CC)—Ph |
| 291. | 3-acetyl-5-(isopropyl)-Ph |
| 292. | 3-acetyl-5-(SO2NH2)—Ph |
| 293. | 3-acetyl-5-(CO-4-morpholine)-Ph |
| 294. | 3-isopropyl-5-(1-methyltetrazol-5-yl)-Ph |
| 295. | 3-SO2NH2-5-(1-methyltetrazol-5-yl)-Ph |
| 296. | 3,5-di(OMe)—Ph |
| 297. | 3,4,5-tri(Ome)—Ph |

$R^5$ or $R^{17}$

| | |
|---|---|
| 1. | H |
| 2. | 4-F—Ph |
| 3. | 2-F—Ph |
| 4. | 2,4-diF—Ph |
| 5. | 4-Cl—Ph |
| 6. | 2-Cl—Ph |
| 7. | 2,4-diCl—Ph |
| 8. | 3-OCH3—Ph |
| 9. | 2-thienyl |
| 10. | 3-thienyl |
| 11. | 2-furanyl |
| 12. | 3-furanyl |
| 13. | 2-pyridyl |
| 14. | 3-pyridyl |
| 15. | 4-pyridyl |
| 16. | 3-indolyl |
| 17. | 5-indolyl |
| 18. | 5-indazolyl |
| 19. | 5-benzimidazolyl |
| 20. | 5-benzothiazolyl |
| 21. | 5-benzoxazolyl |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437-2448 (1996) and Uguccioni et al., J. Clin. Invest., 100, 1137-1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105-110 (1991), can be utilized in such assays. In particular, the compound of the present invention have activity in binding to the CCR-3 receptor in the aforementioned assays. As used herein, "activity" is intended to mean a compound demonstrating an IC50 of 10 μM or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 μg/ml protamine in phosphate buffered saline, pH 7.2, for ten minutes at room temperature. Plates are washed three times with phosphate buffered saline and incubated with phosphate buffered saline for thirty minutes at room temperature. For binding, 50 μl of binding buffer (0.5% bovine serum albumen, 20 mM HEPES buffer and 5 mM magnesium chloride in RPMI 1640 media) with or without a test concentration of a compound present at a known concentration is combined with 50 μl of 125-I labeled human eotaxin (to give a final concentration of 150 pM radioligand) and 50 μl of cell suspension in binding buffer containing $5 \times 10^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966-974 (1988). In particular, the compound of the present invention have activity in inhibition of the migration of eosinophils in the aforementioned assays. As used herein, "activity" is intended to mean a compound demonstrating an IC50 of 10 µM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1\times10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 µl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30-45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 µM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

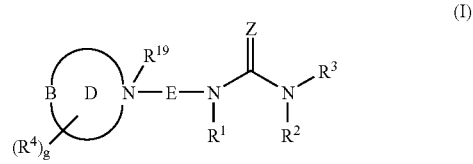

or stereoisomers or pharmaceutically acceptable salts thereof, wherein:

Ring D is a morpholinyl ring containing at least one carbonyl or sulfonyl therein;

$R^4$ is selected from H, $R^5$ and $R^{13}$;

with the proviso that Ring D contains at least one $R^5$;

Z is selected from O, S, $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

E is —$(CR^7CR^8)$—$(CR^9R^{10})_v$—$(CR^{11}R^{12})$, —(C=O)—$(CR^9R^{10})_v$—$(CR^{11}R^{12})$—, —$(SO_2)$—$(CR^9R^{10})_v$—$(CR^{11}R^{12})$—,

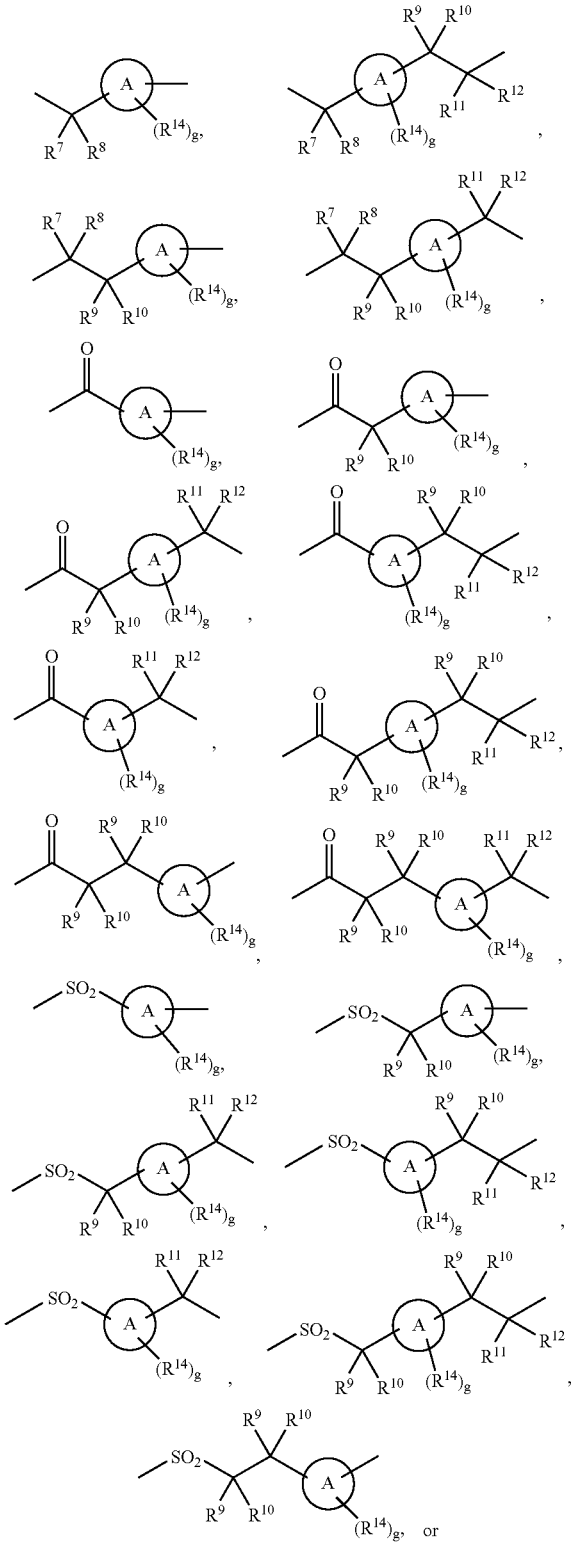

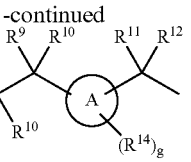

Ring A is a $C_{3-8}$ carbocyclic residue;

$R^1$ and $R^2$ are independently selected from H, $C_{1-8}$ alkyl, $C_{3-8}$ alkenyl, $C_{3-8}$ alkynyl, and a $(CH_2)_r$—$C_{3-10}$ carbocyclic residue substituted with 0-5 $R^a$;

$R^a$, at each occurrence, is independently selected from $C_{1-4}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^b R^b$, $(CH_2)_r OH$, $(CH_2)_r OR^c$, $(CH_2)_r SH$, $(CH_2)_r SR^c$, $(CH_2)_r C(O)R^b$, $(CH_2)_r C(O)NR^b R^b$, $(CH_2)_r NR^b C(O)R^b$, $(CH_2)_r C(O)OR^b$, $(CH_2)_r OC(O)R^c$, $(CH_2)_r CH(=NR^b)NR^b R^b$, $(CH_2)_r NHC(=NR^b)NR^b R^b$, $(CH_2)_r S(O)_p R^c$, $(CH_2)_r S(O)_2 NR^b R^b$, $(CH_2)_r NR^b S(O)_2 R^c$, and $(CH_2)_r$phenyl;

$R^b$, at each occurrence, is independently selected from H, $C_{1-6}$ alkyl, $C_{3-6}$ cycloalkyl, and phenyl;

$R^c$, at each occurrence, is independently selected from $C_{1-6}$ alkyl, $C_{3-6}$ cycloalkyl, and phenyl;

$R^3$ is selected from a $(CR^{3a}R^{3b})_r$—$C_{3-8}$ carbocyclic residue substituted with 0-5 $R^{15}$; and a $(CR^{3a}R^{3b})_r$-5-10 membered heterocyclic system containing 1-4 heteroatoms selected from N, O, and S, substituted with 0-3 $R^{15}$;

$R^{3a}$ and $R^{3b}$, at each occurrence, are independently selected from H, $C_{1-6}$ alkyl, $(CH_2)_r C_{3-6}$ cycloalkyl, and phenyl;

$R^5$ is selected from a $(CR^{5a}R^{5b})_t$—$C_{3-10}$ carbocyclic residue substituted with 0-5 $R^{16}$ and a $(CR^{5a}R^{5b})_t$-5-10 membered heterocyclic system containing 1-4 heteroatoms selected from N, O, and S, substituted with 0-3 $R^{16}$;

$R^{5a}$ and $R^{5b}$, at each occurrence, are selected from H, $C_{1-6}$ alkyl, $(CH_2)_r C_{3-6}$ cycloalkyl, and phenyl;

$R^7$, is selected from H, $C_{1-6}$ alkyl, $C_{2-8}$ alkenyl, $C_{2-8}$ alkynyl, $(CH_2)_q OH$, $(CH_2)_q SH$, $(CH_2)_q OR^{7d}$, $(CH_2)_q SR^{7d}$, $(CH_2)_q NR^{7a} R^{7a}$, $(CH_2)_q C(O)OH$, $(CH_2)_q C(O)R^{7b}$, $(CH_2)_q C(O)NR^{7a} R^{7a}$, $(CH_2)_q NR^{7a} C(O)R^{7a}$, $(CH_2)_q NR^{7a} C(O)H$, $(CH_2)_q C(O)OR^{7b}$, $(CH_2)_q OC(O)R^{7b}$, $(CH_2)_q S(O)_p R^{7b}$, $(CH_2)_q S(O)_2 NR^{7a} R^{7a}$, $(CH_2)_q NR^{7a} S(O)_2 R^{7b}$, $C_{1-6}$ haloalkyl, a $(CH_2)_r$—$C_{3-10}$ carbocyclic residue substituted with 0-3 $R^{7c}$, and a $(CH_2)_r$-5-10 membered heterocyclic system containing 1-4 heteroatoms selected from N, O, and S, substituted with 0-2 $R^{7c}$;

$R^{7a}$, at each occurrence, is independently selected from H, $C_{1-6}$ alkyl, $C_{2-8}$ alkenyl, $C_{2-8}$ alkynyl, $(CH_2)_r C_{3-6}$ cycloalkyl, a $(CH_2)_r$—$C_{3-10}$ carbocyclic residue substituted with 0-5 $R^{7e}$, and a $(CH_2)_r$-5-10 membered heterocyclic system containing 1-4 heteroatoms selected from N, O, and S, substituted with 0-3 $R^{7e}$;

$R^{7b}$, at each occurrence, is independently selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{7e}$, and a $(CH_2)_r$-5-6 membered heterocyclic system containing 1-4 heteroatoms selected from N, O, and S, substituted with 0-3 $R^{7e}$;

$R^{7c}$, at each occurrence, is independently selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{7f} R^{7f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{7b}$, $(CH_2)_r C(O)NR^{7f} R^{7f}$, $(CH_2)_r NR^{7f} C(O)R^{7a}$, $(CH_2)_r C(O)OC_{1-4}$ alkyl, $(CH_2)_r OC(O)R^{7b}$, $(CH_2)_r C(=NR^{7f})NR^{7f} R^{7f}$, $(CH_2)_r S $(O)_pR^{7b}$, $(CH_2)_rNHC(=NR^{7f})NR^{7f}R^{7f}$, $(CH_2)_rS(O)_2$ $NR^{7f}R^{7f}$, $(CH_2)_rNR^{7f}S(O)_2R^{7b}$, and $(CH_2)_r$phenyl substituted with 0-3 $R^{7e}$;

$R^{7d}$, at each occurrence, is independently selected from methyl, $CF_3$, $C_{2-6}$ alkyl substituted with 0-3 $R^{7e}$, alkenyl, alkynyl, and a $C_{3-10}$ carbocyclic residue substituted with 0-3 $R^{7e}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$phenyl substituted with 0-3 $R^{8a}$;

$R^{8a}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{8f}R^{8f}$, and $(CH_2)_r$phenyl;

alternatively, $R^7$ and $R^8$ join to form $C_{3-7}$ cycloalkyl, or $=NR^{8b}$;

$R^{8b}$ is selected from H, $C_{1-6}$ alkyl, $C_{3-6}$ cycloalkyl, OH, CN, and $(CH_2)_r$-phenyl;

$R^{8f}$, at each occurrence, is independently selected from H, $C_{1-6}$ alkyl, and $C_{3-6}$ cycloalkyl;

$R^9$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CHR')_rOR^{9d}$, $(CHR')_rSR^{9d}$, $(CHR')_rNR^{9a}R^{9a}$, $(CHR')_rC(O)OH$, $(CHR')_rC(O)R^{9b}$, $(CHR')_rC(O)NR^{9a}R^{9a}$, $(CHR')_rNR^{9a}C(O)R^{9b}$, $(CHR')_rNR^{9a}C(O)H$, $(CHR')_rC(O)OR^{9b}$, $(CHR')_rOC(O)R^{9b}$, $(CHR')_rOC(O)NR^{9a}R^{9a}$, $(CHR')_rNR^{9a}C(O)OR^{9b}$, $(CHR')_rS(O)_pR^{9b}$, $(CHR')_rS(O)_2NR^{9a}R^{9a}$, $(CHR')_rNR^{9a}S(O)_2R^{9b}$, $C_{1-6}$ haloalkyl, a $(CHR')_r$—$C_{3-10}$ carbocyclic residue substituted with 0-5 $R^{9c}$, and a $(CHR')_r$-5-10 membered heterocyclic system containing 1-4 heteroatoms selected from N, O, and S, substituted with 0-3 $R^{9c}$;

$R^{9a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{9e}$, and a $(CH_2)_r$-4-10 membered heterocyclic system containing 1-4 heteroatoms selected from N, O, and S, substituted with 0-3 $R^{9e}$;

alternatively, two $R^{9a}$s, along with the N to which they are attached, join to form a 5-6 membered heterocyclic system containing 1-2 heteroatoms selected from $NR^{9g}$, O, and S and optionally fused with a benzene ring or a 6-membered aromatic heterocycle;

$R^{9b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{9e}$, and a $(CH_2)_r$-4-6 membered heterocyclic system containing 1-4 heteroatoms selected from N, O, and S, substituted with 0-3 $R^{9e}$;

$R^{9c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOR^{9b}$, $(CH_2)_rSR^{9b}$, $(CH_2)_rC(O)OH$, $(CH_2)_rC(O)R^{9b}$, $(CH_2)_rC(O)NR^{9f}R^{9f}$, $(CH_2)_rNR^{9f}C(O)R^{9b}$, $(CH_2)_rC(O)OR^{9b}$, $(CH_2)_rOC(O)R^{9b}$, $(CH_2)_rC(=NR^{9f})NR^{9f}R^{9f}$, $(CH_2)_rS(O)_pR^{9b}$, $(CH_2)_rNHC(=NR^{9f})NR^{9f}R^{9f}$, $(CH_2)_rS(O)_2NR^{9f}R^{9f}$, $(CH_2)_rNR^{9f}S(O)_2R^{9b}$, and $(CH_2)_r$phenyl substituted with 0-3 $R^{9e}$;

$R^{9d}$, at each occurrence, is independently selected from methyl, $CF_3$, $C_{2-6}$ alkyl residue substituted with 0-3 $R^{9e}$, $C_{3-6}$ alkenyl, $C_{3-6}$ alkynyl, a $C_{3-10}$ carbocyclic residue substituted with 0-3 $R^{9c}$, and a 5-6 membered heterocyclic system containing 1-4 heteroatoms selected from the group consisting of N, O, and S substituted with 0-3 $R^{9c}$;

$R^{9e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl, wherein the phenyl on the $(CH_2)_r$phenyl is substituted with 0-5 substituents selected from F, Cl, Br, I, $NO_2$, $C_{1-6}$alkyl, OH, and $NR^{9f}R^{9f}$;

$R^{9f}$, at each occurrence, is independently selected from H, $C_{1-6}$ alkyl, and $C_{3-6}$ cycloalkyl;

$R^{9g}$ is selected from H, $C_{1-6}$ alkyl, $C_{3-6}$ cycloalkyl, $(CH_2)_r$phenyl, $C(O)R^{9f}$, $C(O)OR^{9h}$, and $SO_2R^{9h}$;

$R^{9h}$, at each occurrence, is independently selected from $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{10d}$, $(CH_2)_rSR^{10d}$, $(CH_2)_rNR^{10a}R^{10a}$, $(CH_2)_rC(O)OH$, $(CH_2)_rC(O)R^{10b}$, $(CH_2)_rC(O)NR^{10a}R^{10a}$, $(CH_2)_rNR^{10a}C(O)R^{10a}$, $(CH_2)_rNR^{10a}C(O)H$, $(CH_2)_rC(O)OR^{10b}$, $(CH_2)_rOC(O)R^{10b}$, $(CH_2)_rOC(O)NR^{10a}R^{10a}$, $(CH_2)_rNR^{10a}C(O)OR^{10b}$, $(CH_2)_rS(O)_pR^{10b}$, $(CH_2)_rS(O)_2NR^{10a}R^{10a}$, $(CH_2)_rNR^{10a}S(O)_2R^{10b}$, $C_{1-6}$ haloalkyl, a $(CH_2)_r$—$C_{3-10}$ carbocyclic residue substituted with 0-5 $R^{10c}$, and a $(CH_2)_r$-5-10 membered heterocyclic system containing 1-4 heteroatoms selected from N, O, and S, substituted with 0-3 $R^{10c}$;

$R^{10a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{10e}$, and a $(CH_2)_r$-4-10 membered heterocyclic system containing 1-4 heteroatoms selected from N, O, and S, substituted with 0-3 $R^{10e}$;

alternatively, two $R^{10a}$s, along with the N to which they are attached, join to form a 5-6 membered heterocyclic system containing 1-2 heteroatoms selected from $NR^{10g}$, O, and S and optionally fused with a benzene ring or a 6-membered aromatic heterocycle;

$R^{10b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-2 $R^{10e}$, and a $(CH_2)_r$-4-6 membered heterocyclic system containing 1-4 heteroatoms selected from N, O, and S, substituted with 0-3 $R^{10e}$;

$R^{10c}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{10f}R^{10f}$, $(CH_2)_rOH$, $(CH_2)_rOR^{10b}$, $(CH_2)_rSR^{10b}$, $(CH_2)_rC(O)OH$, $(CH_2)_rC(O)R^{10b}$, $(CH_2)_rC(O)NR^{10f}R^{10f}$, $(CH_2)_rNR^{10f}C(O)R^{10a}$, $(CH_2)_rC(O)OR^{10b}$, $(CH_2)_rOC(O)R^{10b}$, $(CH_2)_rC(=NR^{10f})NR^{10f}R^{10f}$, $(CH_2)_rS(O)_pR^{10b}$, $(CH_2)_rNHC(=NR^{10f})NR^{10f}R^{10f}$, $(CH_2)_rS(O)_2NR^{10f}R^{10f}$, $(CH_2)_rNR^{10f}S(O)_2R^{10b}$, and $(CH_2)_r$phenyl substituted with 0-3 $R^{10e}$;

$R^{10d}$, at each occurrence, is independently selected from methyl, $CF_3$, $C_{2-6}$ alkyl substituted with 0-3 $R^{10e}$, $C_{3-6}$ alkenyl, $C_{3-6}$ alkynyl, and a $C_{3-10}$ carbocyclic residue substituted with 0-3 $R^{10c}$;

$R^{10e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_r$ OC$_{1-5}$ alkyl, OH, SH, (CH$_2$)$_r$SC$_{1-5}$ alkyl, (CH$_2$)$_r$NR$^{10f}$R$^{10f}$, and (CH$_2$)$_r$phenyl;

R$^{10f}$, at each occurrence, is independently selected from H, C$_{1-6}$ alkyl, and C$_{3-6}$ cycloalkyl;

R$^{10g}$ is selected from H, C$_{1-6}$ alkyl, C$_{3-6}$ cycloalkyl, (CH$_2$)$_r$phenyl, C(O)R$^{10f}$, SO$_2$R$^{10h}$, and C(O)O R$^{10h}$;

R$^{10h}$, at each occurrence, is independently selected from H, C$_{1-6}$ alkyl, C$_{3-6}$ cycloalkyl;

alternatively, R$^9$ and R$^{10}$ join to form =O, a C$_{3-10}$ cycloalkyl, a 5-6-membered lactone or lactam, or a 4-6-membered saturated heterocycle containing 1-2 heteroatoms selected from O, S, and NR$^{10g}$ and optionally fused with a benzene ring or a 6-membered aromatic heterocycle;

R$^{11}$, is selected from H, C$_{1-6}$ alkyl, C$_{2-8}$ alkenyl, C$_{2-8}$ alkynyl, (CR'R')$_q$OH, (CH$_2$)$_q$SH, (CR'R')$_q$OR$^{11d}$, (CHR')$_q$SR$^{11d}$, (CR'R')$_q$NR$^{11a}$R$^{11a}$, (CHR')$_r$C(O)OH, (CHR')$_r$C(O)R$^{11b}$, (CHR')$_r$C(O)NR$^{11a}$R$^{11a}$, (CHR')$_q$NR$^{11a}$C(O)R$^{11a}$, (CHR')$_q$OC(O)NR$^{11a}$R$^{11a}$, (CHR')$_q$NR$^{11a}$C(O)OR$^{11b}$, (CHR')$_q$NR$^{11a}$C(O)NHR$^{11a}$, (CHR')$_r$C(O)OR$^{11b}$, (CHR')$_q$OC(O)R$^{11b}$, (CHR')$_q$S(O)$_p$R$^{11b}$, (CHR')$_q$S(O)$_2$NR$^{11a}$R$^{11a}$, (CHR')$_q$NR$^{11a}$S(O)$_2$R$^{11b}$, C$_{1-6}$ haloalkyl, a (CHR')$_r$—C$_{3-10}$ carbocyclic residue substituted with 0-5 R$^{11c}$, and a (R'R$^{17}$)$_r$-5-10 membered heterocyclic system containing 1-4 heteroatoms selected from N, O, and S, substituted with 0-3 R$^{11c}$;

R$^{11a}$, at each occurrence, is independently selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{11e}$, and a (CH$_2$)$_r$-5-10 membered heterocyclic system containing 1-4 heteroatoms selected from N, O, and S, substituted with 0-3 R$^{11e}$;

alternatively, two R$^{11a}$s, along with the N to which they are attached, join to form a 5-6 membered heterocyclic system containing 1-2 heteroatoms selected from NR$^{11g}$, O, and S and optionally fused with a benzene ring or a 6-membered aromatic heterocycle;

R$^{11b}$, at each occurrence, is independently selected from C$_{1-6}$ alkyl, C$_{3-8}$ alkenyl, C$_{3-8}$ alkynyl, a (CH$_2$)$_r$—C$_{3-6}$ carbocyclic residue substituted with 0-2 R$^{11e}$, and a (CH$_2$)$_r$-4-6 membered heterocyclic system containing 1-4 heteroatoms selected from N, O, and S, substituted with 0-3 R$^{11e}$;

R$^{11c}$, at each occurrence, is independently selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{11f}$R$^{11f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{11b}$, (CH$_2$)$_r$C(O)NR$^{11f}$R$^{11f}$, (CH$_2$)$_r$NR$^{11f}$C(O)R$^{11a}$, (CH$_2$)$_r$C(O)OC$_{1-4}$ alkyl, (CH$_2$)$_r$OC(O)R$^{11b}$, (CH$_2$)$_r$S(O)$_2$ NR$^{11f}$R$^{11f}$, (CH$_2$)$_r$NR$^{11f}$S(O)$_2$R$^{11b}$, and (CH$_2$)$_r$phenyl substituted with 0-3 R$^{11e}$;

R$^{11d}$, at each occurrence, is independently selected from methyl, CF$_3$, C$_{2-6}$ alkyl substituted with 0-3 R$^{11e}$, C$_{3-6}$ alkenyl, C$_{3-6}$ alkynyl, and a C$_{3-10}$ carbocyclic residue substituted with 0-3 R$^{11c}$;

R$^{11e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{11f}$R$^{11f}$, and (CH$_2$)$_r$phenyl, wherein the phenyl on the (CH$_2$)$_r$phenyl is substituted with 0-5 substituents selected from F, Cl, Br, I, NO$_2$, C$_{1-6}$alkyl, OH, and NR$^{11f}$R$^{11f}$;

R$^{11f}$, at each occurrence, is independently selected from H, C$_{1-6}$ alkyl, and C$_{3-6}$ cycloalkyl;

R$^{11g}$ is selected from H, C$_{1-6}$ alkyl, C$_{3-6}$ cycloalkyl, (CH$_2$)$_r$phenyl, C(O)R$^{11f}$, C(O)OR$^{11h}$, and SO$_2$R$^{11h}$;

R$^{11h}$, at each occurrence, is independently selected from C$_{1-6}$ alkyl, and C$_{3-6}$ cycloalkyl;

R$^{12}$, is selected from H, C$_{1-6}$ alkyl, C$_{2-8}$ alkenyl, C$_{2-8}$ alkynyl, (CHR')$_q$OH, (CH$_2$)$_q$SH, (CHR')$_q$OR$^{12d}$, (CH$_2$)$_q$SR$^{12d}$, (CHR')$_q$NR$^{12a}$R$^{12a}$, (CH$_2$)$_r$C(O)OH, (CH$_2$)$_r$C(O)R$^{12b}$, (CH$_2$)$_r$C(O)NR$^{12a}$R$^{12a}$, (CH$_2$)$_q$NR$^{12a}$C(O)R$^{12a}$, (CH$_2$)$_r$OC(O)NR$^{12a}$R$^{12a}$, (CH$_2$)$_r$NR$^{12a}$C(O)OR$^{12b}$, (CH$_2$)$_q$NR$^{12a}$C(O)NHR$^{12a}$, (CH$_2$)$_r$C(O)OR$^{12b}$, (CH$_2$)$_q$OC(O)R$^{12b}$, (CH$_2$)$_q$S(O)$_p$R$^{12b}$, (CH$_2$)$_q$S(O)$_2$NR$^{12a}$R$^{12a}$, (CH$_2$)$_q$NR$^{12a}$S(O)$_2$R$^{12b}$, C$_{1-6}$ haloalkyl, a (CH$_2$)$_r$—C$_{3-10}$ carbocyclic residue substituted with 0-5 R$^{12c}$, and a (CR'R$^{17}$)$_r$-5-10 membered heterocyclic system containing 1-4 heteroatoms selected from N, O, and S, substituted with 0-3 R$^{12c}$;

R$^{12a}$, at each occurrence, is independently selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0-5 R$^{12e}$, and a (CH$_2$)$_r$-4-10 membered heterocyclic system containing 1-4 heteroatoms selected from N, O, and S, substituted with 0-3 R$^{12e}$;

alternatively, two R$^{12a}$s, along with the N to which they are attached, join to form a 5-6 membered heterocyclic system containing 1-2 heteroatoms selected from NR$^{12g}$, O, and S and optionally fused with a benzene ring or a 6-membered aromatic heterocycle;

R$^{12b}$, at each occurrence, is independently selected from C$_{1-6}$ alkyl, C$_{3-8}$ alkenyl, C$_{3-8}$ alkynyl, a (CH$_2$)$_r$—C$_{3-6}$ carbocyclic residue substituted with 0-2 R$^{12e}$, and a (CH$_2$)$_r$-4-6 membered heterocyclic system containing 1-4 heteroatoms selected from N, O, and S, substituted with 0-3 R$^{12e}$;

R$^{12c}$, at each occurrence, is independently selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{12f}$R$^{12f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{12b}$, (CH$_2$)$_r$ C(O)NR$^{12f}$R$^{12f}$, (CH$_2$)$_r$NR$^{12f}$C(O)R$^{12a}$, (CH$_2$)$_r$C(O)OC$_{1-4}$ alkyl, (CH$_2$)$_r$OC(O)R$^{12b}$, (CH$_2$)$_r$C(=NR$^{12f}$)NR$^{12f}$R$^{12f}$, (CH$_2$)$_r$NHC(=NR$^{12f}$)NR$^{12f}$R$^{12f}$, (CH$_2$)$_r$S(O)$_p$R$^{12b}$, (CH$_2$)$_r$S(O)$_2$NR$^{12f}$R$^{12f}$, (CH$_2$)$_r$NR$^{12f}$S(O)$_2$ R$^{12b}$, and (CH$_2$)$_r$phenyl substituted with 0-3 R$^{12e}$;

R$^{12d}$, at each occurrence, is independently selected from methyl, CF$_3$, C$_{2-6}$ alkyl substituted with 0-3 R$^{12e}$, C$_{3-6}$ alkenyl, C$_{3-6}$ alkynyl, and a C$_{3-10}$ carbocyclic residue substituted with 0-3 R$^{12e}$;

R$^{12e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{12f}$R$^{12f}$, and (CH$_2$)$_r$phenyl;

R$^{12f}$, at each occurrence, is independently selected from H, C$_{1-6}$ alkyl, and C$_{3-6}$ cycloalkyl;

R$^{12g}$ is selected from H, C$_{1-6}$ alkyl, C$_{3-6}$ cycloalkyl, (CH$_2$)$_r$phenyl, C(O)R$^{12f}$, C(O)OR$^{12h}$, and SO$_2$R$^{12h}$;

R$^{12h}$, at each occurrence, is independently selected from C$_{1-6}$ alkyl, and C$_{3-6}$ cycloalkyl;

alternatively, R$^{11}$ and R$^{12}$ join to form a C$_{3-10}$ cycloalkyl, a 5-6-membered lactone or lactam, or a 4-6-membered saturated heterocycle containing 1-2 heteroatoms selected from O, S, and NR$^{11g}$ and optionally fused with a benzene ring or a 6-membered aromatic heterocycle;

R$^{13}$, at each occurrence, is independently selected from C$_{1-6}$ alkyl, C$_{2-8}$ alkenyl, C$_{2-8}$ alkynyl, C$_{3-6}$ cycloalkyl, (CF$_2$)$_w$CF$_3$, (CH$_2$)$_q$NR$^{13a}$R$^{13a}$, (CHR')$_q$OH, (CH$_2$)$_q$OR$^{13b}$, (CH$_2$)$_q$SH, (CH$_2$)$_q$SR$^{13b}$, (CH$_2$)$_w$C(O)OH, (CH$_2$)$_w$C(O)R$^{13b}$, (CH$_2$)$_w$C(O)NR$^{13a}$R$^{13a}$, (CH$_2$)$_q$NR$^{13a}$C(O)R$^{13a}$, (CH$_2$)$_w$C(O)OR$^{13b}$, (CH$_2$)$_q$OC(O)

$R^{13b}$, $(CH_2)_wS(O)_pR^{13b}$, $(CH_2)_wS(O)_2NR^{13a}R^{13a}$, $(CH_2)_qNR^{13d}S(O)_2R^{13b}$, and $(CH_2)_w$-phenyl substituted with 0-3 $R^{13c}$;

$R^{13a}$, at each occurrence, is independently selected from H, $C_{1-6}$ alkyl, $C_{3-6}$ cycloalkyl, and phenyl substituted with 0-3 $R^{13c}$;

$R^{13b}$, at each occurrence, is independently selected from $C_{1-6}$ alkyl, $C_{3-6}$ cycloalkyl, and phenyl substituted with 0-3 $R^{13c}$;

$R^{13c}$, at each occurrence, is independently selected from $C_{1-6}$ alkyl, $C_{3-6}$ cycloalkyl, Cl, F, Br, I, CN, $NO_2$, $(CF_2)_r$ $CF_3$, $(CH_2)_rOC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is independently selected from H, $C_{1-6}$ alkyl, and $C_{3-6}$ cycloalkyl;

$R^{14}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a}$, $(CHR')_rOH$, $(CHR')_rO(CHR')_rR^{14d}$, $(CHR')_rSH$, $(CHR')_rC(O)H$, $(CHR')_rS(CHR')_rR^{14d}$, $(CHR')_rC(O)OH$, $(CHR')_rC(O)(CHR')_rR^{14b}$, $(CHR')_rC(O)NR^{14a}R^{14a}$, $(CHR')_rNR^{14f}C(O)(CHR')_rR^{14b}$, $(CHR')_rOC(O)NR^{14a}R^{14a}$, $(CHR')_rNR^{14f}C(O)O(CHR')_rR^{14b}$, $(CHR')_rC(O)O(CHR')_rR^{14d}$, $(CHR')_rOC(O)(CHR')_rR^{14b}$, $(CHR')_rC(=NR^{14f})NR^{14a}R^{14a}$, $(CHR')_rNHC(=NR^{14f})NR^{14f}R^{14f}$, $(CHR')_rS(O)_p(CHR')_rR^{14b}$, $(CHR')_rS(O)_2NR^{14a}R^{14a}$, $(CHR')_rNR^{14f}S(O)_2(CHR')_rR^{14b}$, $C_{1-6}$ haloalkyl, $C_{2-8}$ alkenyl substituted with 0-3 R', $C_{2-8}$ alkynyl substituted with 0-3 R', $(CHR')_r$phenyl substituted with 0-3 $R^{14e}$, and a $(CH_2)_r$-4-10 membered heterocyclic system containing 1-4 heteroatoms selected from N, O, and S, substituted with 0-2 $R^{15e}$, or two $R^{14}$ substituents on adjacent atoms on ring A form to join a 5-6 membered heterocyclic system containing 1-3 heteroatoms selected from N, O, and S substituted with 0-2 $R^{15e}$;

$R^{14a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{14e}$, and a $(CH_2)_r$-4-10 membered heterocyclic system containing 1-4 heteroatoms selected from N, O, and S, substituted with 0-2 $R^{14e}$;

$R^{14b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{14e}$, and $(CH_2)_r$- 4-6 membered heterocyclic system containing 1-4 heteroatoms selected from N, O, and S, substituted with 0-2 $R^{14e}$;

$R^{14d}$, at each occurrence, is independently selected from $C_{3-8}$ alkenyl, $C_{3-8}$ alkynyl, methyl, $CF_3$, $C_{2-6}$ alkyl substituted with 0-3 $R^{14e}$, a $(CH_2)_r$—$C_{3-10}$ carbocyclic residue substituted with 0-3 $R^{14e}$, and a $(CH_2)_r$4-6 membered heterocyclic system containing 1-4 heteroatoms selected from N, O, and S, substituted with 0-3 $R^{14e}$;

$R^{14e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_r$ $OC_{1-5}$ alkyl, OH, SH, $(CH_2)_rSC_{1-5}$ alkyl, $(CH_2)_r$ $NR^{14f}R^{14f}$, and $(CH_2)_r$phenyl;

$R^{14f}$, at each occurrence, is independently selected from H, $C_{1-6}$ alkyl, $C_{3-6}$ cycloalkyl, and phenyl;

$R^{15}$, at each occurrence, is independently selected from $C_{1-8}$ alkyl, $(CH_2)_rC_{3-6}$ cycloalkyl, Cl, Br, I, F, $NO_2$, CN, $(CR'R')_rNR^{15a}R^{15a}$, $(CR'R')_rOH$, $(CR'R')_rO(CHR')_r$ $R^{15d}$, $(CR'R')_rSH$, $(CR'R')_rC(O)H$, $(CR'R')_rS(CHR')_r$ $R^{15d}$, $(CR'R')_rC(O)OH$, $(CR'R')_rC(O)(CHR')_rR^{15b}$, $(CR'R')_rC(O)NR^{15a}R^{15a}$, $(CR'R')_rNR^{15f}C(O)(CHR')_r$ $R^{15b}$, $(CR'R')_rOC(O)NR^{15a}R^{15a}$, $(CR'R')_rNR^{15f}C(O)O$ $(CHR')_rR^{15b}$, $(CR'R')_rNR^{15f}C(O)NR^{15f}R^{15f}$, $(CR'R')_rC$ $(O)O(CHR')_rR^{15d}$, $(CR'R')_rOC(O)$ $(CHR')_rR^{15b}$, $(CR'R')_rC(=NR^{15f})NR^{15a}R^{15a}$, $(CR'R')_rNHC$ $(=NR^{15f})NR^{15f}R^{15f}$, $(CR'R')_rS(O)_p(CHR')_rR^{15b}$, $(CR'R')_rS(O)_2NR^{15a}R^{15a}$, $(CR'R')_rNR^{15f}S(O)_2(CHR')_r$ $R^{15b}$, $C_{1-6}$ haloalkyl, $C_{2-8}$ alkenyl substituted with 0-3 R', $C_{2-8}$ alkynyl substituted with 0-3 R', $(CR'R')_r$phenyl substituted with 0-3 $R^{15e}$, and a $(CH_2)_r$-5-10 membered heterocyclic system containing 1-4 heteroatoms selected from N, O, and S, substituted with 0-2 $R^{15e}$;

$R^{15a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{15e}$, and a $(CH_2)_r$-5-10 membered heterocyclic system containing 1-4 heteroatoms selected from N, O, and S, substituted with 0-2 $R^{15e}$;

alternatively, two $R^{15a}$s, along with the N to which they are attached, join to form a 5-6 membered heterocyclic system containing 1-2 heteroatoms selected from $NR^{15h}$, O, and S and optionally fused with a benzene ring or a 6-membered aromatic heterocycle;

$R^{15b}$, at each occurrence, is independently selected from $C_{1-6}$ alkyl, $C_{3-8}$ alkenyl, $C_{3-8}$ alkynyl, a $(CH_2)_r$—$C_{3-6}$ carbocyclic residue substituted with 0-3 $R^{15e}$, and $(CH_2)_r$- 5-6 membered heterocyclic system containing 1-4 heteroatoms selected from N, O, and S, substituted with 0-2 $R^{15e}$;

$R^{15d}$, at each occurrence, is independently selected from $C_{3-8}$ alkenyl, $C_{3-8}$ alkynyl, methyl, $CF_3$, $C_{2-6}$ alkyl substituted with 0-3 $R^{15e}$, a $(CH_2)_rC_{3-10}$ carbocyclic residue substituted with 0-3 $R^{15e}$, and a $(CH_2)_r$5-6 membered heterocyclic system containing 1-4 heteroatoms selected from N, O, and S, substituted with 0-3 $R^{15e}$;

$R^{15e}$, at each occurrence, is independently selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_r$ $OC_{1-5}$ alkyl, OH, SH, $(CH_2)_rSC_{1-5}$ alkyl, $(CH_2)_r$ $NR^{15f}R^{15f}$, $(CH_2)_r$phenyl, and a heterocycle substituted with 0-1 $R^{15g}$, wherein the heterocycle is selected from imidazole, thiazole, oxazole, pyrazole, 1,2,4-triazole, 1,2,3-triazole, isoxazole, and tetrazole,;

$R^{15f}$, at each occurrence, is independently selected from H, $C_{1-6}$ alkyl, $C_{3-6}$ cycloalkyl, and phenyl;

$R^{15g}$ is selected from methyl, ethyl, acetyl, and $CF_3$;

$R^{15h}$ is selected from H, $C_{1-6}$ alkyl, $C_{3-6}$ cycloalkyl, $(CH_2)_r$ phenyl, $C(O)R^{15f}$, $C(O)OR^{15i}$, and $SO_2R^{15i}$;

$R^{15i}$, at each occurrence, is independently selected from $C_{1-6}$ alkyl, $C_{3-6}$ cycloalkyl;

$R^{16}$, at each occurrence, is independently selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a}$, $(CHR')_rNR^{16f}S(O)_2(CHR')_r$ $R^{16b}$, $C_{1-6}$ haloalkyl, $C_{2-8}$ alkenyl substituted with 0-3 R', $C_{2-8}$ alkynyl substituted with 0-3 R', and $(CHR')_r$ phenyl substituted with 0-3 $R^{16e}$;

$R^{16a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{16e}$, and a (CH₂)$_r$-5-10 membered heterocyclic system containing 1-4 heteroatoms selected from N, O, and S, substituted with 0-2 R$^{16e}$;

R$^{16b}$, at each occurrence, is independently selected from C$_{1-6}$ alkyl, C$_{3-8}$ alkenyl, C$_{3-8}$ alkynyl, a (CH₂)$_r$C$_{3-6}$ carbocyclic residue substituted with 0-3 R$^{16e}$, and a (CH₂)$_r$ - 5-6 membered heterocyclic system containing 1-4 heteroatoms selected from N, O, and S, substituted with 0-2 R$^{16e}$;

R$^{16d}$, at each occurrence, is independently selected from C$_{3-8}$ alkenyl, C$_{3-8}$ alkynyl, methyl, CF₃, C$_{2-6}$ alkyl substituted with 0-3 R$^{16e}$, a (CH₂)$_r$—C$_{3-10}$ carbocyclic residue substituted with 0-3 R$^{16e}$, and a (CH₂)$_r$-5-6 membered heterocyclic system containing 1-4 heteroatoms selected from N, O, and S, substituted with 0-3 R$^{16e}$;

R$^{16e}$, at each occurrence, is independently selected from C$_{1-6}$ alkyl, C$_{2-8}$ alkenyl, C$_{2-8}$ alkynyl, (CH₂)$_r$C$_{3-6}$ cycloalkyl, Cl, F, Br, I, CN, NO₂, (CF₂)$_r$CF₃, (CH₂)$_r$ OC$_{1-5}$ alkyl, OH, SH, (CH₂)$_r$SC$_{1-5}$ alkyl, (CH₂)$_r$ NR$^{16f}$R$^{16f}$, and (CH₂)$_r$phenyl;

R$^{16f}$, at each occurrence, is independently selected from H, C$_{1-5}$ alkyl, and C$_{3-6}$ cycloalkyl, and phenyl;

R', at each occurrence, is independently selected from H, C$_{1-6}$ alkyl, C$_{2-8}$ alkenyl, C$_{2-8}$ alkynyl, (CH₂)$_r$C$_{3-6}$ cycloalkyl, and (CH₂)$_r$phenyl substituted with R$^e$;

R$^e$ is selected from C$_{1-6}$ alkyl, C$_{2-8}$ alkenyl, C$_{2-8}$ alkynyl, (CH₂)$_r$C$_{3-6}$ cycloalkyl, Cl, F, Br, I, CN, NO₂, (CF₂)$_r$CF₃, (CH₂)$_r$OC$_{1-5}$ alkyl, OH, SH, (CH₂)$_r$SC$_{1-5}$ alkyl, (CH₂)$_r$ NR'R$^f$, and (CH₂)$_r$phenyl;

R$^f$ is selected from H, C$_{1-5}$ alkyl, and C$_{3-6}$ cycloalkyl, and phenyl;

R$^{19}$ is absent, taken with the nitrogen to which it is attached to form an N-oxide, or selected from C$_{1-8}$ alkyl, C$_{2-8}$ alkenyl, C$_{2-8}$ alkynyl, (CH₂)$_r$C$_{3-6}$ cycloalkyl, (CH₂)$_q$C(O)R$^{19b}$, (CH₂)$_q$C(O)NR$^{19a}$R$^{19a}$, (CH₂)$_q$C(O)OR$^{19b}$, and a (CH₂)$_r$—C$_{3-10}$ carbocyclic residue substituted with 0-3 R$^{19c}$;

R$^{19a}$, at each occurrence, is selected from H, C$_{1-6}$ alkyl, (CH₂)$_r$C$_{3-6}$ cycloalkyl, and phenyl;

R$^{19b}$, at each occurrence, is selected from C$_{1-6}$ alkyl, C$_{2-8}$ alkenyl, (CH₂)$_r$C$_{3-6}$ cycloalkyl, C$_{2-8}$ alkynyl, and phenyl;

R$^{19c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO₂, (CF₂)$_r$CF₃, (CH₂)$_r$OC$_{1-5}$ alkyl, (CH₂)$_r$OH, (CH₂)$_r$ SC$_{1-5}$ alkyl, (CH₂)$_r$NR$^{19a}$R$^{19a}$, and (CH₂)$_r$phenyl;

alternatively, R$^{19}$ joins with R$^7$, R$^9$, or R$^{11}$ to form a 5, 6 or 7 membered piperidinium spirocycle or pyrrolidinium spirocycle substituted with 0-3 R$^a$;

g is selected from 0, 1, 2, and 3;
v is selected from 0, 1, and 2;
t is selected from 1 and 2;
w is selected from 0 and 1;
r is selected from 0, 1, 2, 3, 4, and 5;
q is selected from 1, 2, 3, 4, and 5; and
p is selected from 0, 1, and 2.

2. The compound of claim 1, wherein:
ring D is selected from

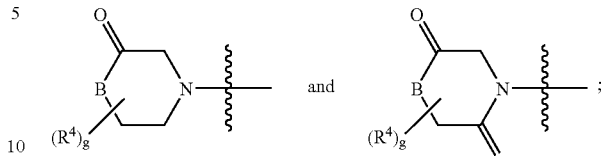

Z is selected from O, S, N(CN), and N(CONH₂);

R$^1$ and R$^2$ are independently selected from H and C$_{1-4}$ alkyl;

R$^{19}$ is absent, taken with the nitrogen to which it is attached to form an N-oxide, or selected from C$_{1-8}$ alkyl, (CH₂)$_r$ C$_{3-6}$ cycloalkyl, and (CH₂)$_r$phenyl substituted with 0-3 R$^{19c}$;

R$^{19c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO₂, (CF₂)$_r$CF₃, (CH₂)$_r$OC$_{1-5}$ alkyl, (CH₂)$_r$OH, (CH₂)$_r$ SC$_{1-5}$ alkyl, (CH₂)$_r$NR$^{19a}$R$^{19}$, and (CH₂)$_r$phenyl;

alternatively, R$^{19}$ joins with R$^7$, R$^9$, or R$^{11}$ to form a 5, 6 or 7 membered piperidinium spirocycle or pyrrolidinium spirocycle substituted with 0-3 R$^a$;

R$^{13}$, at each occurrence, is independently selected from C$_{1-4}$ alkyl, C$_{3-6}$ cycloalkyl, (CH₂)NR$^{13a}$R$^{13a}$, (CHR') OH, (CH₂)OR$^{13b}$, (CH₂)$_w$C(O)R$^{13b}$, (CH₂)$_w$C(O) NR$^{13a}$R$^{13a}$, (CH₂)NR$^{13d}$C(O)R$^{13a}$, (CH₂)$_w$S(O)₂ NR$^{13a}$R$^{13a}$, (CH₂)NR$^{13d}$S(O)₂R$^{13b}$, and (CH)$_w$-phenyl substituted with 0-3 R$^{13c}$;

R$^{13a}$, at each occurrence, is independently selected from H, C$_{1-6}$ alkyl, C$_{3-6}$ cycloalkyl, and phenyl substituted with 0-3 R$^{13c}$;

R$^{13b}$, at each occurrence, is independently selected from C$_{1-6}$ alkyl, C$_{3-6}$ cycloalkyl, and phenyl substituted with 0-3 R$^{13c}$;

R$^{13c}$, at each occurrence, is independently selected from C$_{1-6}$ alkyl, C$_{3-6}$ cycloalkyl, Cl, F, Br, I, CN, NO₂, (CF₂)$_r$ CF₃, (CH₂)$_r$OC$_{1-5}$ alkyl, (CH₂)$_r$OH, and (CH₂)$_r$ NR$^{13d}$R$^{13d}$;

R$^{13d}$, at each occurrence, is independently selected from H, C$_{1-6}$ alkyl, and C$_{3-6}$ cycloalkyl;

q is selected from 1, 2, and 3; and
r is selected from 0, 1, 2, and 3.

3. The compound of claim 2, wherein:
E is —(C=O)—(CR$^9$R$^{10}$)$_v$—(CR$^{11R12}$)—, —(CR$^7$R$^8$)— (CR$^9$R$^{10}$)$_v$—(CR$^{11R12}$),

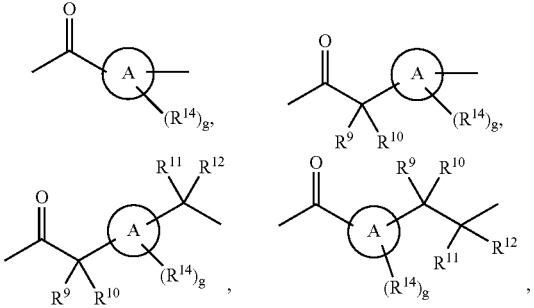

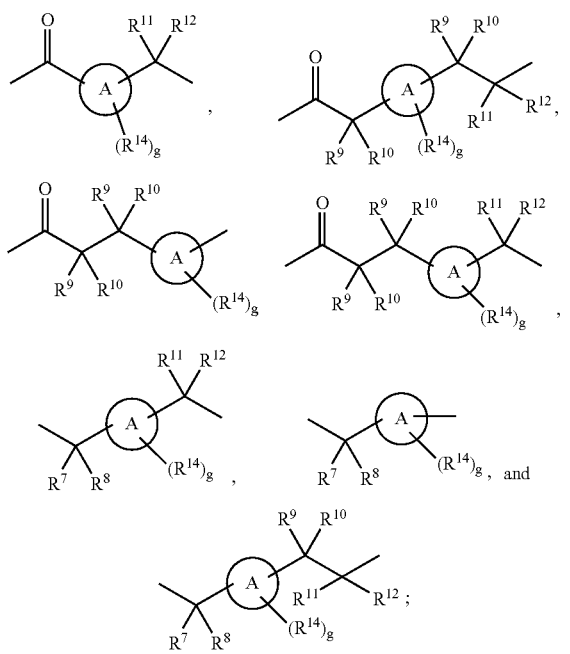

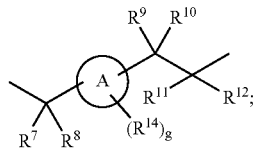

$R^3$ is selected from a $(CR^{3a}H)_r$—$C_{3-8}$ carbocyclic residue substituted with 0-5 $R^{15}$, wherein the carbocyclic residue is selected from phenyl, $C_{3-6}$ cycloalkyl, naphthyl, and adamantyl; and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^{5a}H)_r$-phenyl substituted with 0-5 $R^{16}$; and a $(CR^{5a}H)_r$-heterocyclic system substituted with 0-3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

4. The compound of claim 3, wherein
B is O,
E is —$(CR^7R^8)$—$(CR^9R^{10})_v$—$(CR^{11}R^{12})$,

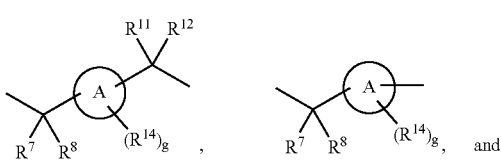

$R^1$ and $R^2$ are H;

$R^{16}$, at each occurrence, is independently selected from $C_{1-8}$ alkyl, $(CH_2)_r C_{3-6}$ cycloalkyl, $CF_3$, Cl, Br, I, F, $(CH_2)_r NR^{16a}R^{16a}$, $NO_2$, CN, OH, $(CH_2)_r OR^{16d}$, $(CH_2)_r C(O)R^{16b}$, $(CH_2)_r C(O)NR^{16a}R^{16a}$, $(CH_2)_r NR^{16f}C(O)R^{16b}$, $(CH_2)_r S(O)_p R^{16b}$, $(CH_2)_r S(O)_2 NR^{16a}R^{16a}$, $(CH_2)_r NR^{16f}S(O)_2 R^{6b}$, and $(CH_2)_r$phenyl substituted with 0-3 $R^{6e}$;

$R^{16a}$, at each occurrence, is independently selected from H, $C_{1-6}$ alkyl, $C_{3-6}$ cycloalkyl, and $(CH_2)_r$phenyl substituted with 0-3 $R^{16e}$;

$R^{16b}$, at each occurrence, is independently selected from $C_{1-6}$ alkyl, $C_{3-6}$ cycloalkyl, and $(CH_2)_r$phenyl substituted with 0-3 $R^{16e}$;

$R^{16d}$, at each occurrence, is independently selected from $C_{1-6}$ alkyl and phenyl;

$R^{16e}$, at each occurrence, is independently selected from $C_{1-6}$ alkyl, Cl, F, Br, I, CN, $NO_2$, $(CF_2)_r CF_3$, OH, and $(CH_2)_r OC_{1-5}$ alkyl; and $R^{16f}$, at each occurrence, is independently selected from H, and $C_{1-5}$ alkyl.

5. The compound of claim 4, wherein
E is —$(CR^7R^8)$—$(CR^9R^{10})$—$(CR^{11}R^{12})$;
B is or O;
$R^5$ is $CH_2$phenyl substituted with 0-3 $R^{16}$; and
r is selected from 0, 1, and 2.

6. The compound of claim 5, wherein:
Z is selected from O, N(CN) and NC(O)NH$_2$; and
$R^4$ is selected from H and $R^5$.

7. The compound of claim 6, wherein:
$R^3$ is a $C_{3-10}$ carbocyclic residue substituted with 0-3 $R^{15}$, wherein the carbocyclic residue is selected from cyclopropyl, cyclopentyl, cyclohexyl, phenyl, naphthyl and adamantyl, and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is independently selected from $C_{1-8}$ alkyl, $(CH_2)_r C_{3-6}$ cycloalkyl, $CF_3$, Cl, Br, I, F, $(CH_2)_r NR^{15a}R^{15a}$, $NO_2$, CN, OH, $(CH_2)_r OR^{15d}$, $(CH_2)_r C(O)R^{15b}$, $(CH_2)_r C(O)NR^{15a}R^{15a}$, $(CH_2)_r NR^{15f}C(O)R^{15b}$, $(CH_2)_r OC(O)NR^{15a}R^{15a}$, $(CH_2)_r NR^{15f}C(O)OR^{15b}$, $(CH_2)_r S(O)_p R^{15b}$, $(CH_2)_r S(O)_2 NR^{5a}R^{15a}$, $(CH_2)_r NR^{15f}S(O)_2 R^{15b}$, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{5e}$;

$R^{15a}$, at each occurrence, is independently selected from H, $C_{1-6}$ alkyl, $C_{3-6}$ cycloalkyl, and $(CH_2)_r$phenyl substituted with 0-3 $R^{15e}$;

alternatively, two $R^{15a}$s, along with the N to which they are attached, join to form a 5-6 membered heterocyclic system containing 1-2 heteroatoms selected from NR$^{15g}$, O, and S and optionally fused with a benzene ring or a 6-membered aromatic heterocycle;

$R^{15b}$, at each occurrence, is independently selected from H, $C_{1-6}$ alkyl, $C_{3-6}$ cycloalkyl, and $(CH_2)_r$phenyl substituted with 0-3 $R^{15e}$;

$R^{15d}$, at each occurrence, is independently selected from $C_{1-6}$ alkyl and phenyl;

$R^{15e}$, at each occurrence, is independently selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is independently selected from H, and $C_{1-5}$ alkyl.

8. The compound of claim 4, wherein:
Z is O, N(CN), and $NC(O)NH_2$;
E is

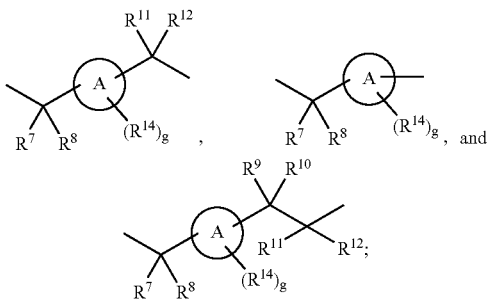

B is O;
$R^5$ is $CH_2$phenyl substituted with 0-3 $R^{16}$; and
r is selected from 0, 1, and 2.

9. The compound of claim 8, wherein:
Z is selected from O, N(CN) and $NC(O)NH_2$;
$R^3$ is a $C_{3-10}$ carbocyclic residue substituted with 0-3 $R^{15}$, wherein the carbocyclic residue is selected from cyclopropyl, cyclobutyl, cyclopentyl, cyclohexyl, phenyl, naphthyl and adamantyl, and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{15}$, at each occurrence, is independently selected from $C_{1-8}$ alkyl, $(CH_2)_rC_{3-6}$ cycloalkyl, $CF_3$, Cl, Br, I, F, $(CH_2)_rNR^{15a}R^{15a}$, $NO_2$, CN, OH, $(CH_2)_rOR^{15d}$, $(CH_2)_rC(O)R^{15b}$, $(CH_2)_rC(O)NR^{15a}R^{15a}$, $(CH_2)_rNR^{5f}C(O)R^{15b}$, $(CH_2)_rOC(O)NR^{15a}R^{15a}$, $(CH_2)_rNR^{15f}C(O)OR^{15b}$, $(CH_2)_rS(O)_pR^{15b}$, $(CH_2)_rS(O)_2NR^{15a}R^{15a}$, $(CH_2)_rNR^{15f}S(O)_2R^{15b}$, $(CH_2)_r$phenyl substituted with 0-3 $R^{15e}$, and a $(CH_2)_r$-5-6 membered heterocyclic system containing 1-4 heteroatoms selected from N, O, and S, substituted with 0-2 $R^{15e}$;

$R^{15a}$, at each occurrence, is independently selected from H, $C_{1-6}$ alkyl, $C_{3-6}$ cycloalkyl, and $(CH_2)_r$phenyl substituted with 0-3 $R^{15e}$;

alternatively, two $R^{15a}$s, along with the N to which they are attached, join to form a 5-6 membered heterocyclic system containing 1-2 heteroatoms selected from $NR^{15g}$, O, and S and optionally fused with a benzene ring or a 6-membered aromatic heterocycle;

$R^{15b}$, at each occurrence, is independently selected from H, $C_{1-6}$ alkyl, $C_{3-6}$ cycloalkyl, and $(CH_2)_r$phenyl substituted with 0-3 $R^{15e}$;

$R^{15d}$, at each occurrence, is independently selected from $C_{1-6}$ alkyl and phenyl;

$R^{15e}$, at each occurrence, is independently selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is independently selected from H, and $C_{1-5}$ alkyl.

10. The compound of claim 9, wherein:
E is

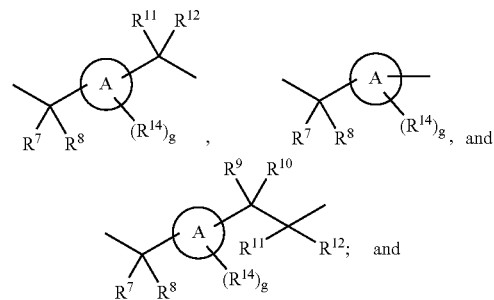

A is selected from cyclopropyl, cyclobutyl, cyclopentyl, cyclohexyl, and phenyl.

11. The compound of claim 3, wherein:
E is selected from $(C=O)-(CR^9R^{10})_v-(CR^{11}R^{12})-$,

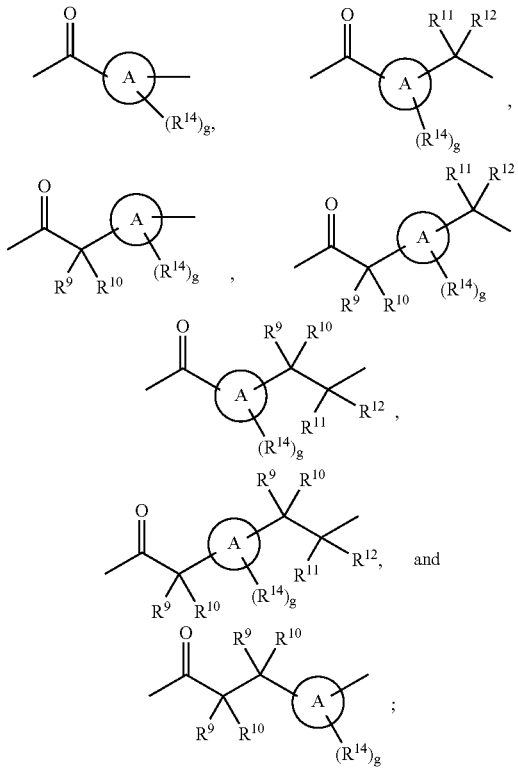

$R^3$ is a $C_{3-10}$ carbocyclic residue substituted with 0-3 $R^{15}$, wherein the carbocyclic residue is selected from cyclopropyl, cyclobutyl, cyclopentyl, cyclohexyl, phenyl, naphthyl and adamantyl, and a $(CR^{3a}H)_r$-heterocyclic system substituted with 0-3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

12. The compound of claim 11, wherein:
E is (C=O)—$(CR^9R^{10})_v$—$(CR^{11}R^{12})$—.

13. The compound of claim 11, wherein:
E is

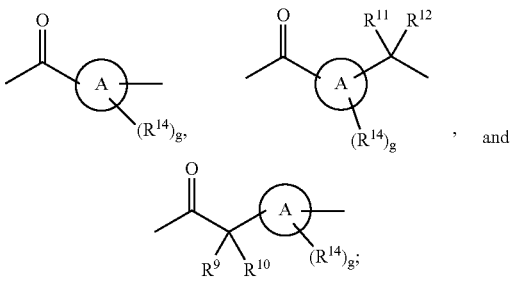

A is selected from cyclopropyl, cyclobutyl, cyclopentyl cyclohexyl, and phenyl.

14. The compound of claim 4, wherein:
$R^9$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{9d}$, $(CH_2)_rSR^{9d}$, $(CH_2)_rNR^{9a}R^{9a}$, $(CH_2)_rC(O)OH$, $(CH_2)_rC(O)R^{9b}$, $(CH_2)_rC(O)NR^{9a}R^{9a}$, $(CH_2)_rNR^{9a}C(O)R^{9b}$, $(CH_2)_rNR^{9a}C(O)H$, $C_{1-6}$ haloalkyl, a $(CH_2)_r$—$C_{3-11}$ carbocyclic residue substituted with 0-5 $R^{9c}$, and a $(CH_2)_r$-5-10 membered heterocyclic system containing 1-4 heteroatoms selected from N, O, and S, substituted with 0-3 $R^{9c}$;

$R^{9a}$, at each occurrence, is independently selected from H, $C_{1-6}$ alkyl, $C_{3-8}$ alkenyl, $C_{3-8}$ alkynyl, a $(CH_2)_r$—$C_{3-10}$ carbocyclic residue substituted with 0-5 $R^{9e}$, and a $(CH_2)_r$-4-10 membered heterocyclic system containing 1-4 heteroatoms selected from N, O, and S, substituted with 0-3 $R^{9e}$;

alternatively, two $R^{9a}$s, along with the N to which they are attached, join to form a 5-6 membered heterocyclic system containing 1-2 heteroatoms selected from $NR^{9g}$, O, and S and optionally fused with a benzene ring or a 6-membered aromatic heterocycle;

$R^{10}$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{10d}$, $(CH_2)_rSR^{10d}$, $(CH_2)_rNR^{10a}R^{10a}$;

alternatively, $R^9$ and $R^{10}$ join to form =O, a $C_{3-10}$ cycloalkyl, a 5-6-membered lactone or lactam, or a 4-6-membered saturated heterocycle containing 1-2 heteroatoms selected from O, S, and $NR^{10g}$ and optionally fused with a benzene ring or a 6-membered aromatic heterocycle;

$R^{11}$, is selected from H, $C_{1-6}$ alkyl, $C_{2-8}$ alkenyl, $C_{2-8}$ alkynyl, $(CR'R^{11})_qOH$, $(CH_2)_qSH$, $(CR'R^{11})OR^{11d}$, $(CH_2)_qSR^{11d}$;

$R^{12}$, is selected from H, $C_{1-6}$ alkyl, $C_{2-8}$ alkenyl, $C_{2-8}$ alkynyl, $(CHR')_qOH$, $(CH_2)_qSH$, $(CHR')_qOR^{12d}$, $(CH_2)_qSR^{12d}$, $(CHR')_qNR^{12a}R^{12a}$; and $R^{14}$, at each occurrence, is independently selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a}$, $(CHR')_rOH$, $(CHR')_rO(CHR')_rR^{4d}$, $(CHR')_rSH$, $(CHR')_rC(O)H$, $(CHR')_rS(CHR')_rR^{14d}$.

15. The compound of claim 1 wherein the compound is selected from:
N-phenyl-N'-{(1R,2S)-2-[(2S)-2-benzyl-6-oxo-morpholin-4-yl-methyl]-cyclohexyl}-urea;
N-(3-Acetyl-phenyl)-N'-{(1R,2S)-2-[(2S)-2-(benzyl)-6-oxo-morpholin-4-yl-methyl]-cyclohexyl}-urea; N-(3,5-di-Acetyl-phenyl)-N'-{(1R,2S)-2-[(2S)-2-(benzyl)-6-oxo-morpholin-4-yl-methyl]-cyclohexyl}-urea;
N-[3-(1-methyl-1H-tetrazo-l5-yl)phenyl]-N'-{(1R,2S)-2-[(2S)-2-(benzyl)-6-oxo-morpholin-4-yl-methyl]-cyclohexyl}-urea.

16. A pharmaceutical composition, comprising a pharmaceutically acceptable carrier and a therapeutically effective amount of a compound according to claim 1.

17. A pharmaceutical composition comprising a pharmaceutically acceptable carrier and a therapeutically effective amount of a compound according to claim 1, or a pharmaceutically acceptable salt thereof.

18. A pharmaceutical composition comprising a pharmaceutically acceptable carrier and a therapeutically effective amount of a compound according to claim 10, or a pharmaceutically acceptable salt thereof.

19. A method for treating asthma, comprising administering to a patient in need thereof a therapeutically effective amount of a compound according to claim 1.

* * * * *

UNITED STATES PATENT AND TRADEMARK OFFICE
CERTIFICATE OF CORRECTION

PATENT NO.         : 7,514,430 B2
APPLICATION NO.    : 11/191447
DATED              : April 7, 2009
INVENTOR(S)        : George DeLucca It is certified that error appears in the above-identified patent and that said Letters Patent is hereby corrected as shown below:

Column 135

Line 50, Claim 1, after "$(CH_2)_rOC(O)R^{11b}$," insert
-- $(CH_2)_rC(=NR^{11f})NR^{11f}R^{11f}$, $(CH_2)_rNHC(=NR^{11f})NR^{11f}R^{11f}$, $(CH_2)_rS(O)_pR^{11b}$, --.

Column 136

Line 45, Claim 1, delete "$R^{12e}$;" and insert -- $R^{12c}$; --.

Column 138

Line 43, Claim 1, delete "tetrazole,;" and insert -- tetrazole; --.

Column 140

Line 24, Claim 2, delete "$(CH_2)_rNR^{19a}R^{19}$," and insert -- $(CH_2)_rNR^{19a}R^{19a}$, --.
Line 33, Claim 2, delete "$(CH)_w$-phenyl" and insert -- $(CH_2)_w$-phenyl --.

Column 141

Lines 10 to 15, Claim 3, after " 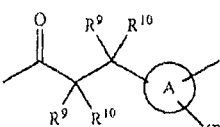 " insert -- , --.

Column 142

Line 17, Claim 4, delete "$R^{6e}$;" and insert -- $R^{16e}$; --.

Signed and Sealed this
Fourth Day of January, 2011

David J. Kappos
*Director of the United States Patent and Trademark Office*

Line 32, Claim 5, delete "$(CR^9R^{10})$" and insert -- $(CR^9R^{10})_n$ --.
Line 33, Claim 5, after "B is" delete "or".
Line 57, Claim 7, delete "$(CH_2)_rS(O)_2NR^{5a}R^{15a}$," and insert
-- $(CH_2)_rS(O)_2NR^{15a}R^{15a}$, --.
Line 61, Claim 7, delete "$R^{5e}$;" and insert -- $R^{15e}$; --.

Column 143

Line 53, Claim 9, delete "$(CH_2)_rNR^{5f}C(O)$" and insert -- $(CH_2)_rNR^{15f}C(O)$ --.

Column 145

Line 28, Claim 13, after "cyclopentyl" and insert -- , --.
Line 35, Claim 14, delete "H,$C_{1-6}$ and insert -- H, $C_{1-6}$ --.
Line 35, Claim 14, delete "$(CH_2)_r$—$C_{3-11}$" and insert -- $(CH_2)_r$—$C_{3-10}$ --.

Column 146

Line 13, Claim 14, delete "$(CR'R^{11})OR^{11d}$," and insert -- $(CR'R^{11})_qOR^{11d}$, --.
Line 21, Claim 14, delete "$_rR^{4d}$," and insert -- $_rR^{14d}$, --.
Line 31, Claim 15, delete "-tetrazo-15-" and insert -- -tetrazol-15- --.